(12) United States Patent
DeRosa et al.

(10) Patent No.: US 10,766,852 B2
(45) Date of Patent: *Sep. 8, 2020

(54) IONIZABLE CATIONIC LIPIDS

(71) Applicant: Translate Bio, Inc., Lexington, MA (US)

(72) Inventors: Frank DeRosa, Chelmsford, MA (US); Braydon Charles Guild, Concord, MA (US); Michael Heartlein, Boxborough, MA (US)

(73) Assignee: Translate Bio, Inc., Lexington, MA (US)

( * ) Notice: Subject to any disclaimer, the term of this patent is extended or adjusted under 35 U.S.C. 154(b) by 25 days.

This patent is subject to a terminal disclaimer.

(21) Appl. No.: 16/100,853

(22) Filed: Aug. 10, 2018

(65) Prior Publication Data
US 2019/0185410 A1 Jun. 20, 2019

Related U.S. Application Data

(63) Continuation of application No. 15/368,280, filed on Dec. 2, 2016, now Pat. No. 10,065,919, which is a continuation of application No. 14/389,023, filed as application No. PCT/US2013/034602 on Mar. 29, 2013, now Pat. No. 9,546,128.

(60) Provisional application No. 61/617,468, filed on Mar. 29, 2012.

(51) Int. Cl.
| | | |
|---|---|---|
| C07C 211/21 | (2006.01) |
| A61K 9/127 | (2006.01) |
| C12N 15/85 | (2006.01) |
| A61K 9/50 | (2006.01) |
| A61K 38/18 | (2006.01) |
| A61K 38/47 | (2006.01) |

(52) U.S. Cl.
CPC .......... *C07C 211/21* (2013.01); *A61K 9/1271* (2013.01); *A61K 9/1272* (2013.01); *A61K 9/5015* (2013.01); *A61K 38/1816* (2013.01); *A61K 38/47* (2013.01); *C12N 15/85* (2013.01); *C12Y 302/01023* (2013.01)

(58) Field of Classification Search
CPC .................................................... C07C 211/21
See application file for complete search history.

(56) References Cited

U.S. PATENT DOCUMENTS

| | | | |
|---|---|---|---|
| 5,488,172 A | 1/1996 | Cereghetti et al. |
| 5,965,434 A | 10/1999 | Wolff et al. |
| 7,662,409 B2 | 2/2010 | Masters |
| 8,936,942 B2 | 1/2015 | Heyes et al. |
| 8,980,864 B2 | 3/2015 | Hoge et al. |
| 8,999,351 B2 | 4/2015 | Manoharan et al. |
| 8,999,380 B2 | 4/2015 | Bancel et al. |
| 8,999,950 B2 | 4/2015 | MacLachlan et al. |
| 9,018,187 B2 | 4/2015 | Heyes et al. |
| 9,074,208 B2 | 7/2015 | MacLachlan et al. |
| 9,546,128 B2 | 1/2017 | DeRosa et al. |
| 2003/0082154 A1 | 5/2003 | Leamon |
| 2004/0204599 A1 | 10/2004 | Yang |
| 2009/0214649 A1 | 8/2009 | Gazit et al. |
| 2009/0263407 A1 | 10/2009 | Dande et al. |
| 2009/0270481 A1 | 10/2009 | MacLachlan et al. |
| 2011/0092739 A1 | 4/2011 | Chen et al. |
| 2011/0200582 A1 | 8/2011 | Baryza et al. |
| 2011/0223153 A1 | 9/2011 | Lu et al. |
| 2011/0256175 A1 | 10/2011 | Hope et al. |
| 2011/0311583 A1 | 12/2011 | Manoharan et al. |
| 2014/0314817 A1 | 10/2014 | Leisk et al. |
| 2015/0005372 A1 | 1/2015 | Hoge et al. |
| 2015/0017211 A1 | 1/2015 | de Fougerolles et al. |
| 2015/0044277 A1 | 2/2015 | Bancel et al. |
| 2015/0050354 A1 | 2/2015 | Bouchon et al. |
| 2015/0051268 A1 | 2/2015 | Bancel et al. |
| 2015/0064235 A1 | 3/2015 | Bancel et al. |
| 2015/0064236 A1 | 3/2015 | Bancel et al. |
| 2015/0064242 A1 | 3/2015 | Heyes et al. |
| 2015/0086614 A1 | 3/2015 | Bancel et al. |
| 2015/0111248 A1 | 4/2015 | Bancel et al. |
| 2015/0111945 A1 | 4/2015 | Geisbert et al. |
| 2015/0190515 A1 | 7/2015 | Manoharan et al. |
| 2015/0265708 A1 | 9/2015 | Manoharan et al. |

FOREIGN PATENT DOCUMENTS

| | | |
|---|---|---|
| DE | 3728917 A1 | 3/1989 |
| EP | 0068506 A1 | 6/1982 |
| EP | 0170470 A2 | 7/1985 |

(Continued)

OTHER PUBLICATIONS

Antonsson, et al., Palladium-Catalyzed Telomerization of Dienes and Tertiary Allylic Amines. A Novel Reaction Involving Cleavage of the Carbon-Nitrogen Bond, Organometallics, 4, 1083-1086 (1985).
Benmaarouf-Khallaayoun et al., Hydroboration D'Amines Insaturees, Journal of Organometallic Chemistry, 306, 283-293, (1986).
Blomqvist, et al., Studies on Orchidaceae Alkaloids, Acta Chemica Scandinaviaca, 26, 3203-3206, (1972).
Botteghi et al., "New Synthetic Route to Pharmacologically Active 1-(N,N-dialkylamino)-3,3-diarylpropanes via Rodhium-Catalyzed Hydroformulation of 1,1-Diarylethenes," Journal of Organic Chemistry, 60(20), 6612-6615, 1995.
Gupta et al., Quaternary Trialkyl(polyfluoroalkyl)ammonium Salts Including Liquid Iodides, Tetrahedron Letters, 44 (52), 9367-70, 2003.

(Continued)

*Primary Examiner* — Scott Long
(74) *Attorney, Agent, or Firm* — Fangli Chen; Proskauer Rose LLP

(57) ABSTRACT

Disclosed herein are novel compounds, pharmaceutical compositions comprising such compounds and related methods of their use. The compounds described herein are useful, e.g., as liposomal delivery vehicles to facilitate the delivery of encapsulated polynucleotides to target cells and subsequent transfection of said target cells, and in certain embodiments are characterized as having one or more properties that afford such compounds advantages relative to other similarly classified lipids.

18 Claims, 7 Drawing Sheets

Specification includes a Sequence Listing.

(56) References Cited

FOREIGN PATENT DOCUMENTS

| | | | |
|---|---|---|---|
| EP | 2449106 A1 | 5/2012 | |
| GB | 1379428 | 1/1975 | |
| GB | 2038826 A | 12/1979 | |
| JP | S50-123605 | 9/1975 | |
| JP | 04-026646 | 1/1992 | |
| JP | 09-040598 | 2/1997 | |
| JP | 09-309857 | 2/1997 | |
| JP | 2006169150 | 6/2006 | |
| WO | WO-2001/05375 A1 | 1/2001 | |
| WO | WO-2001/87267 A1 | 11/2001 | |
| WO | WO-2005/020849 A2 | 3/2005 | |
| WO | WO-2010/054405 A1 | 5/2010 | |
| WO | WO-2010/054406 A1 | 5/2010 | |
| WO | WO-2010/123947 A2 | 10/2010 | |
| WO | WO-2011/039144 A1 | 4/2011 | |
| WO | WO-2011/141703 A1 | 11/2011 | |
| WO | WO-2011/141705 A1 | 11/2011 | |
| WO | WO-2012/170889 A1 | 12/2012 | |
| WO | WO-2013/090186 A1 | 6/2013 | |
| WO | WO-2013/149141 A1 | 10/2013 | |
| WO | WO-2013/151669 A1 | 10/2013 | |
| WO | WO-2013/185069 A1 | 12/2013 | |
| WO | WO-2014/089486 A1 | 6/2014 | |
| WO | WO-2014/152940 A1 | 9/2014 | |
| WO | WO-2015/006747 A2 | 1/2015 | |
| WO | WO-2015/011633 A1 | 1/2015 | |
| WO | 2019/207060 A1 | 10/2019 | |

OTHER PUBLICATIONS

Huang, Z. et al., Thiocholesterol-Based Lipids for Ordered Assembly of Bioresponsive Gene Carriers, Molecular Therapy, 11(3):409-417 (2005).
International Search Report for PCT/US13/034602, 2 pages (dated Jun. 17, 2013).
International Search Report for PCT/US2012/041663, 4 pages (dated Oct. 8, 2012).
International Search Report for PCT/US2013/34604, 4 pages (dated Jun. 17, 2013).
Jamison et al., "Base Catalysed Rearrangements involving Ylide Intermediates. Part 4. [1,3] Sigmatropic Rearrangments of 4-Dimethylaminobutenes and [3,3] Sigmatropic Rearrangments of 3-Dimethylaminohexa-1,5-dienes," Journal of the Chemical Society, Perkin Transactions 1, (7) 1462-1472, 1980.
Laird et al., "Base Catalysed Rearrangements involving Ylide Intermediates. Part 7. The Rearrangements of Allyl(pentadienyl)-ammonium Cations. The [5,4] Sigmatropic Rearrangement," Journal of the Chemical Society, Perkin Transactions 1, (9) 2033-2048, 1980.
Laird et al., "[4,5] Anionic Sigmatropic Rearrangments," Journal of the Chemical Society, Chemical Communications, (18) 658-660, 1973.
Mauzé et al., Etude De L'Addition Des Organozinciques α-Ethyleniques Aux Amines Ethyleniques, Acetyleniques Et Alleniques, Journal of Organometallic Chemistry, 44(1), 69-96, (1972).
RN:1026676-60-7, 1-Buten-1-amine, N,N-bis(1-methylethyl)-4,4-diphenyl-,(1E)-, Registry (STN), entered STN Jun. 9, 2008.
RN:856565-03-2, 2-Buten-1-amine, N,N-dimethyl-4-(4-methylphenyl)-4-phenyl, Registry (STN), entered STN Jul. 22, 2005.
RN: 849-05-8, 2-Pentenylamine, N,N-diethyl-5,5-diphenyl-, Registry (STN), entered STN Nov. 16, 1984.
Sammour et al., "Diels-Alder and Grignard Reactions with Unsaturated Schiff Bases," United Arab Republic Journal of Chemistry, 14 (4), 371-382, 1971.
Sharp et al., An Unusual Isomerization Under Lawesson Thiation Conditions, Tetrahedron Letters, 35(22), 3651-2, (1994).
Tang, F. and Hughes, A., Introduction of a Disulfide Bond into a Cationic Lipid Enhances Transgene Expression of Plasmid DNA, Biochemical and Biophysical Research Communications, 242(1):141-145 (1998).
Wetzer, B. et al., Reducible Cationic Lipids for Gene Transfer, Journal of Biochemistry, 356:747-756 (2001).
Written Opinion for PCT/US2013/034602, 4 pages (dated Jun. 17, 2013).
Written Opinion for PCT/US2012/041663, 7 pages (dated Oct. 8, 2012).
Written Opinion for PCT/US2013/034604, 12 pages (dated Jun. 17, 2013).
Alton et al., "A randomised, double-blind, placebo-controlled trial of repeated nebulisation of non-viral cystic fibrosis transmembrane conductance regulator (CFTR) gene therapy in patients with cystic fibrosis", National Institute for Health Research, 3(5), (2016).

SEQUENCE LISTING

```
<160> NUMBER OF SEQ ID NOS: 4

<210> SEQ ID NO 1
<211> LENGTH: 1309
<212> TYPE: RNA
<213> ORGANISM: Homo sapiens

<400> SEQUENCE: 1
gggauccuac caugcagcug aggaacccag aacuacaucu gggcugcgcg cuugcgcuuc      60
gcuuccuggc ccucguuucc ugggacaucc cuggggcuag agcacuggac aauggauugg     120
caaggacgcc uaccaugggc uggcugcacu gggagcgcuu caugugcaac cuugacugcc     180
aggaagagcc agauuccugc aucagugaga agcucuucau ggagauggca gagcucaugg     240
ucucagaagg cuggaaggau gcagguuaug aguaccucug cauugaugac uguuggaugg     300
cuccccaaag agauucagaa ggcagacuuc aggcagaccc ucagcgcuuu ccucauggga     360
uucgccagcu agcuaauuau guucacagca aaggacugaa gcuagggauu uaugcagaug     420
uuggaaauaa aaccugcgca ggcuucccug ggaguuuugg auacuacgac auugaugccc     480
agaccuuugc ugacugggga guagaucugc uaaaauuuga ugguuguuac ugugacaguu     540
uggaaaauuu ggcagauggu uauaagcaca uguccuuggc ccugaauagg acuggcagaa     600
gcauugugua cuccugugag uggccucuuu auaugugggcc cuuucaaaag cccaauuaua     660
cagaaauccg acaguacugc aaucacuggc gaaauuuugc ugacauugau gauuccugga     720
aaaguauaaa gaguaucuug gacuggacau cuuuuaacca ggagagaauu guugauguug     780
cuggaccagg ggguuggaau gacccagaua uguuagugau uggcaacuuu ggccucagcu     840
ggaaucagca aguaacucag auggcccucu gggcuaucau ggcugcuccu uuauucaugu     900
cuaaugaccu ccgacacauc agcccucaag ccaaagcucu ccuucaggau aaggacguaa     960
uugccaucaa ucaggacccc uugggcaagc aagguacca gcuuagacag ggagacaacu    1020
uugaagugug ggaacgaccu cucucaggcu uagccuuggc uguagcuaug auaaaccggc    1080
aggagauugg uggaccucgc ucuuauacca ucgcaguugc uucccugggu aaaggagugg    1140
```

```
ccuguaaucc ugccugcuuc aucacacagc uccucccugu gaaaaggaag cuagggUUCU    1200
augaauggac uucaagguua agaagucaca uaaaucccac aggcacuguu uugcuucagc    1260
uagaaaauac aaugcagaug ucauuaaaag acuuacuuua auuugaauu               1309
```

<210> SEQ ID NO 2
<211> LENGTH: 11
<212> TYPE: RNA
<213> ORGANISM: Homo sapiens

<400> SEQUENCE: 2

```
gggauccuac c                                                          11
```

<210> SEQ ID NO 3
<211> LENGTH: 8
<212> TYPE: RNA
<213> ORGANISM: Homo sapiens

<400> SEQUENCE: 3

```
uuugaauu                                                               8
```

<210> SEQ ID NO 4
<211> LENGTH: 1309
<212> TYPE: RNA
<213> ORGANISM: Homo sapiens

<400> SEQUENCE: 4

```
gggauccuac caugcagcug aggaacccag aacuacaucu gggcugcgcg cuugcgcuuc      60
gcuuccuggc ccucguuccc ugggacaucc cuggggcuag agcacuggac aauggauugg     120
caaggacgcc uaccaugggc uggcugcacu gggagcgcuu caugugcaac cuugacugcc     180
aggaagagcc agauuccugc aucagugaga agcucuucau ggagauggca gagcucaugg     240
ucucagaagg cuggaaggau gcagguuaug aguaccucug cauugaugac uguuggaugg     300
cuccccaaag agauucagaa ggcagacuuc aggcagaccc ucagcgcuuu ccucauggga     360
uucgccagcu agcuaauuau guucacagca aaggacugaa gcagggauu uaugcagaug     420 uuggaaauaa aaccugcgca ggcuucccug ggaguuuugg auacuacgac auugaugccc     480
agaccuuugc ugacgggga guagaucugc uaaaauuuga ugguuguuac ugugacaguu     540
uggaaaauuu ggcagauggu uauaagcaca uguccuuggc ccugaauagg acggcagaa     600 gcauugugua cuccugugag uggccucuuu auauguggcc cuuucaaaag cccaauuaua    660
cagaaauccg acaguacugc aaucacuggc gaaauuuugc ugacauugau gauuccugga    720
aaaguauaaa gaguaucuug gacuggacau cuuuuaacca ggagagaauu guugauguug    780
cuggaccagg gguuggaau gacccagaua uguuagugau uggcaacuuu ggccucagcu    840
ggaaucagca aguaacucag auggccccucu gggcuaucau ggcugcuccu uuauucaugu    900
cuaaugaccu ccgacacauc agcccucaag ccaaagcucu ccuucaggau aaggacguaa    960
uugccaucaa ucaggacccc uugggcaagc aagggυасса gcuuagacag ggagacaacu   1020 uugaaguguɡ ggaacgaccu cucucaggcu uagccugggc uguagcuaug auaaaccggc   1080
aggagauugg uggaccucgc ucuuauacca ucgcaguugc uucccgggu aaggagugg     1140 ccuguaaucc ugccugcuuc aucacacagc uccucccugu gaaaaggaag cuagggUUCU    1200
augaauggac uucaagguua agaagucaca uaaaucccac aggcacuguu uugcuucagc    1260
uagaaaauac aaugcagaug ucauuaaaag acuuacuuua auuugaauu               1309
```

IONIZABLE CATIONIC LIPIDS

RELATED APPLICATIONS

This application is a continuation of U.S. application Ser. No. 15/368,280, filed Dec. 2, 2016, which is a continuation of U.S. application Ser. No. 14/389,023, filed Sep. 29, 2014, and which issued as U.S. Pat. No. 9,546,128 on Jan. 17, 2017, which is the U.S. National Stage of International Application No. PCT/US2013/034602, filed Mar. 29, 2013, which claims the benefit of U.S. Provisional Application No. 61/617,468, filed on Mar. 29, 2012, the disclosures of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Aug. 9, 2018, is named MRT-1060US3_ST25.txt and is 4,212 bytes in size.

BACKGROUND

Liposomal delivery of nucleic acids has been employed as a means of effectuating the site-specific delivery of encapsulated plasmid DNA, antisense oligonucleotides, short interfering RNA and microRNA-based therapies, however the efficient delivery of nucleic acids to targeted cells and tissues, as well as the subsequent transfection of such targeted cells and tissues remains a technical challenge. Despite the availability of multiple liposomal-based systems and vehicles to facilitate the delivery of therapeutic agents to target cells and tissues, many problems still exist both in in vivo and in vitro applications. For example, a significant drawback of liposomal delivery systems relates to the construction of liposomes that have sufficient cell culture or in vivo stability to reach desired target cells and/or intracellular compartments, and the ability of such liposomal delivery systems to efficiently release their encapsulated materials to such target cells.

Furthermore, many of the cationic lipids that are employed to construct such liposomal-based vehicles are generally toxic to the targeted cells. In particular, the amount of such cationic lipid that is necessary to deliver a therapeutically effective amount of the encapsulated agent may be toxic to the targeted cells. Accordingly, the toxicity associated with cationic lipid represents a significant obstacle to their general use as non-viral vectors, particularly in the quantities necessary to successfully deliver therapeutically effective amounts of the encapsulated materials to target cells.

Despite the foregoing limitations, and as a results of their ability to protect and facilitate the delivery of encapsulated materials to one or more target cells, liposomal-based vehicles are considered an attractive carrier for therapeutic agents and remain subject to continued development efforts. While liposomal-based vehicles that comprise a cationic lipid component have shown promising results with regards to encapsulation, stability and site localization, there remains a great need for improvement of liposomal-based delivery systems. In particular, there remains a need for improved cationic and ionizable lipids that demonstrate improved pharmacokinetic properties and which are capable of delivering macromolecules, such as nucleic acids to a wide variety cell types and tissues with enhanced efficiency. Importantly, there also remains a particular need for novel cationic ionizable lipids that are characterized as having reduced toxicity and are capable of efficiently delivering encapsulated nucleic acids and polynucleotides to targeted cells, tissues and organs.

SUMMARY

Described herein are novel cationic and ionizable lipid compounds, pharmaceutical compositions comprising such compounds and related methods of their use. In certain embodiments, the compounds described herein are useful as liposomal compositions or as components of liposomal compositions to facilitate the delivery to, and subsequent transfection of one or more target cells. In certain embodiments, the lipid compositions disclosed herein are cationic and/or ionizable lipids. For example, the lipid compounds disclosed herein may comprise a basic ionizable functional group such as an amine. In some embodiments, the compounds described herein have been designed based on one or more desired characteristics or properties, for example to enhance transfection efficiency or to promote specific biological outcomes.

In certain embodiments disclosed herein, the lipid compounds generally comprise a polar, hydrophilic head-group and a non-polar, hydrophobic tail-group. For example, the lipid compounds disclosed herein may generally comprise one or more cationic and/or ionizable functional head-groups, such as an amine functional group having one or more alkyl or aryl substituents. In certain embodiments the lipid compounds disclosed herein may comprise a cationic ionizable amino functional head-group to which is bound (e.g., covalently bound) two alkyl functional groups, substituents or moieties (e.g., an $R_1$ group and a $R_2$ group, wherein both $R_1$ and $R_2$ are independently selected from the group consisting of $C_1$-$C_{10}$ alkyls).

In some embodiments the hydrophilic head-group (e.g., an alkyl amino group) is bound (e.g., covalently bound) to a hydrophobic (lipophilic) tail-group. For example, the lipophilic tail-group (e.g., one or more of an $L_1$ group and an $L_2$ group) of the compounds disclosed herein may comprise one or more non-polar groups such as cholesterol or an optionally substituted, variably unsaturated alkyl (e.g., an optionally substituted octadeca-9,12-diene or octadec-6,9-diene).

In certain embodiments, the present invention relates to compounds having the structure of formula (I):

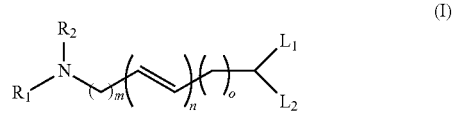

(I)

wherein $R_1$ and $R_2$ are each independently selected from the group consisting of hydrogen, an optionally substituted, variably saturated or unsaturated $C_1$-$C_{20}$ alkyl and an optionally substituted, variably saturated or unsaturated $C_6$-$C_{20}$ acyl; wherein $L_1$ and $L_2$ are each independently selected from the group consisting of hydrogen, an optionally substituted $C_1$-$C_{30}$ alkyl, an optionally substituted variably unsaturated $C_1$-$C_{30}$ alkenyl, and an optionally substituted $C_1$-$C_{30}$ alkynyl; wherein m and o are each independently selected from the group consisting of zero and any positive integer (e.g., where m is three); and wherein n is zero or any positive integer (e.g., where n is one).

In certain embodiments, the compound has the structure of formula (I), wherein $R_1$ and $R_2$ are each methyl. In such embodiment, the polar cationic head-group of the compound comprises an ionizable dimethyl amino group.

In some embodiments, the compound has the structure of formula (I), wherein $L_1$ and $L_2$ are each an optionally substituted, polyunsaturated $C_6$-$C_{20}$ alkenyl. For example, contemplated are compounds wherein $L_1$ and $L_2$ are each an optionally substituted polyunsaturated $C_{18}$ alkenyl. In other embodiments, $L_1$ and $L_2$ are each an unsubstituted, polyunsaturated $C_{18}$ alkenyl. In yet other embodiments, $L_1$ and $L_2$ are each an optionally substituted octadeca-9,12-diene (or octadec-6,9-diene). In still other embodiments, $L_1$ is hydrogen and $L_2$ is cholesterol.

In certain embodiments disclosed herein, the present inventions relate to a compound having the structure of formula (I), wherein o is zero. Alternatively, in other embodiments, o is a positive integer (e.g., one, two, three, four, five, six, seven, eight, nine, ten, eleven, twelve, thirteen, fourteen, fifteen, sixteen, seventeen, eighteen, nineteen, twenty, or more).

In certain embodiments disclosed herein, the present inventions relate to a compound having the structure of formula (I), wherein m is a positive integer (e.g., one, two, three, four, five, six, seven, eight, nine, ten, eleven, twelve, thirteen, fourteen, fifteen, sixteen, seventeen, eighteen, nineteen, twenty, or more). In some particular embodiments, the present inventions relate to a compound having the structure of formula (I), wherein m is four. In some particular embodiments, the present inventions relate to a compound having the structure of formula (I), wherein m is three.

Also disclosed herein are compounds having the structure of formula (I), wherein n is a positive integer (e.g., one, two, three, four, five, six, seven, eight, nine, ten, eleven, twelve, thirteen, fourteen, fifteen, sixteen, seventeen, eighteen, nineteen, twenty, or more). In other particular embodiments, the present inventions relate to a compound having the structure of formula (I), wherein n is zero.

In some particular embodiments, the present invention relates to a compound having the structure of formula (I), wherein $R_1$ and $R_2$ are each methyl; wherein $L_1$ and $L_2$ are each octadeca-9,12-diene (or octadec-6,9-diene); wherein m is four; wherein n is zero; and wherein o is one. For example, in certain embodiments, the present invention relates to the compound (15Z,18Z)—N,N-dimethyl-6-(9Z,12Z)-octadeca-9,12-dien-1-yl)tetracosa-15,18-dien-1-amine. In certain embodiments, the present invention relates to a compound having the structure of formula (II), (referred to herein as "HGT5000").

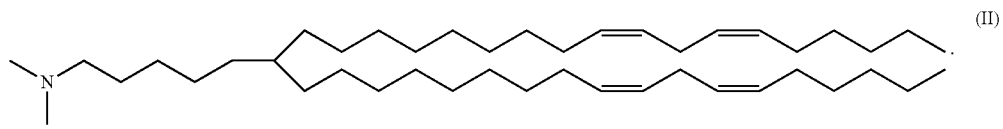 [SMILES: CCCCC/C=C\C/C=C\CCCCCCCCC(CCCCCCCC/C=C\C/C=C\CCCCC)CCCCCN(C)C]

In some particular embodiments, the present invention relates to a compound having the structure of formula (I), wherein $R_1$ and $R_2$ are each methyl; wherein $L_1$ and $L_2$ are each octadeca-9,12-diene (or octadec-6,9-diene); wherein m is 3; wherein n is one; and wherein o is zero. For example, in certain embodiments, the present invention relates to the compound (15Z,18Z)—N,N-dimethyl-6-((9Z,12Z)-octadeca-9,12-dien-1-yl)tetracosa-4,15,18-trien-1-amine. In certain embodiments, the present invention relates to a compound having the structure of formula (III), (referred to herein as "HGT5001").

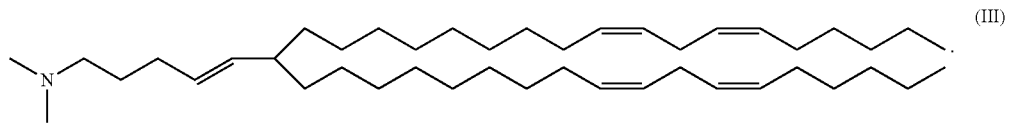 [SMILES: CCCCC/C=C\C/C=C\CCCCCCCCC(/C=C/CCCN(C)C)CCCCCCCC/C=C\C/C=C\CCCCC]

It should be understood that in those embodiments disclosed herein where n is one, such compounds may be a cis isomer, a trans isomer or alternatively a racemic mixture thereof. For example, in certain embodiments where n is one, n is a cis isomer, as represented by a compound having the structure of formula (IV):

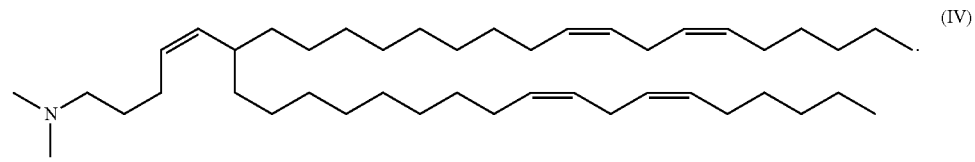

Alternatively, in other embodiments where n is one, n is a trans isomer, as represented by a compound having the structure of formula (V):

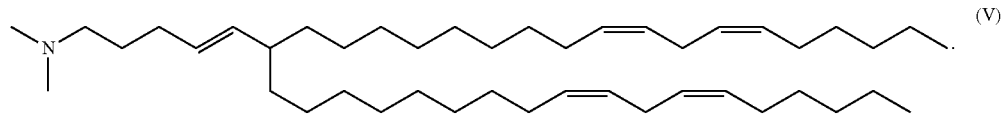 [SMILES: CCCCC/C=C\C/C=C\CCCCCCCCC(/C=C/CCCN(C)C)CCCCCCCC/C=C\C/C=C\CCCCC]

(V)

Also disclosed are compounds having the structure of formula (VI):

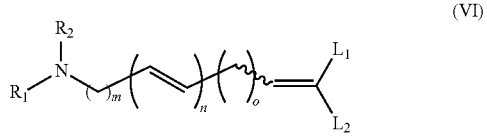

(VI)

wherein $R_1$ and $R_2$ are each independently selected from the group consisting of hydrogen, an optionally substituted, variably saturated or unsaturated $C_1$-$C_{20}$ alkyl and an optionally substituted, variably saturated or unsaturated $C_6$-$C_{20}$ acyl; wherein $L_1$ and $L_2$ are each independently selected from the group consisting of hydrogen, an optionally substituted $C_1$-$C_{30}$ alkyl, an optionally substituted variably unsaturated $C_1$-$C_{30}$ alkenyl, and an optionally substituted $C_1$-$C_{30}$ alkynyl; and wherein m, n and o are each independently selected from the group consisting of zero and any positive integer.

In some particular embodiments, the present inventions are directed to a compound having the structure of formula (VI), wherein $R_1$ and $R_2$ are each methyl. In other embodiments, the present inventions are directed to a compound having the structure of formula (VI), wherein $R_1$ and $R_2$ are each independently selected from the group consisting of hydrogen and methyl.

Also contemplated are compounds having the structure of formula (VI), wherein $L_1$ and $L_2$ are each an optionally substituted, polyunsaturated $C_6$-$C_{20}$ alkenyl (e.g., where $L_1$ and $L_2$ are each an optionally substituted polyunsaturated $C_{18}$ alkenyl or where $L_1$ and $L_2$ are each an unsubstituted, polyunsaturated $C_{18}$ alkenyl). In certain embodiments, disclosed herein, $L_1$ and $L_2$ are each an optionally substituted octadeca-9,12-diene (or octadec-6,9-diene). In other embodiments $L_1$ is hydrogen and $L_2$ is cholesterol.

In certain embodiments disclosed herein, the present inventions relate to a compound having the structure of formula (VI), wherein m is a positive integer (e.g., one, two, three, four, five, six, seven, eight, nine, ten, eleven, twelve, thirteen, fourteen, fifteen, sixteen, seventeen, eighteen, nineteen, twenty, or more). In some particular embodiments, the present inventions relate to a compound having the structure of formula (VI), wherein m is four. In certain embodiments, the present inventions relate to a compound having the structure of formula (VI), wherein m is at least five (e.g., where m is five, six, seven, eight, nine, ten, eleven, twelve, thirteen, fourteen, fifteen, sixteen, seventeen, eighteen, nineteen, twenty or more).

Also disclosed herein are compounds having the structure of formula (VI), wherein n is a positive integer (e.g., one, two, three, four, five, six, seven, eight, nine, ten, eleven, twelve, thirteen, fourteen, fifteen, sixteen, seventeen, eighteen, nineteen, twenty, or more). In other particular embodiments, the present inventions relate to a compound having the structure of formula (VI), wherein n is zero.

In certain embodiments disclosed herein, the present inventions are directed to compounds having the structure of formula (VI), wherein o is a positive integer (e.g., one, two, three, four, five, six, seven, eight, nine, ten, eleven, twelve, thirteen, fourteen, fifteen, sixteen, seventeen, eighteen, nineteen, twenty, or more). In certain embodiments, the present inventions relate to a compound having the structure of formula (VI), wherein o is at least five (e.g., where o is five, six, seven, eight, nine, ten, eleven, twelve, thirteen, fourteen, fifteen, sixteen, seventeen, eighteen, nineteen, twenty or more). Alternatively, in other particular embodiments, the present inventions relate to compounds having the structure of formula (VI), wherein o is zero.

Also contemplated are compounds having the structure of formula (VI), wherein $R_1$ and $R_2$ are each methyl; wherein $L_1$ and $L_2$ are each octadeca-9,12-diene (or octadec-6,9-diene); wherein m is 4; and wherein both n and o are zero. For example, in certain embodiments, the present invention relates to the compound (15Z,18Z)—N,N-dimethyl-6-((9Z,12Z)-octadeca-9,12-dien-1-yl)tetracosa-5,15,18-trien-1-amine. In certain embodiments, the present invention relates to the compound having the structure of formula (VII), (referred to herein as "HGT5002"):

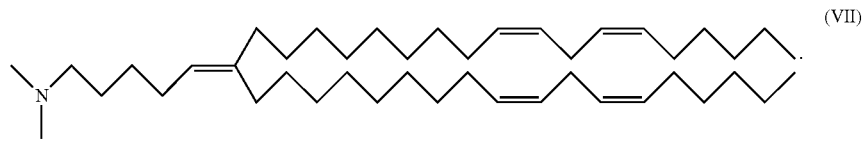

(VII)

Also disclosed herein are compounds having the structure of formula (VIII):

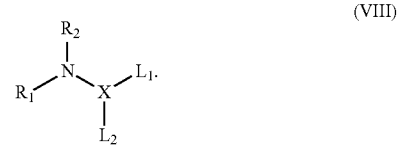

(VIII)

wherein $R_1$ and $R_2$ are each independently selected from the group consisting of an optionally substituted, variably saturated or unsaturated $C_1$-$C_{20}$ alkyl or alkenyl and an optionally substituted, variably saturated or unsaturated $C_6$-$C_{20}$ acyl; wherein $L_1$ and $L_2$ are each independently selected from the group consisting of an optionally substituted $C_1$-$C_{30}$ alkyl, an optionally substituted variably unsaturated $C_1$-$C_{30}$ alkenyl, and an optionally substituted $C_1$-$C_{30}$ alkynyl; and wherein x is selected from the group consisting of a $C_1$-$C_{20}$ alkyl and a variably unsaturated $C_1$-$C_{20}$ alkenyl.

In certain embodiments, the disclosed compounds have the structure of formula (VIII), wherein $R_1$ and $R_2$ are each methyl. In other embodiments, the disclosed compounds have the structure of formula (VIII), wherein $R_1$ and $R_2$ are independently selected from the group consisting of hydrogen and a $C_1$-$C_6$ alkyl.

In other embodiments, the present invention relates to compounds having the structure of formula (VIII), wherein $L_1$ and $L_2$ are each an unsubstituted, polyunsaturated $C_{18}$ alkenyl. For example, in certain embodiments, $L_1$ and $L_2$ are each an optionally substituted octadeca-9,12-diene (e.g., $L_1$ and $L_2$ are each an unsubstituted octadeca-9,12-diene or octadec-6,9-diene). In certain other embodiments, $L_1$ is hydrogen and $L_2$ is cholesterol.

In certain embodiments, the disclosed compounds have the structure of formula (VIII), wherein x is a $C_6$ alkenyl. In other embodiments, the disclosed compounds have the structure of formula (VIII), wherein x is hexane. In yet other embodiments, the disclosed compounds have the structure of formula (VIII), wherein x is hex-1-ene. In still other embodiments, the disclosed compounds have the structure of formula (VIII), wherein x is hex-2-ene. In certain embodiments, x is not hexane. In other embodiments, the disclosed compounds have the structure of formula (VIII), wherein x is a $C_{6-10}$ alkenyl or a $C_{6-10}$ alkyl.

In one particular embodiment, the present invention relates to a compound having the structure of formula (VIII), wherein $R_1$ and $R_2$ are each methyl; wherein $L_1$ and $L_2$ are each octadeca-9,12-diene (or octadec-6,9-diene); and wherein x is hexane. In another particular embodiment, the present invention relates to a compound having the structure of formula (VIII), wherein $R_1$ and $R_2$ are each methyl; wherein $L_1$ and $L_2$ are each octadeca-9,12-diene (or octadec-6,9-diene); and wherein x is hex-1-ene. In still another particular embodiment, the present invention relates to a compound having the structure of formula (VIII), wherein $R_1$ and $R_2$ are each methyl; wherein $L_1$ and $L_2$ are each octadeca-9,12-diene (or octadec-6,9-diene); and wherein x is hex-2-ene.

It should be understood that in those embodiments described herein where the compounds have one or more asymmetric or chiral molecules (e.g., one or more unsaturated carbon-carbon double bonds), both the cis (Z) and trans (E) isomers are within the scope of this invention.

The compositions disclosed herein may be used to prepare one or more pharmaceutical compositions and/or liposomal vehicles (e.g., a lipid nanoparticle). In such embodiments, such pharmaceutical compositions or vehicles may further comprise one or more compounds selected from the group consisting of a cationic lipid, a PEG-modified lipid, a non-cationic lipid and a helper lipid. Accordingly, in certain embodiments, the compounds described herein (e.g., HGT5000, HGT5001, and/or HGT5002) are cationic or ionizable lipids that may be used as a component of a liposomal composition to facilitate or enhance the delivery and release of encapsulated materials (e.g., one or more therapeutic agents) to one or more target cells (e.g., by permeating or fusing with the lipid membranes of such target cells). Enriching liposomal compositions with one or more of the compounds disclosed herein may be used as a means of improving (e.g., reducing) the toxicity or otherwise conferring one or more desired properties to such enriched liposomal composition (e.g., improved delivery of the encapsulated polynucleotides to one or more target cells and/or reduced in vivo toxicity of a liposomal composition). Accordingly, also contemplated are pharmaceutical compositions, and in particular liposomal compositions, that comprise one or more of the compounds disclosed herein. In certain embodiments, such pharmaceutical and liposomal compositions comprise one or more of a PEG-modified lipid, a non-cationic lipid and a helper lipid. For example, contemplated are pharmaceutical and liposomal compositions (e.g., lipid nanoparticles) that comprise one or more of the compounds disclosed herein (e.g., HGT5000, HGT5001, and/or HGT5002) and one or more helper lipids, non-cationic lipids and PEG-modified lipids components. Also contemplated are pharmaceutical and liposomal compositions that comprise one or more of the compounds disclosed herein and that further comprise one or more additional cationic lipids. Similarly, also contemplated are liposomal compositions and pharmaceutical compositions (e.g., a lipid nanoparticle) that comprise one or more of the HGT5000, HGT5001 and/or HGT5002 compounds and one or more of C12-200, DLinDMA, CHOL, DOPE, DMG-PEG-2000, ICE, DSPC, DODAP, DOTAP and C8-PEG-2000. In certain embodiments, such pharmaceutical compositions and liposomal compositions are loaded with or otherwise encapsulate materials, such as for example, one or more biologically-active polynucleotides.

In certain embodiments one or more of the pharmaceutical and liposomal compositions described herein (e.g., lipid nanoparticles) comprise one or more of the compounds disclosed herein and one or more additional lipids. For example, lipid nanoparticles that comprise or are otherwise enriched with one or more of the compounds disclosed herein may further comprise one or more of DOTAP (1,2-dioleyl-3-trimethylammonium propane), DODAP (1,2-dioleyl-3-dimethylammonium propane), DOTMA (1,2-di-O-octadecenyl-3-trimethylammonium propane), DLinDMA, DLin-KC2-DMA, C12-200 and ICE. In one embodiment the pharmaceutical composition comprises a lipid nanoparticle that comprises HGT5000, DOPE, cholesterol and/or DMG-PEG2000. In another embodiment the pharmaceutical composition comprises a lipid nanoparticle that comprises HGT5001, DOPE, cholesterol and/or DMG-PEG2000. In yet another embodiment the pharmaceutical composition comprises a lipid nanoparticle that comprises HGT5002, DOPE, cholesterol and/or DMG-PEG2000.

In certain embodiments one or more of the pharmaceutical compositions described herein may comprise one or more PEG-modified lipids. For example, lipid nanoparticles that comprise or are otherwise enriched with one or more of the compounds disclosed herein may further comprise one or more of PEG-modified lipids that comprise a poly(ethylene)glycol chain of up to 5 kDa in length covalently attached to a lipid comprising one or more $C_6$-$C_{20}$ alkyls.

Similarly, the pharmaceutical compositions disclosed herein (e.g., lipid nanoparticles) may comprise or may otherwise be enriched with one or more of the compounds disclosed herein and may further comprise one or more of helper lipids that are selected from the group consisting of DSPC (1,2-distearoyl-sn-glycero-3-phosphocholine), DPPC (1,2-dipalmitoyl-sn-glycero-3-phosphocholine), DOPE (1,2-dioleyl-sn-glycero-3-phosphoethanolamine), DPPE (1,2-dipalmitoyl-sn-glycero-3-phosphoethanolamine), DMPE (1,2-dimyristoyl-sn-glycero-3-phosphoethanolamine), DOPG (,2-dioleoyl-sn-glycero-3-phospho-(1'-rac-glycerol)), DOPE (1,2-dioleoyl-sn-glycero-3-phosphoethanolamine), DSPE (1,2-distearoyl-sn-glycero-3-phosphoethanolamine), DLPE (1,2-dilauroyl-sn-glycero-3-phosphoethanolamine), DPPS (1,2-dipalmitoyl-sn-glycero-3-phospho-L-serine), ceramides, sphingomyelins and cholesterol.

In certain embodiments, the compounds and the pharmaceutical and liposomal compositions comprising such compounds (e.g., lipid nanoparticles) comprise one or more polynucleotides (e.g., encapsulated DNA or RNA). In other embodiments, the one or more polynucleotides comprise at least one locked nucleic acid (e.g., two, three, four, five, six, seven, eight, nine, ten, twelve, fifteen, sixteen, eighteen, twenty, or more locked nucleic acid residues or monomers). Where the one or more encapsulated polynucleotides comprise RNA, such RNA may include, for example, mRNA, siRNA, snoRNA, microRNA, and combinations thereof.

In certain embodiments, the polynucleotides encapsulated in the pharmaceutical and liposomal compositions hereof comprise mRNA encoding, for example, a functional polypeptide, protein or enzyme, and upon being expressed (i.e., translated) by one or more target cells a functional expression product (e.g., a polypeptide, protein or enzyme) is produced, and in some instances secreted by the target cell into the peripheral circulation (e.g., plasma) of a subject. In certain embodiments, the one or more of the polynucleotides that comprise (or are otherwise loaded or encapsulated into) the compounds and pharmaceutical and liposomal compositions described herein encode a nucleic acid (e.g., a polypeptide) which is aberrantly expressed by the subject. In certain embodiments, the one or more of the encapsulated polynucleotides that comprise such compounds and liposomal or pharmaceutical compositions (e.g., a lipid nanoparticle) encode a functional protein or enzyme. For example, the polynucleotide (e.g., mRNA) may encode a protein or enzyme selected from the group consisting of erythropoietin, human growth hormone, cystic fibrosis transmembrane conductance regulator (CFTR), alpha-glucosidase, arylsulfatase A, alpha-galactosidase A, alpha-L-iduronidase, iduronate-2-sulfatase, iduronate sulfatase, N-acetylglucosamine-1-phosphate transferase, N-acetylglucosaminidase, alpha-glucosaminide acetyltransferase, N-acetylglucosamine 6-sulfatase, N-acetylgalactosamine-4-sulfatase, beta-glucosidase, galactose-6-sulfate sulfatase, beta-galactosidase, beta-glucuronidase, glucocerebrosidase, heparan sulfamidase, heparin-N-sulfatase, lysosomal acid lipase, hyaluronidase, galactocerebrosidase, ornithine transcarbamylase (OTC), carbamoyl-phosphate synthetase 1 (CPS1), argininosuccinate synthetase (ASS1), argininosuccinate lyase (ASL), and arginase 1 (ARG1).

In certain embodiments the encapsulated polynucleotide encodes an enzyme, such enzyme may be a urea cycle enzyme (e.g., ornithine transcarbamylase (OTC), carbamoyl-phosphate synthetase 1 (CPS1), argininosuccinate synthetase (ASS1), argininosuccinate lyase (ASL) or arginase 1 (ARG1)). In certain embodiments the one or more of the encapsulated polynucleotides comprises mRNA encoding an enzyme associated with a lysosomal storage disorder (e.g., the encapsulated polynucleotide is mRNA encoding one or more of the enzymes α-galactosidase A, iduronate-2-sulfatase, iduronate sulfatase, N-acetylglucosamine-1-phosphate transferase, beta-glucosidase and galactocerebrosidase).

Also contemplated herein are pharmaceutical and liposomal compositions (e.g., lipid nanoparticles) that comprise one or more of the compounds disclosed herein and one or more polynucleotides (e.g., antisense oligonucleotides), and in particular polynucleotides that comprises one or more chemical modifications. Contemplated polynucleotide modifications may include, for example, sugar modifications or substitutions (e.g., one or more of a 2'-O-alkyl modification, a locked polynucleotide (LNA) or a peptide polynucleotide (PNA)). In embodiments where the sugar modification is a 2'-O-alkyl modification, such modification may include, but are not limited to a 2'-deoxy-2'-fluoro modification, a 2'-O-methyl modification, a 2'-O-methoxyethyl modification and a 2'-deoxy modification. In certain embodiments where the modification is a nucleobase modification, such modification may be selected from the group consisting of a 5-methyl cytidine, pseudouridine, 2-thio uridine, 5-methylcytosine, isocytosine, pseudoisocytosine, 5-bromouracil, 5-propynyluracil, 6-aminopurine, 2-aminopurine, inosine, diaminopurine and 2-chloro-6-aminopurine cytosine, and combinations thereof.

In those embodiments where the polynucleotide is mRNA, such chemical modifications preferably render the mRNA more stable (e.g., more resistant to nuclease degradation) and may comprise, for example an end blocking modification of a 5' or 3' untranslated region of the mRNA. In certain embodiments, the chemical modification comprises the inclusion of a partial sequence of a CMV immediate-early 1 (IE1) gene to the 5' untranslated region of the mRNA. In other embodiments the chemical modification comprises the inclusion of a poly A tail to the 3' untranslated region of the mRNA. Also contemplated are chemical modifications that comprise the inclusion of a Cap1 structure to the 5' untranslated region of the mRNA. In still other embodiments, the chemical modification comprises the inclusion of a sequence encoding human growth hormone (hGH) to the 3' untranslated region of the mRNA.

The compounds and pharmaceutical compositions described herein may be formulated to specifically target and/or transfect one or more target cells, tissues and organs. In certain embodiments, such compounds and pharmaceutical compositions facilitate the transfection of such target cells by one or more mechanisms (e.g., fusogenic-based release and/or proton-sponge mediated disruption of the lipid-bilayer membrane of the target cells). Contemplated target cells include, for example, one or more cells selected from the group consisting of hepatocytes, hematopoietic cells, epithelial cells, endothelial cells, lung cells, bone cells, stem cells, mesenchymal cells, neural cells, cardiac cells, adipocytes, vascular smooth muscle cells, cardiomyocytes, skeletal muscle cells, beta cells, pituitary cells, synovial lining cells, ovarian cells, testicular cells, fibroblasts, B cells, T cells, reticulocytes, leukocytes, granulocytes and tumor cells.

Also disclosed are methods of treating disease (e.g., a disease associated with the aberrant expression of a gene or nucleic acid) in a subject, wherein the method comprises administering one or more of the compounds and/or pharmaceutical compositions described herein to the subject. Also contemplated are methods of transfecting one or more target cells with one or more polynucleotides, wherein the method comprises contacting the one or more target cells with the compounds or pharmaceutical composition described herein such that the one or more target cells are transfected with the one or more polynucleotides encapsulated therein.

The above discussed and many other features and attendant advantages of the present invention will become better understood by reference to the following detailed description of the invention when taken in conjunction with the accompanying examples. The various embodiments described herein are complimentary and can be combined or used together in a manner understood by the skilled person in view of the teachings contained herein.

BRIEF DESCRIPTION OF THE DRAWINGS

As shown in FIG. 1, following the intravenous injection of the second dose of GLA mRNA encapsulated in the HGT5000-based lipid nanoparticles, a substantial level of human GLA protein could be detected in mouse serum within six hours and GLA protein was further detectable forty-eight hours post-administration.

As illustrated in FIG. 2, nanogram concentrations of human GLA protein were detectable in the liver, kidney and spleen following administration of the GLA mRNA.

As illustrated in FIG. 7, significant concentrations of EPO protein were detected at six, twelve, eighteen and twenty-four hours following the intravenous administration of the EPO mRNA in both the HGT5000- and HGT5001-based lipid nanoparticles.

DETAILED DESCRIPTION

Figure 1:
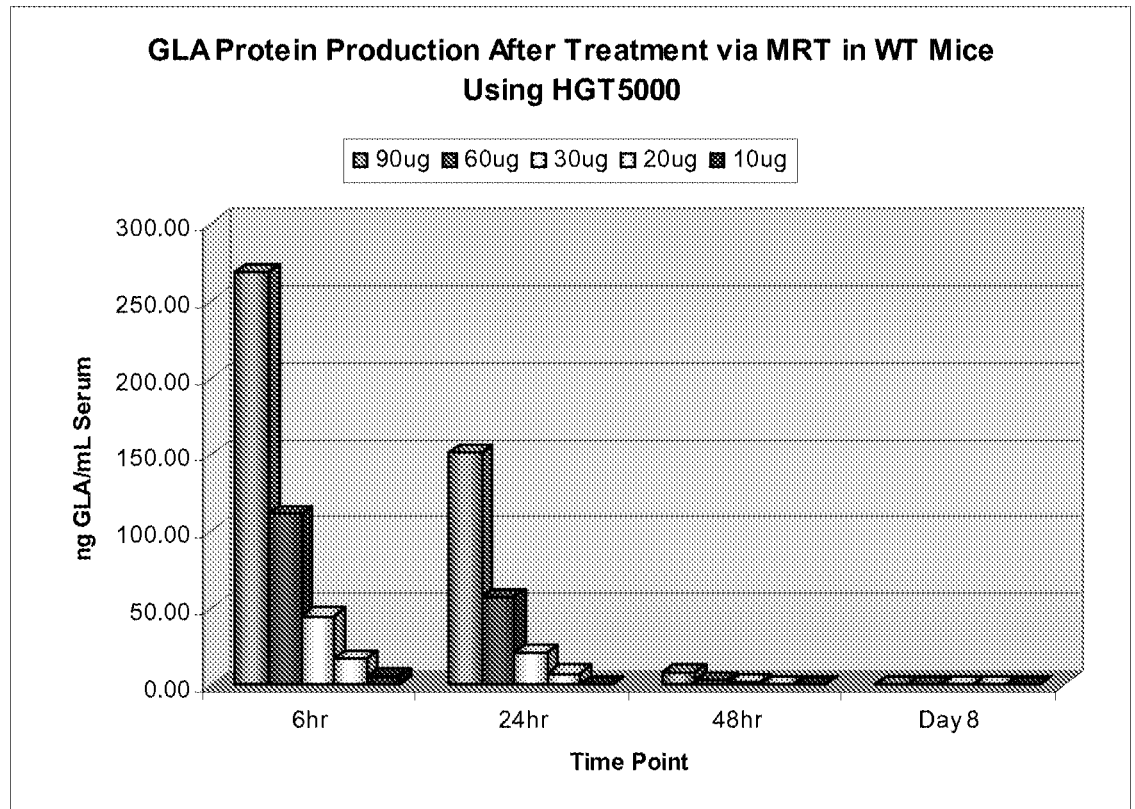
FIG. 1. illustrates the concentration of human alpha-galactosidase (GLA) protein detected in the serum of wild type (WT) mice administered two single 90 µg, 60 µg, 30 µg, 20 µg or 10 µg intravenous doses of GLA mRNA encapsulated in an HGT5000-based lipid nanoparticle over a one week period, at day one and again at day five. The serum concentrations of GLA protein were determined at six hours, twenty-four hours, forty-eight hours and seventy-two hours following the administration of the second intravenous dose. The mice were sacrificed seventy-two hours following the administration of the second intravenous dose on day eight.

Disclosed herein are novel compounds that are useful, for example, as liposomal delivery vehicles or as components of liposomal delivery vehicles. In certain embodiments, the compounds disclosed herein may be used as a liposomal composition or alternatively as component of a liposomal composition (e.g., as a lipid nanoparticle). Also disclosed are pharmaceutical compositions (e.g., lipid nanoparticles) and methods of use relating to such pharmaceutical compositions. In certain embodiments, such compounds and compositions facilitate the delivery of, for example, encapsulated materials (e.g., polynucleotides) to one or more target cells, tissues and organs.

The cationic and/or ionizable compounds disclosed herein generally comprise both a polar (hydrophilic) head-group or moiety and a non-polar (hydrophobic or lipophilic) tail-group or moiety. In certain embodiments, such polar head-group and non-polar tail-group are generally bound (e.g., bound by one or more of hydrogen-bonds, van der Waals' forces, ionic interactions and covalent bonds) to each other (e.g., a head-group and a tail-group covalently bound to each other by an optionally substituted, variably unsaturated $C_1$-$C_{10}$ alkyl or alkenyl). In certain embodiments, the head-group or moiety is hydrophilic (e.g., a hydrophilic head-group comprising an optionally-substituted alkyl amino). As used herein, the term "hydrophilic" is used to indicate in qualitative terms that a functional group is water-preferring, and typically such groups are water-soluble. For example, disclosed herein are compounds that comprise a variably unsaturated alkyl functional group bound to one or more hydrophilic groups (e.g., a hydrophilic head-group), wherein such hydrophilic groups comprise an amino group or an optionally-substituted alkyl amino group.

In certain embodiments, the selected hydrophilic functional group or moiety may alter or otherwise impart properties to the compound or to the liposomal composition of which such compound is a component (e.g., by improving the transfection efficiencies of a lipid nanoparticle of which the compound is a component). For example, the incorporation of amino group as a hydrophilic head-group in the compounds disclosed herein may promote the fusogenicity of such compound (or of the liposomal composition of which such compound is a component) with the cell membrane of one or more target cells, thereby enhancing, for example, the transfection efficiencies of such compound.

Similarly, the incorporation of one or more alkyl amino groups or moieties into the disclosed compounds (e.g., as a head-group) may further promote disruption of the endosomal/lysosomal membrane by exploiting the fusogenicity of such amino groups. This is based not only on the pKa of the amino group of the composition, but also on the ability of the amino group to undergo a hexagonal phase transition and fuse with the vesicle membrane. (Koltover, et al. *Science* (1998) 281: 78-81.) The result is believed to promote the disruption of the vesicle membrane and release of the lipid nanoparticle contents.

Similarly, in certain embodiments the incorporation of, for example, a positively charged or ionizable hydrophilic head-group in the compounds disclosed herein may serve to promote endosomal or lysosomal release of, for example, contents that are encapsulated in a liposomal composition (e.g., lipid nanoparticle) of the invention. Such enhanced release may be achieved by one or both of proton-sponge mediated disruption mechanism and/or an enhanced fusogenicity mechanism. The proton-sponge mechanism is based on the ability of a compound, and in particular a functional moiety or group of the compound, to buffer the acidification of the endosome. This may be manipulated or otherwise controlled by the pKa of the compound or of one or more of the functional groups comprising such compound (e.g., amino). Such endosomal disruption properties in turn promote osmotic swelling and the disruption of the liposomal membrane, followed by the transfection or intracellular release of the polynucleotide materials loaded or encapsulated therein into the target cell.

The lipid compounds disclosed herein may generally comprise one or more cationic and/or ionizable functional head-groups, such as an amine functional group having one or more alkyl or aryl substituents. In certain embodiments the lipid compounds disclosed herein may comprise a cationic ionizable amino functional head-group to which is bound (e.g., covalently bound) a hydrophobic functional groups, substituents or moieties (e.g., an $R_1$ group and a $R_2$ group, wherein both $R_1$ and $R_2$ are independently selected from the group consisting of hydrogen and $C_1$-$C_{10}$ alkyls). In certain embodiments, such hydrophilic and hydrophobic functional groups are bound (e.g., covalently bound) to each other by way of an intermediary group (e.g., an alkyl or a variably unsaturated alkenyl).

The compounds described herein (e.g., HGT5000, HGT5001 and HGT5002), are also characterized by their reduced toxicity, in particular relative to traditional lipids and cationic lipids such as C12-200. Accordingly, one or more of the compounds disclosed herein may be used in lieu of one or more traditional lipids that are characterized as being toxic in the amounts necessary to deliver an effective amount of one or more agents to target cells and tissues. For example, in some embodiments, pharmaceutical and liposomal compositions may be prepared such that they comprise one or more of the ionizable cationic lipid compounds disclosed herein (e.g., HGT5000, HGT5001, and/or HGT5002) as a means of reducing or otherwise eliminating the toxicity associated with the liposomal composition. The cationic ionizable compounds or lipids (e.g., HGT5000, HGT5001 and/or HGT5002) may be used as the sole cationic lipid in one or more of the pharmaceutical and liposomal compositions described herein (e.g., lipid nanoparticles), or alternatively may be combined with traditional cationic lipids (e.g., LIPOFECTIN or LIPOFECTAMINE), non-cationic lipids, PEG-modified lipids and/or helper lipids. In certain embodiments, the compounds described herein, or alternatively the total cationic lipid component of the pharmaceutical and liposomal compositions may comprise a molar ratio of about 1% to about 90%, about 2% to about 70%, about 5% to about 50%, about 10% to about 40% of the total lipid present in such pharmaceutical or liposomal composition (e.g., a lipid nanoparticle), or preferably about 20% to about 70% of the total lipid present in such pharmaceutical or liposomal composition (e.g., a lipid nanoparticle). Additionally, combining or enriching liposomal vehicles with the cationic ionizable lipid compounds disclosed herein allows a corresponding reduction in the concentration of the other lipid components of the liposomal vehicle, thereby providing a means of reducing or otherwise mitigating the toxicity associated with other cationic lipids (e.g., C12-200) that may also be present in the liposomal vehicle.

In certain embodiments, at least one of the functional groups of moieties that comprise the compounds disclosed herein is hydrophobic in nature (e.g., a hydrophobic tail-group comprising a naturally-occurring lipid such as cholesterol). As used herein, the term "hydrophobic" is used to indicate in qualitative terms that a functional group is water-avoiding, and typically such groups are not water soluble. For example, in certain embodiments the hydrophobic or lipophilic tail-group (e.g., one or more of an $L_1$ group and an $L_2$ group) of the compounds disclosed herein may comprise one or more non-polar groups such as cholesterol or an optionally substituted, variably saturated or unsaturated alkyl or alkenyl (e.g., an optionally substituted octadeca-9,12-diene).

In certain embodiments, the compounds disclosed herein comprise, for example, at least one hydrophilic head-group and at least one hydrophobic tail-group, each bound to each other by, for example an optionally substituted, variably saturated or unsaturated alkyl or alkenyl, thereby rendering such compounds amphiphilic. As used herein to describe a compound or composition, the term "amphiphilic" means the ability to dissolve in both polar (e.g., water) and non-polar (e.g., lipid) environments. For example, in certain embodiments, the compounds disclosed herein comprise at least one lipophilic tail-group (e.g., cholesterol or a $C_6$-$C_{20}$ alkyl or alkenyl) and at least one hydrophilic head-group (e.g., an alkyl amino), each bound to an intermediary $C_1$-$C_{20}$ alkyl or alkenyl group (e.g., hexane or hexene).

It should be noted that the terms "head-group" and "tail-group" as used describe the compounds of the present invention, and in particular functional groups that comprise such compounds, are used for ease of reference to describe the orientation of one or more functional groups relative to other functional groups. For example, in certain embodiments a hydrophilic head-group (e.g., amino) is bound (e.g., by one or more of hydrogen-bonds, van der Waals' forces, ionic interactions and covalent bonds) to an alkyl or alkenyl functional group (e.g., hex-1-ene), which in turn is bound to a hydrophobic tail-group (e.g., cholesterol or a $C_6$-$C_{20}$ variably unsaturated alkenyl).

Also disclosed herein are compounds having the structure of formula (I):

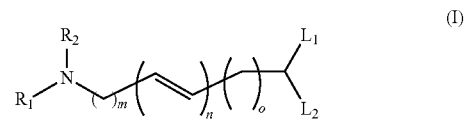

wherein $R_1$ and $R_2$ are each independently selected from the group consisting of hydrogen, an optionally substituted, variably saturated or unsaturated $C_1$-$C_{20}$ alkyl or alkenyl and an optionally substituted, variably saturated or unsaturated $C_6$-$C_{20}$ acyl; wherein $L_1$ and $L_2$ are each independently selected from the group consisting of hydrogen, an optionally substituted $C_1$-$C_{30}$ alkyl, an optionally substituted variably unsaturated $C_1$-$C_{30}$ alkenyl, and an optionally substituted $C_1$-$C_{30}$ alkynyl; wherein m and o are each independently selected from the group consisting of zero and any positive integer (e.g., where m is three); and wherein n is zero or any positive integer (e.g., where n is one).

In certain embodiments, the compound has the structure of formula (I), wherein $R_1$ and $R_2$ are each methyl. In such embodiment, the polar cationic head-group of the compound comprises an ionizable dimethyl amino group.

In some embodiments, the compound has the structure of formula (I), wherein $L_1$ and $L_2$ are each an optionally substituted, polyunsaturated $C_6$-$C_{20}$ alkenyl. For example, contemplated are compounds wherein $L_1$ and $L_2$ are each an optionally substituted polyunsaturated $C_{18}$ alkenyl. In other embodiments, $L_1$ and $L_2$ are each an unsubstituted, polyunsaturated $C_{18}$ alkenyl. In yet other embodiments, $L_1$ and $L_2$ are each an optionally substituted octadeca-9,12-diene (or octadec-6,9-diene). In still other embodiments, $L_1$ is hydrogen and $L_2$ is cholesterol. In certain embodiments, each of $L_1$ and $L_2$ are (9Z,12Z)-octadeca-9,12-dien. In certain embodiments, each of $L_1$ and $L_2$ are octadec-6,9-diene.

In certain embodiments disclosed herein, the present inventions relate to a compound having the structure of formula (I), wherein o is zero. Alternatively, in other embodiments, o is a positive integer (e.g., one, two, three, four, five, six, seven, eight, nine, ten, eleven, twelve, thirteen, fourteen, fifteen, sixteen, seventeen, eighteen, nineteen, twenty, or more).

In certain embodiments disclosed herein, the present inventions relate to a compound having the structure of formula (I), wherein m is a positive integer (e.g., one, two, three, four, five, six, seven, eight, nine, ten, eleven, twelve, thirteen, fourteen, fifteen, sixteen, seventeen, eighteen, nineteen, twenty, or more). In some particular embodiments, the present inventions relate to a compound having the structure of formula (I), wherein m is four. In some particular embodiments, the present inventions relate to a compound having the structure of formula (I), wherein m is three.

Also disclosed herein are compounds having the structure of formula (I), wherein n is a positive integer (e.g., one, two, three, four, five, six, seven, eight, nine, ten, eleven, twelve, thirteen, fourteen, fifteen, sixteen, seventeen, eighteen, nineteen, twenty, or more). In other particular embodiments, the present inventions relate to a compound having the structure of formula (I), wherein n is zero.

In certain embodiments, m and o are independently selected from the group consisting of zero, one (such that the alkyl is ethyl), two (such that the alkyl is methyl), three (such that the alkyl is, for example, propyl or iso-propyl), four (such that the alkyl is, for example, butyl, iso-butyl, sec-butyl or ter-butyl), five (such that the alkyl is, for example, pentane), six (such that the alkyl is, for example, hexane), seven (such that the alkyl is, for example, heptane), eight (such that the alkyl is, for example, octane), nine (n such that the alkyl is, for example, nonane) or ten (such that the alkyl is, for example, decane).

In some particular embodiments, the present invention relates to a compound having the structure of formula (I), wherein $R_1$ and $R_2$ are each methyl; wherein $L_1$ and $L_2$ are each octadeca-9,12-diene (or octadec-6,9-diene); wherein m is four; wherein n is zero; and wherein o is one. For example, in certain embodiments, the present invention relates to the compound (15Z,18Z)—N,N-dimethyl-6-(9Z,12Z)-octadeca-9,12-dien-1-yl)tetracosa-15,18-dien-1-amine, having the structure of formula (II), (referred to herein as "HGT5000").

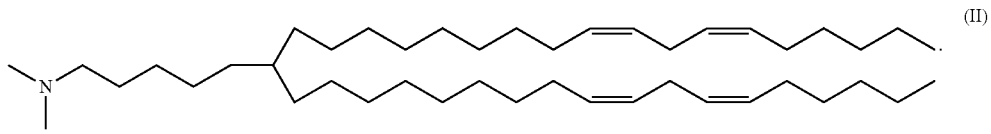 [SMILES: CCCCC/C=C\C/C=C\CCCCCCCCC(CCCCCCCC/C=C\C/C=C\CCCCC)CCCCCN(C)C]

(II)

In some particular embodiments, the present invention relates to a compound having the structure of formula (I), wherein $R_1$ and $R_2$ are each methyl; wherein $L_1$ and $L_2$ are each octadeca-9,12-diene (or octadec-6,9-diene); wherein m is 3; wherein n is one; and wherein o is zero. For example, in certain embodiments, the present invention relates to the compound (15Z,18Z)—N,N-dimethyl-6-((9Z,12Z)-octadeca-9,12-dien-1-yl)tetracosa-4,15,18-trien-1-amine, having the structure of formula (III), (referred to herein as "HGT5001").

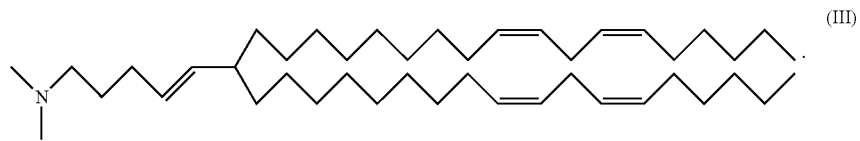 [SMILES: CCCCC/C=C\C/C=C\CCCCCCCCC(/C=C/CCCN(C)C)CCCCCCCC/C=C\C/C=C\CCCCC]

(III)

It should be understood that in those embodiments disclosed herein where n is one, such compounds may be a cis isomer, a trans isomer or alternatively a racemic mixture thereof. For example, in certain embodiments where n is one, n is a cis isomer, as represented by a compound having the structure of formula (IV):

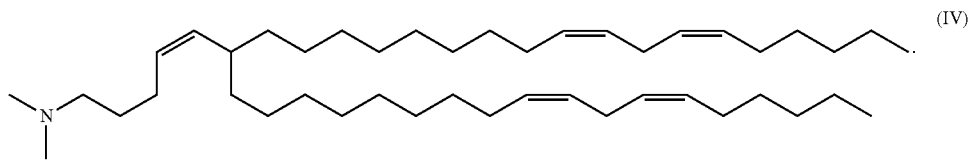 [SMILES: CCCCC/C=C\C/C=C\CCCCCCCCC(/C=C\CCCN(C)C)CCCCCCCC/C=C\C/C=C\CCCCC]

(IV)

Alternatively, in other embodiments where n is one, n is a trans isomer, as represented by a compound having the structure of formula (V):

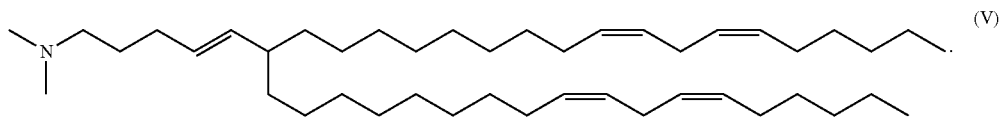

(V)

Also disclosed are compounds having the structure of formula (VI):

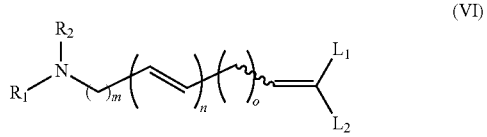

(VI)

wherein $R_1$ and $R_2$ are each independently selected from the group consisting of hydrogen, an optionally substituted, variably saturated or unsaturated $C_1$-$C_{20}$ alkyl or alkenyl and an optionally substituted, variably saturated or unsaturated $C_6$-$C_{20}$ acyl; wherein $L_1$ and $L_2$ are each independently selected from the group consisting of hydrogen, an optionally substituted $C_1$-$C_{30}$ alkyl, an optionally substituted variably unsaturated $C_1$-$C_{30}$ alkenyl, and an optionally substituted $C_1$-$C_{30}$ alkynyl; and wherein m, n and o are each independently selected from the group consisting of zero and any positive integer.

In some particular embodiments, the present inventions are directed to a compound having the structure of formula (VI), wherein $R_1$ and $R_2$ are each methyl. In other embodiments, the present inventions are directed to a compound having the structure of formula (VI), wherein $R_1$ and $R_2$ are each independently selected from the group consisting of hydrogen and methyl.

Also contemplated are compounds having the structure of formula (VI), wherein $L_1$ and $L_2$ are each an optionally substituted, polyunsaturated $C_6$-$C_{20}$ alkenyl (e.g., where $L_1$ and $L_2$ are each an optionally substituted polyunsaturated $C_{18}$ alkenyl or where $L_1$ and $L_2$ are each an unsubstituted, polyunsaturated $C_{18}$ alkenyl). In certain embodiments, disclosed herein, $L_1$ and $L_2$ are each an optionally substituted octadeca-9,12-diene (or octadec-6,9-diene). In other embodiments $L_1$ is hydrogen and $L_2$ is cholesterol.

In certain embodiments disclosed herein, the present inventions relate to a compound having the structure of formula (VI), wherein m is a positive integer (e.g., one, two, three, four, five, six, seven, eight, nine, ten, eleven, twelve, thirteen, fourteen, fifteen, sixteen, seventeen, eighteen, nineteen, twenty, or more). In some particular embodiments, the present inventions relate to a compound having the structure of formula (VI), wherein m is four. In certain embodiments, the present inventions relate to a compound having the structure of formula (VI), wherein m is at least five (e.g., where m is five, six, seven, eight, nine, ten, eleven, twelve, thirteen, fourteen, fifteen, sixteen, seventeen, eighteen, nineteen, twenty or more).

Also disclosed herein are compounds having the structure of formula (VI), wherein n is a positive integer (e.g., one, two, three, four, five, six, seven, eight, nine, ten, eleven, twelve, thirteen, fourteen, fifteen, sixteen, seventeen, eighteen, nineteen, twenty, or more). In other particular embodiments, the present inventions relate to a compound having the structure of formula (VI), wherein n is zero.

In certain embodiments disclosed herein, the present inventions are directed to compounds having the structure of formula (VI), wherein o is a positive integer (e.g., one, two, three, four, five, six, seven, eight, nine, ten, eleven, twelve, thirteen, fourteen, fifteen, sixteen, seventeen, eighteen, nineteen, twenty, or more). In certain embodiments, the present inventions relate to a compound having the structure of formula (VI), wherein o is at least five (e.g., where o is five, six, seven, eight, nine, ten, eleven, twelve, thirteen, fourteen, fifteen, sixteen, seventeen, eighteen, nineteen, twenty or more). Alternatively, in other particular embodiments, the present inventions relate to compounds having the structure of formula (VI), wherein o is zero.

Also contemplated are compounds having the structure of formula (VI), wherein $R_1$ and $R_2$ are each methyl; wherein $L_1$ and $L_2$ are each octadeca-9,12-diene (or octadec-6,9-diene); wherein m is 4; and wherein both n and o are zero. For example, in certain embodiments, the present invention relates to the compound (15Z,18Z)—N,N-dimethyl-6-((9Z,12Z)-octadeca-9,12-dien-1-yl)tetracosa-5,15,18-trien-1-amine having the structure of formula (VII), (referred to herein as "HGT5002"):

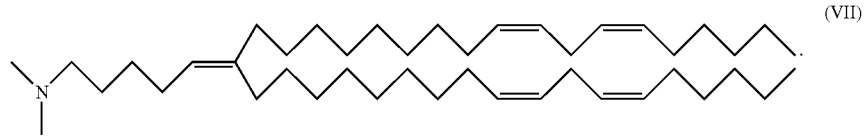 [SMILES: CCCCC/C=C\C/C=C\CCCCCCCCC(=CCCCCN(C)C)CCCCCCCC/C=C\C/C=C\CCCCC]

Also disclosed herein are compounds having the structure of formula (VIII):

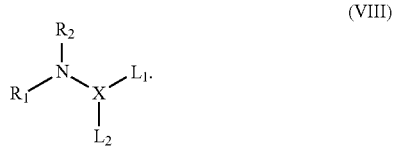

wherein $R_1$ and $R_2$ are each independently selected from the group consisting of an optionally substituted, variably saturated or unsaturated $C_1$-$C_{20}$ alkyl or alkenyl and an optionally substituted, variably saturated or unsaturated $C_6$-$C_{20}$ acyl; wherein $L_1$ and $L_2$ are each independently selected from the group consisting of an optionally substituted $C_1$-$C_{30}$ alkyl, an optionally substituted variably unsaturated $C_1$-$C_{30}$ alkenyl, and an optionally substituted $C_1$-$C_{30}$ alkynyl; and wherein x is selected from the group consisting of a $C_1$-$C_{20}$ alkyl and a variably unsaturated $C_1$-$C_{20}$ alkenyl.

In certain embodiments, the disclosed compounds have the structure of formula (VIII), wherein $R_1$ and $R_2$ are each methyl. In other embodiments, the disclosed compounds have the structure of formula (VIII), wherein $R_1$ and $R_2$ are independently selected from the group consisting of hydrogen and a $C_1$-$C_6$ alkyl.

In other embodiments, the present invention relates to compounds having the structure of formula (VIII), wherein $L_1$ and $L_2$ are each an unsubstituted, polyunsaturated $C_{18}$ alkenyl. For example, in certain embodiments, $L_1$ and $L_2$ are each an optionally substituted octadeca-9,12-diene (e.g., $L_1$ and $L_2$ are each an unsubstituted octadeca-9,12-diene or octadec-6,9-diene). In certain other embodiments, $L_1$ is hydrogen and $L_2$ is cholesterol.

In certain embodiments, the disclosed compounds have the structure of formula (VIII), wherein x is a $C_6$ alkenyl. In other embodiments, the disclosed compounds have the structure of formula (VIII), wherein x is hexane. In yet other embodiments, the disclosed compounds have the structure of formula (VIII), wherein x is hex-1-ene. In still other embodiments, the disclosed compounds have the structure of formula (VIII), wherein x is hex-2-ene. In certain embodiments, x is not hexane. In other embodiments, the disclosed compounds have the structure of formula (VIII), wherein x is a $C_6$-$C_{10}$ alkenyl or a $C_6$-$C_{10}$ alkyl.

In one particular embodiment, the present invention relates to a compound having the structure of formula (VIII), wherein $R_1$ and $R_2$ are each methyl; wherein $L_1$ and $L_2$ are each octadeca-9,12-diene; and wherein x is hexane. In another particular embodiment, the present invention relates to a compound having the structure of formula (VIII), wherein $R_1$ and $R_2$ are each methyl; wherein $L_1$ and $L_2$ are each octadeca-9,12-diene (or octadec-6,9-diene); and wherein x is hex-1-ene. In still another particular embodiment, the present invention relates to a compound having the structure of formula (VIII), wherein $R_1$ and $R_2$ are each methyl; wherein $L_1$ and $L_2$ are each octadeca-9,12-diene (or octadec-6,9-diene); and wherein x is hex-2-ene.

As used herein, the term "alkyl" refers to both straight and branched chain $C_1$-$C_{40}$ hydrocarbons (e.g., $C_6$-$C_{20}$ hydrocarbons), and include both saturated and unsaturated hydrocarbons. In certain embodiments, the alkyl may comprise one or more cyclic alkyls and/or one or more heteroatoms such as oxygen, nitrogen, or sulfur and may optionally be substituted with substituents (e.g., one or more of alkyl, halo, alkoxyl, hydroxy, amino, aryl, ether, ester or amide). In certain embodiments, a contemplated alkyl hydrophobic tail-group comprises (9Z,12Z)-octadeca-9,12-dien. In certain embodiments, a contemplated alkyl hydrophobic tail-group comprises (or octadec-6,9-diene. The use of designations such as, for example, "$C_6$-$C_{20}$" is intended to refer to an alkyl (e.g., straight or branched chain and inclusive of alkenes and alkyls) having the recited range carbon atoms.

As used herein, the term "aryl" refers to aromatic groups (e.g., monocyclic, bicyclic and tricyclic structures) containing six to ten carbons in the ring portion. The aryl groups may be optionally substituted through available carbon atoms and in certain embodiments may include one or more heteroatoms such as oxygen, nitrogen or sulfur.

It should be understood that in those embodiments described herein where the compounds have one or more asymmetric or chiral molecules (e.g., one or more unsaturated carbon-carbon double bonds), both the cis (Z) and trans (E) isomers are within the scope of this invention.

The compounds described herein may be used to construct liposomal compositions that facilitate or enhance the delivery and release of encapsulated materials (e.g., one or more therapeutic polynucleotides) to one or more target cells (e.g., by permeating or fusing with the lipid membranes of such target cells). For example, when a liposomal composition (e.g., a lipid nanoparticle) comprises or is otherwise enriched with one or more of the compounds disclosed herein, the phase transition in the lipid bilayer of the one or more target cells may facilitate the delivery of the encapsulated materials (e.g., one or more therapeutic polynucleotides encapsulated in a lipid nanoparticle) into the one or more target cells. Similarly, in certain embodiments the compounds disclosed herein may be used to prepare liposomal vehicles that are characterized by their reduced toxicity in vivo. In certain embodiments, the reduced toxicity is a function of the high transfection efficiencies associated with the compositions disclosed herein, such that a reduced quantity of such composition may administered to the subject to achieve a desired therapeutic response or outcome.

In certain embodiments the compounds described herein are characterized as having one or more properties that afford such compounds advantages relative to other similarly classified lipids. For example, in certain embodiments, the compounds disclosed herein allow for the control and tailoring of the properties of liposomal compositions (e.g., lipid nanoparticles) of which they are a component. In particular, the compounds disclosed herein may be characterized by enhanced transfection efficiencies and their ability to provoke specific biological outcomes. Such outcomes may include, for example enhanced cellular uptake, endosomal/lysosomal disruption capabilities and/or promoting the release of encapsulated materials (e.g., polynucleotides) intracellularly.

In certain embodiments the compounds described herein (and the pharmaceutical and liposomal compositions comprising such compounds) employ a multifunctional strategy to facilitate the delivery of encapsulated materials (e.g., one or more polynucleotides) to, and subsequent transfection of one or more target cells. For example, in certain embodiments the compounds described herein (and the pharmaceutical and liposomal compositions comprising such compounds) are characterized as having one or more of receptor-mediated endocytosis, clathrin-mediated and caveolae-mediated endocytosis, phagocytosis and macropinocytosis, fusogenicity, endosomal or lysosomal disruption and/or releasable properties that afford such compounds advantages relative other similarly classified lipids.

In certain embodiments the compounds and the pharmaceutical and liposomal compositions of which such compounds are a component (e.g., lipid nanoparticles) exhibit an enhanced (e.g., increased) ability to transfect one or more target cells. Accordingly, also provided herein are methods of transfecting one or more target cells. Such methods generally comprise the step of contacting the one or more target cells with the compounds and/or pharmaceutical compositions disclosed herein (e.g., an HGT5000-, HGT5001- and/or HGT5002-based lipid nanoparticle encapsulating one or more polynucleotides) such that the one or more target cells are transfected with the materials encapsulated therein (e.g., one or more polynucleotides). As used herein, the terms "transfect" or "transfection" refer to the intracellular introduction of one or more encapsulated materials (e.g., nucleic acids and/or polynucleotides) into a cell, or preferably into a target cell. The introduced polynucleotide may be stably or transiently maintained in the target cell. The term "transfection efficiency" refers to the relative amount of such encapsulated material (e.g., polynucleotides) up-taken by, introduced into and/or expressed by the target cell which is subject to transfection. In practice, transfection efficiency may be estimated by the amount of a reporter polynucleotide product produced by the target cells following transfection. In certain embodiments, the compounds and pharmaceutical compositions described herein demonstrate high transfection efficiencies thereby improving the likelihood that appropriate dosages of the encapsulated materials (e.g., one or more polynucleotides) will be delivered to the site of pathology and subsequently expressed, while at the same time minimizing potential systemic adverse effects or toxicity associated with the compound or their encapsulated contents.

A wide range of materials that can exert pharmaceutical or therapeutic effects can be delivered to target cells using the compounds, compositions and methods of the present invention. Accordingly, the compounds and pharmaceutical and liposomal compositions described herein may be used to encapsulate any materials suitable for intracellular delivery. In certain embodiments, such encapsulated materials are capable of conferring a therapeutic or diagnostic benefit upon the cells into which such materials are delivered, and may include any drugs, biologics and/or diagnostics. The materials can be organic or inorganic. Organic molecules can be peptides, proteins, carbohydrates, lipids, sterols, nucleic acids (including peptide nucleic acids), or any combination thereof. In certain embodiments, the pharmaceutical and liposomal compositions described herein can comprise or otherwise encapsulate more than one type of material, for example, two or more different polynucleotide sequences encoding a protein, an enzyme and/or a steroid. In certain embodiments, the encapsulated materials are one or more polynucleotides and nucleic acids.

As used herein, the terms "polynucleotide" and "nucleic acid" are used interchangeably to refer to genetic material (e.g., DNA or RNA), and when such terms are used with respect to the compounds and compositions described herein (e.g., lipid nanoparticles) generally refer to the genetic material encapsulated by such compounds and compositions (e.g., lipid nanoparticles). In some embodiments, the polynucleotide is RNA. Suitable RNA includes mRNA, siRNA, miRNA, snRNA and snoRNA. Contemplated polynucleotides also include large intergenic non-coding RNA (lincRNA), which generally does not encode proteins, but rather function, for example, in immune signaling, stem cell biology and the development of disease. (See, e.g., Guttman, et al., 458: 223-227 (2009); and Ng, et al., Nature Genetics 42: 1035-1036 (2010), the contents of which are incorporated herein by reference). In certain embodiments, the polynucleotides encapsulated by the compounds or pharmaceutical and liposomal compositions of the invention include RNA or stabilized RNA encoding a protein or enzyme (e.g., mRNA encoding α-galactosidase A or arylsulfatase A). The present invention contemplates the use of such polynucleotides (and in particular RNA or stabilized RNA) as a therapeutic that is capable of being expressed by target cells to thereby facilitate the production (and in certain instances the excretion) of a functional enzyme or protein by such target cells as disclosed for example, in International Application No. PCT/US2010/058457 and in U.S. Provisional Application No. 61/494,881, filed Jun. 8, 2011, the teachings of which are both incorporated herein by reference in their entirety. For example, in certain embodiments, upon the expression of one or more polynucleotides by target cells the production of a functional enzyme or protein in which a subject is deficient (e.g., a urea cycle enzyme or an enzyme associated with a lysosomal storage disorder) may be observed. The term "functional", as used herein to qualify a protein or enzyme, means that the protein or enzyme has biological activity, or alternatively is able to perform the same, or a similar function as the native or normally-functioning protein or enzyme.

In certain embodiments, the compounds and the pharmaceutical and liposomal compositions described herein are formulated as a blended formulation or composition. For example, in one embodiment, a pharmaceutical composition comprises a blended formulation comprising a 3:1 ratio of a first lipid nanoparticle comprising HGT5000 and a second lipid nanoparticle comprising HGT5001. Accordingly, also provided herein are blended pharmaceutical compositions and related methods for modulating the expression of a polynucleotide in one or more target cells and tissues, as disclosed for example, in U.S. Provisional Application No. 61/494,714, filed Jun. 8, 2011, the teachings of which are incorporated herein by reference in their entirety. Also contemplated are methods for modulating (e.g., increasing or synergistically increasing) the production and/or secretion of, for example, one or more functional polypeptides, proteins or enzymes that are encoded by one or more polynucleotides (e.g., mRNA) encapsulated in such blended pharmaceutical compositions by one or more target cells.

In the context of the present invention the term "expression" is used in its broadest sense to refer to either the transcription of a specific gene or polynucleotide into at least one mRNA transcript, or the translation of at least one mRNA or polynucleotide into a protein or enzyme. For example, in certain embodiments the compounds and the pharmaceutical or liposomal compositions described herein comprise a polynucleotide (e.g., mRNA) which encodes a functional protein or enzyme. In the context of such mRNA polynucleotides, the term expression refers to the translation of such mRNA (e.g., by the target cells) to produce the polypeptide or protein encoded thereby.

In certain embodiments, the compounds and pharmaceutical compositions provided herein are capable of modulating the expression of aberrantly expressed nucleic acids and polynucleotides in one or more target cells and tissues. Accordingly, also provided herein are methods of treating disease in a subject by administering an effective amount of the compounds and/or the pharmaceutical or liposomal compositions described herein to the subject. In certain embodiments, such methods may enhance (e.g., increase) the expression of a polynucleotide and/or increase the production and secretion of a functional polypeptide product in one or more target cells and tissues (e.g., hepatocytes). In some embodiments, the targeted cells or tissues aberrantly express the polynucleotide encapsulated by one or more of the compounds or pharmaceutical and liposomal compositions (e.g., lipid nanoparticles) described herein. Also provided herein are methods of increasing the expression of one or more polynucleotides (e.g., mRNA) in one or more target cells, tissues and organs (e.g., the lungs, heart, spleen, liver and/or kidneys). Generally, such methods comprise contacting the target cells with one or more compounds and/or pharmaceutical or liposomal compositions that comprise or otherwise encapsulate one or more polynucleotides.

In certain embodiments, the compounds disclosed herein may be used as a liposome or as a component of a liposome. Specifically, in certain embodiments the compounds disclosed herein may be used as a lipid (e.g., cationic lipid) component of a liposomal composition (e.g., a lipid nanoparticle). Such liposomes may be used to encapsulate materials and facilitate the delivery of such materials to one or more target cells, tissues and organs. As used herein, the term "liposome" generally refers to a vesicle composed of lipids (e.g., amphiphilic lipids) arranged in one or more spherical bilayer or bilayers. In certain embodiments, the liposome is a lipid nanoparticle (e.g., a lipid nanoparticle comprising one or more of the cationic lipid compounds disclosed herein). Such liposomes may be unilamellar or multilamellar vesicles which have a membrane formed from a lipophilic material and an aqueous interior that contains the encapsulated materials (e.g., polynucleotides) to be delivered to one or more target cells, tissues and organs. In certain embodiments, the pharmaceutical and liposomal compositions described herein comprise one or more lipid nanoparticles. Contemplated liposomes include lipid nanoparticles. Examples of suitable lipids (e.g., cationic lipids) that may be used to form the liposomes and lipid nanoparticles contemplated hereby include one or more of the compounds disclosed herein (e.g., HGT5000, HGT5001, and/or HGT5002). Such liposomes and lipid nanoparticles may also comprise additional cationic lipids such as C12-200, DLin-KC2-DMA, DOPE, DMG-PEG-2000, non-cationic lipids, cholesterol-based lipids, helper lipids, PEG-modified lipids, as well as the phosphatidyl compounds (e.g., phosphatidylglycerol, phosphatidylcholine, phosphatidylserine, phosphatidylethanolamine, sphingolipids, cerebrosides, and gangliosides) and combinations or mixtures of the forgoing.

Several cationic lipids have been described in the literature, many of which are commercially available. In certain embodiments, such cationic lipids are included in the pharmaceutical or liposomal compositions described herein in addition to one or more of the compounds or lipids disclosed herein (e.g., HGT5000). In some embodiments, the cationic lipid N-[1-(2,3-dioleyloxy)propyl]-N,N,N-trimethylammonium chloride or "DOTMA" is used. (Felgner et al. (Proc. Nat'l Acad. Sci. 84, 7413 (1987); U.S. Pat. No. 4,897,355). DOTMA can be formulated alone or can be combined with dioleoylphosphatidylethanolamine or "DOPE" or other cationic or non-cationic lipids into a lipid nanoparticle. Other suitable cationic lipids include, for example C12-200, 5-carboxyspermylglycinedioctadecylamide or "DOGS," 2,3-dioleyloxy-N-[2(spermine-carboxamido)ethyl]-N,N-dimethyl-1-propanaminium or "DOSPA" (Behr et al. Proc. Nat.'l Acad. Sci. 86, 6982 (1989); U.S. Pat. Nos. 5,171,678; 5,334,761), 1,2-Dioleoyl-3-Dimethylammonium-Propane or "DODAP", 1,2-Dioleoyl-3-Trimethylammonium-Propane or "DOTAP". Contemplated cationic lipids also include 1,2-distearyloxy-N,N-dimethyl-3-aminopropane or "DSDMA", 1,2-dioleyloxy-N,N-dimethyl-3-aminopropane or "DODMA", 1,2-dilinoleyloxy-N,N-dimethyl-3-aminopropane or "DLinDMA", 1,2-dilinolenyloxy-N,N-dimethyl-3-aminopropane or "DLenDMA", N-dioleyl-N,N-dimethylammonium chloride or "DODAC", N,N-distearyl-N,N-dimethylammonium bromide or "DDAB", N-(1,2-dimyristyloxyprop-3-yl)-N,N-dimethyl-N-hydroxyethyl ammonium bromide or "DMRIE", 3-dimethylamino-2-(cholest-5-en-3-beta-oxybutan-4-oxy)-1-(cis,cis-9,12-octadecadienoxy)propane or "CLinDMA", 2-[5'-(cholest-5-en-3-beta-oxy)-3'-oxapentoxy)-3-dimethyl-1-(cis,cis-9',1-2'-octadecadienoxy)propane or "CpLinDMA", N,N-dimethyl-3,4-dioleyloxybenzylamine or "DMOBA", 1,2-N,N'-dioleylcarbamyl-3-dimethylaminopropane or "DOcarbDAP", 2,3-Dilinoleoyloxy-N,N-dimethylpropylamine or "DLinDAP", 1,2-N,N'-Dilinoleylcarbamyl-3-dimethylaminopropane or "DLincarbDAP", 1,2-Dilinoleoylcarbamyl-3-dimethylaminopropane or "DLinCDAP", 2,2-dilinoleyl-4-dimethylaminomethyl-[1,3]-dioxolane or "DLin-K-DMA", 2,2-dilinoleyl-4-dimethylaminoethyl-[1,3]-dioxolane or "DLin-K-XTC2-DMA", or mixtures thereof (Heyes, J., et al., J Controlled Release 107: 276-287 (2005); Morrissey, D V., et al., Nat. Biotechnol. 23(8): 1003-1007 (2005); PCT Publication WO2005/121348A1). The use of cholesterol-based cationic lipids to formulate the compositions (e.g., lipid nanoparticles) is also contemplated by the present invention. Such cholesterol-based cationic lipids can be used, either alone or in combination with other cationic or non-cationic lipids. Suitable cholesterol-based cationic lipids include, for example, DC-Chol (N,N-dimethyl-N-ethylcarboxamidocholesterol), 1,4-bis(3-N-oleylamino-propyl)piperazine (Gao, et al. Biochem. Biophys. Res. Comm. 179, 280 (1991); Wolf et al. BioTechniques 23, 139 (1997); U.S. Pat. No. 5,744,335).

In addition, several reagents are commercially available to enhance transfection efficacy. Suitable examples include LIPOFECTIN (DOTMA:DOPE) (Invitrogen, Carlsbad, Calif.), LIPOFECTAMINE (DOSPA:DOPE) (Invitrogen), LIPOFECTAMINE2000. (Invitrogen), FUGENE, TRANSFECTAM (DOGS), and EFFECTENE. Also contemplated are cationic lipids such as the dialkylamino-based, imidazole-based, and guanidinium-based lipids. For example, also contemplated is the use of the cationic lipid (3S,10R,13R,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl 3-(1H-imidazol-4-yl)propanoate or "ICE", as disclosed in International Application No. PCT/US2010/058457, the teachings of which are incorporated herein by reference in their entirety.

The use and inclusion of polyethylene glycol (PEG)-modified phospholipids and derivatized lipids such as derivatized cerarmides (PEG-CER), including N-Octanoyl-Sphingosine-1-[Succinyl(Methoxy Polyethylene Glycol)-2000] (C8 PEG-2000 ceramide) in the liposomal and pharmaceutical compositions described herein is also contemplated, preferably in combination with one or more of the compounds and lipids disclosed herein. Contemplated PEG-modified lipids include, but are not limited to, a polyethylene glycol chain of up to 5 kDa in length covalently attached to a lipid with alkyl chain(s) of $C_6$-$C_{20}$ length. The addition of such components may prevent complex aggregation and may also provide a means for increasing circulation lifetime and increasing the delivery of the lipid-polynucleotide composition to the target tissues, (Klibanov et al. (1990) FEBS Letters, 268 (1): 235-237), or they may be selected to rapidly exchange out of the formulation in vivo (see U.S. Pat. No. 5,885,613). Particularly useful exchangeable lipids are PEG-ceramides having shorter acyl chains (e.g., C14 or C18). The PEG-modified phospholipid and derivatized lipids of the present invention may comprise a molar ratio from about 0% to about 20%, about 0.5% to about 20%, about 1% to about 15%, about 4% to about 10%, or about 2% of the total lipid present in a liposomal lipid nanoparticle.

The present invention also contemplates the use of non-cationic lipids in one or more of the pharmaceutical or liposomal compositions (e.g., lipid nanoparticles). Such non-cationic lipids are preferably used in combination with one or more of the compounds and lipids disclosed herein. As used herein, the phrase "non-cationic lipid" refers to any neutral, zwitterionic or anionic lipid. As used herein, the phrase "anionic lipid" refers to any of a number of lipid species that carry a net negative charge at a selected pH, such as physiological pH. Non-cationic lipids include, but are not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoyl-phosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), DLPE (1,2-dilauroyl-sn-glycero-3-phosphoethanolamine), DPPS (1,2-dipalmitoyl-sn-glycero-3-phospho-L-serine), 16-O-monomethyl PE, 16-O-dimethyl PE, 18-1-trans PE, 1-stearoyl-2-oleoyl-phosphatidyethanolamine (SOPE), ceramides, sphingomyelins, cholesterol, or a mixture thereof. Such non-cationic lipids may be used alone, but are preferably used in combination with other excipients, for example, one or more of the cationic lipid compounds disclosed herein (e.g., HGT5000, HGT5001, and/or HGT5002). When used in combination with a cationic lipid, the non-cationic lipid may comprise a molar ratio of 5% to about 90%, or preferably about 10% to about 70% of the total lipid present in the lipid nanoparticle.

Also contemplated is inclusion of polymers in the lipid nanoparticles that comprise the pharmaceutical or liposomal compositions described herein. Suitable polymers may include, for example, polyacrylates, polyalkycyanoacrylates, polylactide, polylactide-polyglycolide copolymers, polycaprolactones, dextran, albumin, gelatin, alginate, collagen, chitosan, cyclodextrins and polyethylenimine. Such polymers may be used alone, but are preferably used in combination with other excipients, for example, one or more of the cationic lipid compounds disclosed herein (e.g., HGT5000, HGT5001, and/or HGT5002).

In certain embodiments, the pharmaceutical and liposomal compositions (e.g., lipid nanoparticles) are formulated based in part upon their ability to facilitate the transfection (e.g., of a polynucleotide) of a target cell. In another embodiment, the pharmaceutical and liposomal compositions (e.g., lipid nanoparticles) may be selected and/or prepared to optimize delivery of polynucleotides to a target cell, tissue or organ. For example, if the target cell is a hepatocyte the properties of the pharmaceutical and/or liposomal compositions (e.g., size, charge and/or pH) may be optimized to effectively deliver such composition (e.g., lipid nanoparticles) to the target cell or organ, reduce immune clearance and/or promote retention in that target organ. Alternatively, if the target tissue is the central nervous system the selection and preparation of the pharmaceutical and liposomal compositions must consider penetration of, and retention within the blood brain barrier and/or the use of alternate means of directly delivering such compositions (e.g., lipid nanoparticles) to such target tissue (e.g., via intracerebrovascular administration). In certain embodiments, the pharmaceutical or liposomal compositions or their constituent lipid nanoparticles may be combined with agents that facilitate the transfer of encapsulated materials (e.g., agents which disrupt or improve the permeability of the blood brain barrier and thereby enhance the transfer of such encapsulated polynucleotides to the target cells). While the pharmaceutical and liposomal compositions described herein (e.g., lipid nanoparticles) can facilitate introduction of encapsulated materials such as one or more polynucleotides into target cells, the addition of polycations (e.g., poly L-lysine and protamine) to, for example one or more of the lipid nanoparticles that comprise the pharmaceutical compositions as a copolymer can also facilitate, and in some instances markedly enhance the transfection efficiency of several types of cationic liposomes by 2-28 fold in a number of cell lines both in vitro and in vivo. (See, N. J. Caplen, et al., Gene Ther. 1995; 2: 603; S. Li, et al., Gene Ther. 1997; 4, 891.)

In certain embodiments of the present invention, the pharmaceutical and liposomal compositions (e.g., lipid nanoparticles) are prepared to encapsulate one or more materials or therapeutic agents (e.g., polynucleotides). The process of incorporating a desired therapeutic agent (e.g., mRNA) into a liposome or a lipid nanoparticle is referred to herein as or "loading" or "encapsulating" (Lasic, et al., FEBS Lett., 312: 255-258, 1992). The lipid nanoparticle-loaded or -encapsulated materials (e.g., polynucleotides) may be completely or partially located in the interior space of the lipid nanoparticle, within the bilayer membrane of the lipid nanoparticle, or associated with the exterior surface of the lipid nanoparticle.

Loading or encapsulating, for example, a polynucleotide into a lipid nanoparticle may serve to protect the polynucleotide from an environment which may contain enzymes or chemicals (e.g., serum) that degrade such polynucleotides and/or systems or receptors that cause the rapid excretion of such polynucleotides. Accordingly, in some embodiments, the compositions described herein are capable of enhancing the stability of the polynucleotide(s) encapsulated thereby, particularly with respect to the environments into which such polynucleotides will be exposed. Encapsulating materials, such as for example polynucleotides into one or more of the pharmaceutical and liposomal compositions described herein (e.g., lipid nanoparticles) also facilitates the delivery of such polynucleotides into the target cells and tissues. For example, lipid nanoparticles comprising one or more of the lipid compounds described herein can allow the encapsulated polynucleotide to reach the target cell or may preferentially allow the encapsulated polynucleotide to reach the target cells or organs on a discriminatory basis (e.g., the lipid nanoparticles may concentrate in the liver or spleens of a subject to which such lipid nanoparticles are administered). Alternatively, the lipid nanoparticles may limit the delivery of encapsulated polynucleotides to other non-targeted cells or organs where the presence of the encapsulated polynucleotides may be undesirable or of limited utility.

In certain embodiments, the pharmaceutical and liposomal compositions described herein (e.g., lipid nanoparticles) are prepared by combining multiple lipid components (e.g., one or more of the compounds disclosed herein) with one or more polymer components. For example, a lipid nanoparticle may be prepared using HGT5000, DOPE, CHOL and DMG-PEG2000. A lipid nanoparticle may be comprised of additional lipid combinations in various ratios, including for example, HGT5001, DOPE and DMG-PEG2000. The selection of cationic lipids, non-cationic lipids and/or PEG-modified lipids which comprise the lipid nanoparticles, as well as the relative molar ratio of such lipids to each other, is based upon the characteristics of the selected lipid(s), the nature of the intended target cells or tissues and the characteristics of the materials or polynucleotides to be delivered by the lipid nanoparticle. Additional considerations include, for example, the saturation of the alkyl chain, as well as the size, charge, pH, pKa, fusogenicity and toxicity of the selected lipid(s).

The pharmaceutical and liposomal composition (e.g., lipid nanoparticles) for use in the present invention can be prepared by various techniques which are presently known in the art. Multi-lamellar vesicles (MLV) may be prepared conventional techniques, for example, by depositing a selected lipid on the inside wall of a suitable container or vessel by dissolving the lipid in an appropriate solvent, and then evaporating the solvent to leave a thin film on the inside of the vessel or by spray drying. An aqueous phase may then be added to the vessel with a vortexing motion which results in the formation of MLVs. Unilamellar vesicles (ULV) can then be formed by homogenization, sonication or extrusion of the multi-lamellar vesicles. In addition, unilamellar vesicles can be formed by detergent removal techniques.

In certain embodiments, the pharmaceutical and liposomal compositions of the present invention comprise a lipid nanoparticle wherein the encapsulated polynucleotide (e.g., mRNA) is associated on both the surface of the lipid nanoparticle and encapsulated within the same lipid nanoparticle. For example, during preparation of the compositions of the present invention, one or more of the cationic lipid compounds described herein and which comprise the lipid nanoparticles may associate with the polynucleotides (e.g., mRNA) through electrostatic interactions with such polynucleotides.

In certain embodiments, the pharmaceutical and liposomal compositions of the present invention may be loaded with diagnostic radionuclide, fluorescent materials or other materials that are detectable in both in vitro and in vivo applications. For example, suitable diagnostic materials for use in the present invention may include Rhodamine-dioleoylphosphatidylethanolamine (Rh-PE), Green Fluorescent Protein mRNA, *Renilla* Luciferase mRNA and Firefly Luciferase mRNA.

During the preparation of liposomal compositions described herein, water soluble carrier agents may be also encapsulated in the aqueous interior by including them in the hydrating solution, and lipophilic molecules may be incorporated into the lipid bilayer by inclusion in the lipid formulation. In the case of certain molecules (e.g., cationic or anionic lipophilic polynucleotides), loading of the polynucleotide into preformed lipid nanoparticles or liposomes may be accomplished, for example, by the methods described in U.S. Pat. No. 4,946,683, the disclosure of which is incorporated herein by reference. Following encapsulation of the polynucleotide, the lipid nanoparticles may be processed to remove un-encapsulated mRNA through processes such as gel chromatography, diafiltration or ultrafiltration. For example, if it is desirous to remove externally bound polynucleotide from the surface of the liposomal compositions (e.g., lipid nanoparticles) described herein, such lipid nanoparticles may be subject to a Diethylaminoethyl SEPHACEL column.

In addition to the encapsulated materials (e.g., polynucleotides or one or more therapeutic or diagnostic agents) may be included or encapsulated in the lipid nanoparticle. For example, such additional therapeutic agents may be associated with the surface of the lipid nanoparticle, can be incorporated into the lipid bilayer of the lipid nanoparticle by inclusion in the lipid formulation or loading into preformed lipid nanoparticles (See, U.S. Pat. Nos. 5,194,654 and 5,223,263, which are incorporated by reference herein).

There are several methods for reducing the size, or "sizing", of the liposomal compositions (e.g., lipid nanoparticles) disclosed herein, and any of these methods may generally be employed when sizing is used as part of the invention. The extrusion method is a one method of liposome sizing. (Hope, M J et al. Reduction of Liposome Size and Preparation of Unilamellar Vesicles by Extrusion Techniques. In: *Liposome Technology* (G. Gregoriadis, Ed.) Vol. 1. p 123 (1993)). The method consists of extruding liposomes through a small-pore polycarbonate membrane or an asymmetric ceramic membrane to reduce liposome sizes to a relatively well-defined size distribution. Typically, the suspension is cycled through the membrane one or more times until the desired liposome size distribution is achieved. The liposomes may be extruded through successively smaller pore membranes to achieve gradual reduction in liposome size.

A variety of alternative methods known in the art are available for sizing of a population of lipid nanoparticles. One such sizing method is described in U.S. Pat. No. 4,737,323, incorporated herein by reference. Sonicating a liposome or lipid nanoparticle suspension either by bath or probe sonication produces a progressive size reduction down to small ULV less than about 0.05 microns in diameter. Homogenization is another method that relies on shearing energy to fragment large liposomes into smaller ones. In a typical homogenization procedure, MLV are recirculated through a standard emulsion homogenizer until selected liposome sizes, typically between about 0.1 and 0.5 microns, are observed. The size of the lipid nanoparticles may be determined by quasi-electric light scattering (QELS) as described in Bloomfield, Ann. Rev. Biophys. Bioeng., 10:421-450 (1981), incorporated herein by reference. Average lipid nanoparticle diameter may be reduced by sonication of formed lipid nanoparticles. Intermittent sonication cycles may be alternated with QELS assessment to guide efficient liposome synthesis.

Selection of the appropriate size of the liposomal compositions described herein (e.g., lipid nanoparticles) must take into consideration the site of the target cell or tissue and to some extent the application for which the lipid nanoparticle is being made. As used herein, the phrase "target cell" refers to cells to which one or more of the pharmaceutical and liposomal compositions described herein are to be directed or targeted. In some embodiments, the target cells comprise a particular tissue or organ. In some embodiments, the target cells are deficient in a protein or enzyme of interest. For example, where it is desired to deliver a polynucleotide to a hepatocyte, the hepatocyte represents the target cell. In some embodiments, the pharmaceutical or liposomal compositions (and for example the polynucleotide materials encapsulated therein) of the present invention transfect the target cells on a discriminatory basis (i.e., do not transfect non-target cells). The compositions and methods of the present invention may be prepared to preferentially target a variety of target cells, which include, but are not limited to, hepatocytes, hematopoietic cells, epithelial cells, endothelial cells, lung cells, alveolar cells, bone cells, stem cells, mesenchymal cells, neural cells (e.g., meninges, astrocytes, motor neurons, cells of the dorsal root ganglia and anterior horn motor neurons), photoreceptor cells (e.g., rods and cones), retinal pigmented epithelial cells, secretory cells, cardiac cells, adipocytes, vascular smooth muscle cells, cardiomyocytes, skeletal muscle cells, beta cells, pituitary cells, synovial lining cells, ovarian cells, testicular cells, fibroblasts, B cells, T cells, reticulocytes, leukocytes, granulocytes and tumor cells.

Following transfection of one or more target cells by, for example, the polynucleotides encapsulated in the one or more lipid nanoparticles comprising the pharmaceutical or liposomal compositions disclosed herein, the production of the product (e.g., a polypeptide or protein) encoded by such polynucleotide may be preferably stimulated and the capability of such target cells to express the polynucleotide and produce, for example, a polypeptide or protein of interest is enhanced. For example, transfection of a target cell by one or more compounds or pharmaceutical compositions encapsulating mRNA will enhance (i.e., increase) the production of the protein or enzyme encoded by such mRNA.

In some embodiments, it may be desirable to limit transfection of the polynucleotides to certain cells or tissues. For example, the liver represents an important target organ for the compositions of the present invention in part due to its central role in metabolism and production of proteins and accordingly diseases which are caused by defects in liver-specific gene products (e.g., the urea cycle disorders) may benefit from specific targeting of cells (e.g., hepatocytes). Accordingly, in certain embodiments of the present invention, the structural characteristics of the target tissue may be exploited to direct the distribution of the pharmaceutical and liposomal compositions of the present invention (e.g., an HGT5001-based lipid nanoparticle) to such target tissues. For example, to target hepatocytes one or more of the lipid nanoparticles that comprise the pharmaceutical or liposomal compositions described herein may be sized such that their dimensions are smaller than the fenestrations of the endothelial layer lining hepatic sinusoids in the liver; accordingly the one or more of such lipid nanoparticles can readily penetrate such endothelial fenestrations to reach the target hepatocytes. Alternatively, a lipid nanoparticle may be sized such that the dimensions of the liposome are of a sufficient diameter to limit or expressly avoid distribution into certain cells or tissues. For example, lipid nanoparticles that comprise the pharmaceutical and liposomal compositions described herein may be sized such that their dimensions are larger than the fenestrations of the endothelial layer lining hepatic sinusoids to thereby limit distribution of the liposomal lipid nanoparticle to hepatocytes. In such an embodiment, large liposomal compositions (e.g., lipid nanoparticles) will not easily penetrate the endothelial fenestrations, and would instead be cleared by the macrophage Kupffer cells that line the liver sinusoids. Sizing of, for example, the lipid nanoparticles comprising the pharmaceutical composition may therefore provide an opportunity to further manipulate and precisely control the degree to which expression of the encapsulated polynucleotides may be enhanced in one or more target cells. Generally, the size of at least one of the lipid nanoparticles that comprise the pharmaceutical and liposomal compositions of the present invention is within the range of about 25 to 250 nm, preferably less than about 250 nm, 175 nm, 150 nm, 125 nm, 100 nm, 75 nm, 50 nm, 25 nm or 10 nm.

Similarly, the compositions of the present invention may be prepared to preferentially distribute to other target tissues, cells or organs, such as the heart, lungs, kidneys, spleen. For example, the lipid nanoparticles of the present invention may be prepared to achieve enhanced delivery to the target cells and tissues. Accordingly, the compositions of the present invention may be enriched with additional cationic, non-cationic and PEG-modified lipids to further target tissues or cells.

In some embodiments, the compounds and the pharmaceutical and liposomal compositions described herein (e.g., HGT5002-based lipid nanoparticles) distribute to the cells and tissues of the liver to enhance the delivery, transfection and the subsequent expression of the polynucleotides (e.g., mRNA) encapsulated therein by the cells and tissues of the liver (e.g., hepatocytes) and the corresponding production of the polypeptide or protein encoded by such polynucleotide. While such compositions may preferentially distribute into the cells and tissues of the liver, the therapeutic effects of the expressed polynucleotides and the subsequent production of a protein encoded thereby need not be limited to the target cells and tissues. For example, the targeted cells (e.g., hepatocytes) may function as a "reservoir" or "depot" capable of expressing or producing, and systemically or peripherally excreting a functional protein or enzyme, as disclosed for example, in International Application No. PCT/US2010/058457 and in U.S. Provisional Application No. 61/494,881, the teachings of which are both incorporated herein by reference in their entirety. Accordingly, in certain embodiments of the present invention the one or more of the lipid nanoparticles that comprise the pharmaceutical and liposomal compositions described herein (e.g., HGT5000-based lipid nanoparticles) may target hepatocytes and/or preferentially distribute to the cells and tissues of the liver upon delivery. Following the transfection of the target hepatocytes by the polynucleotide encapsulated in one or more of such lipid nanoparticles, such polynucleotides are expressed (e.g., translated) and a functional product (e.g., a polypeptide or protein) is excreted and systemically distributed, where such functional product may exert a desired therapeutic effect.

The polynucleotides encapsulated in one or more of the compounds or pharmaceutical and liposomal compositions described herein can be delivered to and/or transfect targeted cells or tissues. In some embodiments, the encapsulated polynucleotides are capable of being expressed and functional polypeptide products produced (and in some instances excreted) by the target cell, thereby conferring a beneficial property to, for example the target cells or tissues. Such encapsulated polynucleotides may encode, for example, a hormone, enzyme, receptor, polypeptide, peptide or other protein of interest. In certain embodiments, such encapsulated polynucleotides may also encode a small interfering RNA (siRNA) or antisense RNA for the purpose of modulating or otherwise decreasing or eliminating the expression of an endogenous nucleic acid or gene. In certain embodiments such encapsulated polynucleotides may be natural or recombinant in nature and may exert their therapeutic activity using either sense or antisense mechanisms of action (e.g., by modulating the expression of a target gene or nucleic acid).

Also contemplated by the present invention is the co-delivery of one or more unique polynucleotides to target cells by the compounds or pharmaceutical and liposomal compositions described herein, for example, by combining two unique therapeutic agents or polynucleotides into a single lipid nanoparticle. Also contemplated is the delivery of one or more encapsulated polynucleotides to one or more target cells to treat a single disorder or deficiency, wherein each such polynucleotide functions by a different mechanism of action. For example, the pharmaceutical or liposomal compositions of the present invention may comprise a first polynucleotide which, for example, is encapsulated in a lipid nanoparticle and intended to correct an endogenous protein or enzyme deficiency, and a second polynucleotide intended to deactivate or "knock-down" a malfunctioning endogenous polynucleotide and its protein or enzyme product. Such encapsulated polynucleotides may encode, for example mRNA and siRNA.

While in vitro transcribed polynucleotides (e.g., mRNA) may be transfected into target cells, such polynucleotides may be readily and efficiently degraded by the cell in vivo, thus rendering such polynucleotides ineffective. Moreover, some polynucleotides are unstable in bodily fluids (particularly human serum) and can be degraded or digested even before reaching a target cell. In addition, within a cell, a natural mRNA can decay with a half-life of between 30 minutes and several days. Accordingly, in certain embodiments, the encapsulated polynucleotides provided herein, and in particular the mRNA polynucleotides provided herein, preferably retain at least some ability to be expressed or translated, to thereby produce a functional protein or enzyme within one or more target cells.

In certain embodiments, the pharmaceutical and liposomal compositions comprise one or more of the lipid compounds disclosed herein and one or more lipid nanoparticles that include or encapsulate one or more stabilized polynucleotides (e.g., mRNA which has been stabilized against in vivo nuclease digestion or degradation) that modulate the expression of a gene or that may be expressed or translated to produce a functional polypeptide or protein within one or more target cells. In certain embodiments, the activity of such encapsulated polynucleotides (e.g., mRNA encoding a functional protein or enzyme) is prolonged over an extended period of time. For example, the activity of the polynucleotides may be prolonged such that the pharmaceutical compositions may be administered to a subject on a semi-weekly or bi-weekly basis, or more preferably on a monthly, bi-monthly, quarterly or an annual basis. The extended or prolonged activity of the pharmaceutical compositions of the present invention, and in particular of the encapsulated mRNA, is directly related to the quantity of functional protein or enzyme translated from such mRNA. Similarly, the activity of the compositions of the present invention may be further extended or prolonged by chemical modifications made to further improve or enhance translation of the mRNA polynucleotides. For example, the Kozac consensus sequence plays a role in the initiation of protein translation, and the inclusion of such a Kozac consensus sequence in the encapsulated mRNA polynucleotides may further extend or prolong the activity of the mRNA polynucleotides. Furthermore, the quantity of functional protein or enzyme produced by the target cell is a function of the quantity of polynucleotide (e.g., mRNA) delivered to the target cells and the stability of such polynucleotide. To the extent that the stability of the polynucleotides encapsulated by the compounds or compositions of the present invention may be improved or enhanced, the half-life, the activity of the translated protein or enzyme and the dosing frequency of the composition may be further extended.

In certain embodiments the polynucleotides can be chemically modified for example, to confer stability (e.g., stability relative to the wild-type or naturally-occurring version of the mRNA and/or the version of the mRNA naturally endogenous to target cells). Accordingly, in some embodiments, the encapsulated polynucleotides provided herein comprise at least one chemical modification which confers increased or enhanced stability to the polynucleotide, including, for example, improved resistance to nuclease digestion in vivo. The terms "stable" and "stability" as such terms relate to the polynucleotides encapsulated by the compounds or pharmaceutical and liposomal compositions of the present invention, and particularly with respect to the mRNA, refer to increased or enhanced resistance to degradation by, for example nucleases (i.e., endonucleases or exonucleases) which are normally capable of degrading such RNA. Increased stability can include, for example, less sensitivity to hydrolysis or other destruction by endogenous enzymes (e.g., endonucleases or exonucleases) or conditions within the target cell or tissue, thereby increasing or enhancing the residence of such polynucleotides in the target cell, tissue, subject and/or cytoplasm. The stabilized polynucleotide molecules provided herein demonstrate longer half-lives relative to their naturally occurring, unmodified counterparts (e.g. the wild-type version of the polynucleotide).

In certain embodiments, a polynucleotide can be modified by the incorporation 3' and/or 5' untranslated (UTR) sequences which are not naturally found in the wild-type polynucleotide. Also contemplated by the phrases "chemical modification" and "chemically modified" as such terms related to the polynucleotides encapsulated by the compounds or pharmaceutical and liposomal compositions of the present invention are alterations which improve or enhance translation of mRNA polynucleotides, including for example, the inclusion of sequences which function in the initiation of protein translation (e.g., the Kozac consensus sequence). (Kozak, M., Nucleic Acids Res 15 (20): 8125-48 (1987)). Chemical modifications also include modifications which introduce chemistries which differ from those seen in naturally occurring polynucleotides, for example, covalent modifications such as the introduction of modified nucleotides, (e.g., nucleotide analogs, or the inclusion of pendant groups which are not naturally found in such polynucleotide molecules). In some embodiments, the polynucleotides have undergone a chemical or biological modification to render them more stable prior to encapsulation in one or more lipid nanoparticles. In certain embodiments, exemplary chemical modifications that may be introduced into the polynucleotide include pseudouridine, 2-thiouracil, 5-methyl cytidine, 5-methylcytosine, isocytosine, pseudoisocytosine, 5-bromouracil, 5-propynyluracil, 6-aminopurine, 2-aminopurine, inosine, diaminopurine and 2-chloro-6-aminopurine cytosine. Exemplary chemical modifications to a polynucleotide include the depletion of a base (e.g., by deletion or by the substitution of one nucleotide for another) or chemical modification of a base.

In addition, suitable modifications include alterations in one or more nucleotides of a codon such that the codon encodes the same amino acid but is more stable than the codon found in the wild-type version of the polynucleotide. For example, an inverse relationship between the stability of RNA and a higher number cytidines (C's) and/or uridines (U's) residues has been demonstrated, and RNA devoid of C and U residues have been found to be stable to most RNases (Heidenreich, et al. J Biol Chem 269, 2131-8 (1994)). In some embodiments, the number of C and/or U residues in an mRNA sequence is reduced. In a another embodiment, the number of C and/or U residues is reduced by substitution of one codon encoding a particular amino acid for another codon encoding the same or a related amino acid. Contemplated modifications to the mRNA polynucleotides encapsulated by the compounds or pharmaceutical and liposomal compositions of the present invention also include the incorporation of pseudouridines. The incorporation of pseudouridines into the mRNA polynucleotides encapsulated by the compounds or pharmaceutical and liposomal compositions of the present invention may enhance stability and translational capacity, as well as diminishing immunogenicity in vivo. (See, e.g., Karikó, K., et al., Molecular Therapy 16 (11): 1833-1840 (2008)). Substitutions and modifications to the polynucleotides encapsulated by the compounds or pharmaceutical and liposomal compositions of the present invention may be performed by methods readily known to one or ordinary skill in the art.

The constraints on reducing the number of C and U residues in a sequence will likely be greater within the coding region of an mRNA, compared to an untranslated region, (i.e., it will likely not be possible to eliminate all of the C and U residues present in the message while still retaining the ability of the message to encode the desired amino acid sequence). The degeneracy of the genetic code, however presents an opportunity to allow the number of C and/or U residues that are present in the sequence to be reduced, while maintaining the same coding capacity (i.e., depending on which amino acid is encoded by a codon, several different possibilities for modification of RNA sequences may be possible). For example, the codons for Gly can be altered to GGA or GGG instead of GGU or GGC.

The term chemical modification also includes, for example, the incorporation of non-nucleotide linkages or modified nucleotides into the polynucleotide sequences of the present invention (e.g., end-blocking modifications to one or both the 3' and 5' ends of an mRNA molecule encoding a functional protein or enzyme). Such modifications may include the addition of bases to a polynucleotide sequence (e.g., the inclusion of a poly A tail or a longer poly A tail), the alteration of the 3' UTR or the 5' UTR, complexing the polynucleotide with an agent (e.g., a protein or a complementary polynucleotide molecule), and inclusion of elements which change the structure of a polynucleotide molecule (e.g., which form secondary structures).

The poly A tail is thought to stabilize natural messengers and synthetic sense RNA. Therefore, in certain embodiments a long poly A tail can be added to an mRNA molecule thus rendering the RNA more stable. Poly A tails can be added using a variety of art-recognized techniques. For example, long poly A tails can be added to synthetic or in vitro transcribed RNA using poly A polymerase (Yokoe, et al. Nature Biotechnology. 1996; 14: 1252-1256). A transcription vector can also encode long poly A tails. In addition, poly A tails can be added by transcription directly from PCR products. Poly A may also be ligated to the 3' end of a sense RNA with RNA ligase (see, e.g., Molecular Cloning A Laboratory Manual, 2nd Ed., ed. by Sambrook, Fritsch and Maniatis (Cold Spring Harbor Laboratory Press: 1991 edition)). In certain embodiments, the length of the poly A tail is at least about 90, 200, 300, 400 at least 500 nucleotides. In certain embodiments, the length of the poly A tail is adjusted to control the stability of a modified sense mRNA molecule of the invention and, thus, the transcription of protein. For example, since the length of the poly A tail can influence the half-life of a sense mRNA molecule, the length of the poly A tail can be adjusted to modify the level of resistance of the mRNA to nucleases and thereby control the time course of polynucleotide expression and protein production in a target cell. In certain embodiments, the stabilized polynucleotide molecules are sufficiently resistant to in vivo degradation (e.g., by nucleases), such that they may be delivered to the target cell without a lipid nanoparticle.

In some embodiments, the encapsulated polynucleotides (e.g., mRNA encoding a deficient protein) may optionally include chemical or biological modifications which, for example, improve the stability and/or half-life of such polynucleotide or which improve or otherwise facilitate translation of such polynucleotide.

In certain embodiments, the chemical modifications are end-blocking modification of the one or more polynucleotides which comprise the pharmaceutical compositions of the invention. For example, such polynucleotides can be modified by the incorporation 3' and/or 5' untranslated (UTR) sequences which are not naturally found in the wild-type polynucleotide. In certain embodiments, 3' and/or 5' flanking sequence which naturally flanks an mRNA and encodes a second, unrelated protein can be incorporated into the nucleotide sequence of an mRNA molecule encoding a or functional protein in order to modify it. For example, 3' or 5' sequences from mRNA molecules which are stable (e.g., globin, actin, GAPDH, tubulin, histone, or citric acid cycle enzymes) can be incorporated into the 3' and/or 5' region of a sense mRNA polynucleotide molecule to increase the stability of the sense mRNA molecule.

Also contemplated by the present invention are modifications to the polynucleotide sequences made to one or both of the 3' and 5' ends of the polynucleotide. For example, the present invention contemplates modifications to the 5' end of the polynucleotides (e.g., mRNA) to include a partial sequence of a CMV immediate-early 1 (IE1) gene, or a fragment thereof to improve the nuclease resistance and/or improve the half-life of the polynucleotide. In addition to increasing the stability of the mRNA polynucleotide sequence, it has been surprisingly discovered the inclusion of a partial sequence of a CMV immediate-early 1 (IE1) gene (e.g., to one or more of the 5' untranslated region and 3' untranslated region of the mRNA) further enhances the translation of the mRNA. Also contemplated is the inclusion of a sequence encoding human growth hormone (hGH), or a fragment thereof to one or both of the 3' and 5' ends of the polynucleotide (e.g., mRNA) to further stabilize the polynucleotide. Generally, the contemplated chemical modifications improve the stability and/or pharmacokinetic properties (e.g., half-life) of the polynucleotide relative to their unmodified counterparts, and include, for example modifications made to improve such polynucleotides' resistance to in vivo nuclease digestion.

In some embodiments, the pharmaceutical composition, the two or more lipid nanoparticles comprised therein or the polynucleotides encapsulated by such lipid nanoparticles can comprise a stabilizing reagent. The compositions can include one or more formulation reagents that bind directly or indirectly to, and stabilize the polynucleotide, thereby enhancing residence time in the cytoplasm of a target cell. Such reagents preferably lead to an improved half-life of a polynucleotide in the target cells. For example, the stability of an mRNA and efficiency of translation may be increased by the incorporation of "stabilizing reagents" that form complexes with the polynucleotides (e.g., mRNA) that naturally occur within a cell (see e.g., U.S. Pat. No. 5,677,124). Incorporation of a stabilizing reagent can be accomplished for example, by combining the poly A and a protein with the mRNA to be stabilized in vitro before loading or encapsulating the mRNA within the one or more lipid nanoparticles that comprise the pharmaceutical composition. Exemplary stabilizing reagents include one or more proteins, peptides, aptamers, translational accessory protein, mRNA binding proteins, and/or translation initiation factors.

Stabilization of the pharmaceutical and liposomal compositions described herein (e.g., lipid nanoparticles) may also be improved by the use of opsonization-inhibiting moieties, which are typically large hydrophilic polymers that are chemically or physically bound or otherwise incorporated into the lipid nanoparticle (e.g., by the intercalation of a lipid-soluble anchor into the membrane itself, or by binding directly to active groups of membrane lipids). These opsonization-inhibiting hydrophilic polymers form a protective surface layer which significantly decreases the uptake of the liposomes by the macrophage-monocyte system and reticulo-endothelial system (e.g., as described in U.S. Pat. No. 4,920,016, the entire disclosure of which is herein incorporated by reference). For example, delays in the uptake of lipid nanoparticles by the reticuloendothelial system may be facilitated by the addition of a hydrophilic polymer surface coating onto or into lipid nanoparticles to mask the recognition and uptake of the liposomal-based lipid nanoparticle by the reticuloendothelial system. For example, in certain embodiments, one or more of the lipid nanoparticles that comprise the pharmaceutical compositions disclosed herein comprise a polyethyleneglycol (PEG) polymer or a PEG-modified lipid to further enhance delivery of such lipid nanoparticles to the target cell and tissues.

When RNA is hybridized to a complementary polynucleotide molecule (e.g., DNA or RNA) it may be protected from nucleases. (Krieg, et al. Melton. Methods in Enzymology. 1987; 155, 397-415). The stability of hybridized mRNA is likely due to the inherent single strand specificity of most RNases. In some embodiments, the stabilizing reagent selected to complex a polynucleotide is a eukaryotic protein, (e.g., a mammalian protein). In yet another embodiment, the polynucleotide (e.g., mRNA) for use in sense therapy can be modified by hybridization to a second polynucleotide molecule. If an entire mRNA molecule were hybridized to a complementary polynucleotide molecule translation initiation may be reduced. In some embodiments the 5' untranslated region and the AUG start region of the mRNA molecule may optionally be left unhybridized. Following translation initiation, the unwinding activity of the ribosome complex can function even on high affinity duplexes so that translation can proceed. (Liebhaber. J. Mol. Biol. 1992; 226: 2-13; Monia, et al. J Biol Chem. 1993; 268: 14514-22.) It will be understood that any of the above described methods for enhancing the stability of polynucleotides may be used either alone or in combination with one or more of any of the other above-described methods and/or compositions.

In certain embodiments, the pharmaceutical compositions of the present invention enhance the delivery of lipid nanoparticle-encapsulated polynucleotides to one or more target cells, tissues or organs. In some embodiments, enhanced delivery to one or more target cells comprises increasing the amount of polynucleotide that comes in contact or is otherwise delivered to the target cells. In some embodiments, enhancing delivery to target cells comprises reducing the amount of polynucleotide that comes into contact with non-target cells. In some embodiments, enhancing delivery to target cells comprises allowing the transfection of at least some target cells with the encapsulated polynucleotide. In some embodiments, the level of expression of the polynucleotide encapsulated by the lipid nanoparticles which comprise the subject pharmaceutical compositions and the corresponding production of the functional protein or enzyme encoded thereby is increased in the target cells.

The polynucleotides encapsulated by the compounds or pharmaceutical and liposomal compositions of the present invention may be optionally combined with a reporter gene (e.g., upstream or downstream of the coding region of the polynucleotide) which, for example, facilitates the determination of polynucleotide delivery to the target cells or tissues. Suitable reporter genes may include, for example, Green Fluorescent Protein mRNA (GFP mRNA), *Renilla* Luciferase mRNA (Luciferase mRNA), Firefly Luciferase mRNA, or any combinations thereof. For example, GFP mRNA may be fused with a polynucleotide encoding GLA mRNA (SEQ ID NO: 4) or EPO mRNA (SEQ ID NO: 1) to facilitate confirmation of mRNA localization in the plasma or in one or more target cells, tissues or organs.

In some embodiments, the pharmaceutical compositions of the present invention comprise one or more additional molecules (e.g., proteins, peptides, aptamers or oliogonucleotides) which facilitate the transfer of the polynucleotides (e.g., mRNA, miRNA, snRNA and snoRNA) from the lipid nanoparticle into an intracellular compartment of the target cell. In some embodiments, the additional molecule facilitates the delivery of the polynucleotides into, for example, the cytosol, the lysosome, the mitochondrion, the nucleus, the nucleolae or the proteasome of a target cell. Also included are agents that facilitate the transport of the translated protein of interest from the cytoplasm to its normal intercellular location (e.g., in the mitochondrion) to treat deficiencies in that organelle. In some embodiments, the agent is selected from the group consisting of a protein, a peptide, an aptamer, and an oligonucleotide.

In some embodiments, the compositions of the present invention facilitate a subject's endogenous production of one or more functional proteins and/or enzymes, and in particular the production of proteins and/or enzymes which demonstrate less immunogenicity relative to their recombinantly-prepared counterparts. In a certain embodiments of the present invention, the lipid nanoparticles comprise polynucleotides which encode mRNA of a deficient protein or enzyme. Upon distribution of such compositions to the target tissues and the subsequent transfection of such target cells, the exogenous mRNA loaded or encapsulated into the lipid nanoparticles that comprise the compositions may be translated in vivo to produce a functional protein or enzyme encoded by such encapsulated mRNA (e.g., a protein or enzyme in which the subject is deficient). Accordingly, in certain embodiments the compositions of the present invention exploit a subject's ability to translate exogenously- or recombinantly-prepared mRNA to produce an endogenously-translated protein or enzyme, and thereby produce (and where applicable excrete) a functional protein or enzyme. The translated proteins or enzymes may also be characterized by the in vivo inclusion of native post-translational modifications which may often be absent in recombinantly-prepared proteins or enzymes, thereby further reducing the immunogenicity of the translated protein or enzyme.

The encapsulation of mRNA in the lipid nanoparticles and the administration of the pharmaceutical compositions comprising such lipid nanoparticles avoid the need to deliver the mRNA to specific organelles within a target cell (e.g., mitochondria). Rather, upon transfection of a target cell and delivery of the encapsulated mRNA to the cytoplasm of the target cell, the mRNA contents of the lipid nanoparticles may be translated and a functional protein or enzyme produced.

The present invention also contemplates the discriminatory targeting of one or more target cells and tissues by both passive and active targeting means. The phenomenon of passive targeting exploits the natural distributions patterns of lipid nanoparticles in vivo without relying upon the use of additional excipients or means to enhance recognition of the lipid nanoparticle by one or more target cells. For example, lipid nanoparticles which are subject to phagocytosis by the cells of the reticulo-endothelial system are likely to accumulate in the liver or spleen, and accordingly may provide means to passively direct the delivery of the compositions to such target cells.

Alternatively, the present invention contemplates active targeting, which involves the use of additional excipients, referred to herein as "targeting ligands" that may be bound (either covalently or non-covalently) to the lipid nanoparticle to encourage localization of such lipid nanoparticle at certain target cells or target tissues. For example, targeting may be mediated by the inclusion of one or more endogenous targeting ligands (e.g., apolipoprotein E) in or on the lipid nanoparticle to encourage distribution to the target cells or tissues. Recognition of the targeting ligand by the target tissues actively facilitates tissue distribution to, and cellular uptake of the lipid nanoparticles and/or their contents by the target cells and tissues. For example, in certain embodiments, one or more of the lipid nanoparticles that comprise the pharmaceutical formulation may comprise an apolipoprotein-E targeting ligand in or on such lipid nanoparticles to facilitate or encourage recognition and binding of such lipid nanoparticle to endogenous low density lipoprotein receptors expressed, for example by hepatocytes. As provided herein, the composition can comprise a ligand capable of enhancing affinity of the compositions to one or more target cells. Targeting ligands may be linked to the outer bilayer of the lipid nanoparticle during formulation or post-formulation. These methods are well known in the art. In addition, some lipid nanoparticles may comprise fusogenic polymers such as PEAA, hemagluttinin, other lipopeptides (see U.S. patent application Ser. Nos. 08/835,281, and 60/083,294, which are incorporated herein by reference) and other features useful for in vivo and/or intracellular delivery. In other embodiments, the compositions of the present invention demonstrate improved transfection efficacies, and/or demonstrate enhanced selectivity towards target cells or tissues of interest. Contemplated therefore are compositions or lipid nanoparticles that comprise one or more ligands (e.g., peptides, aptamers, oligonucleotides, a vitamin or other molecules) that are capable of enhancing the affinity of the compositions or their constituent lipid nanoparticles and their polynucleotide contents to one or more target cells or tissues. Suitable ligands may optionally be bound or linked to the surface of the lipid nanoparticle. In some embodiments, the targeting ligand may span the surface of a lipid nanoparticle or be encapsulated within the lipid nanoparticle. Suitable ligands are selected based upon their physical, chemical or biological properties (e.g., selective affinity and/or recognition of target cell surface markers or features.) Cell-specific target sites and their corresponding targeting ligand can vary widely. Suitable targeting ligands are selected such that the unique characteristics of a target cell are exploited, thus allowing the composition to discriminate between target and non-target cells. For example, compositions of the present invention may bear surface markers (e.g., apolipoprotein-B or apolipoprotein-E) that selectively enhance recognition of, or affinity to hepatocytes (e.g., by receptor-mediated recognition of and binding to such surface markers). Additionally, the use of galactose as a targeting ligand would be expected to direct the compositions of the present invention to parenchymal hepatocytes, or alternatively the use of mannose containing sugar residues as a targeting ligand would be expected to direct the compositions of the present invention to liver endothelial cells (e.g., mannose containing sugar residues that may bind preferentially to the asialoglycoprotein receptor present in hepatocytes). (See Hillery A M, et al. "Drug Delivery and Targeting: For Pharmacists and Pharmaceutical Scientists" (2002) Taylor & Francis, Inc.) The presentation of such targeting ligands that have been conjugated to moieties present in the lipid nanoparticle therefore facilitate recognition and uptake of the liposomal compositions of the present invention by one or more target cells and tissues. Examples of suitable targeting ligands include one or more peptides, proteins, aptamers, vitamins and oligonucleotides.

As used herein, the term "subject" refers to any animal (e.g., a mammal), including, but not limited to, humans, non-human primates, rodents, and the like, to which the compounds, pharmaceutical or liposomal compositions and methods of the present invention may be administered. Typically, the terms "subject" and "patient" are used interchangeably herein in reference to a human subject.

The ability of the compounds and pharmaceutical or liposomal compositions described herein (e.g., lipid nanoparticles) to modulate or enhance the expression of encapsulated polynucleotides and the production of a polypeptide or protein provides novel and more efficient means of effectuating the in vivo production of polypeptides and proteins for the treatment of a host of diseases or pathological conditions. Such lipid nanoparticle compositions are particularly suitable for the treatment of diseases or pathological conditions associated with the aberrant expression of nucleic acids encoding a protein or enzyme. For example, the successful delivery of polynucleotides such as mRNA to target organs such as the liver and in particular, to hepatocytes, can be used for the treatment and the correction of in-born errors of metabolism that are localized to the liver. Accordingly, the compounds, pharmaceutical compositions and related methods described herein may be employed to treat a wide range of diseases and pathological conditions, in particular those diseases which are due to protein or enzyme deficiencies. The polynucleotides encapsulated by the compounds or pharmaceutical and liposomal compositions described herein (e.g., HGT5001-based lipid nanoparticles) may encode a functional product (e.g., a protein, enzyme, polypeptide, peptide, functional RNA, and/or antisense molecule), and preferably encodes a product whose in vivo production is desired.

The compounds, pharmaceutical compositions and related methods of the present invention are broadly applicable to the delivery of therapeutic agents such as polynucleotides, and in particular mRNA, to treat a number of disorders. In particular, such compounds, compositions and related methods of the present invention are suitable for the treatment of diseases or disorders relating to the deficiency of proteins and/or enzymes. In certain embodiments, the lipid nanoparticle-encapsulated polynucleotides encode functional proteins or enzymes that are excreted or secreted by one or more target cells into the surrounding extracellular fluid (e.g., mRNA encoding hormones and neurotransmitters). Alternatively, in another embodiment, the polynucleotides encapsulated by the compounds or pharmaceutical and liposomal compositions of the present invention encode functional proteins or enzymes that remain in the cytosol of one or more target cells (e.g., mRNA encoding an enzyme associated with urea cycle or lysosomal storage metabolic disorders). Other disorders for which the compounds, pharmaceutical compositions and related methods of the present invention are useful include, but are not limited to, disorders such as SMN1-related spinal muscular atrophy (SMA); amyotrophic lateral sclerosis (ALS); GALT-related galactosemia; Cystic Fibrosis (CF); SLC3A1-related disorders including cystinuria; COL4A5-related disorders including Alport syndrome; galactocerebrosidase deficiencies; X-linked adrenoleukodystrophy and adrenomyeloneuropathy; Friedreich's ataxia; Pelizaeus-Merzbacher disease; TSC1 and TSC2-related tuberous sclerosis; Sanfilippo B syndrome (MPS IIIB); CTNS-related cystinosis; the FMR1-related disorders which include Fragile X syndrome, Fragile X-Associated Tremor/Ataxia Syndrome and Fragile X Premature Ovarian Failure Syndrome; Prader-Willi syndrome; Fabry disease; hereditary hemorrhagic telangiectasia (AT); Niemann-Pick disease Type C1; the neuronal ceroid lipofuscinoses-related diseases including Juvenile Neuronal Ceroid Lipofuscinosis (JNCL), Juvenile Batten disease, Santavuori-Haltia disease, Jansky-Bielschowsky disease, and PTT-1 and TPP1 deficiencies; EIF2B1, EIF2B2, EIF2B3, EIF2B4 and EIF2B5-related childhood ataxia with central nervous system hypomyelination/vanishing white matter; CACNA1A and CACNB4-related Episodic Ataxia Type 2; the MECP2-related disorders including Classic Rett Syndrome, MECP2-related Severe Neonatal Encephalopathy and PPM-X Syndrome; CDKL5-related Atypical Rett Syndrome; Kennedy's disease (SBMA); Notch-3 related cerebral autosomal dominant arteriopathy with subcortical infarcts and leukoencephalopathy (CADASIL); SCN1A and SCN1B-related seizure disorders; the Polymerase G-related disorders which include Alpers-Huttenlocher syndrome, POLG-related sensory ataxic neuropathy, dysarthria, and ophthalmoparesis, and autosomal dominant and recessive progressive external ophthalmoplegia with mitochondrial DNA deletions; X-Linked adrenal hypoplasia; X-linked agammaglobulinemia; and Wilson's disease. In certain embodiments, the polynucleotides, and in particular mRNA, of the present invention may encode functional proteins or enzymes. For example, the compositions of the present invention may include mRNA encoding ornithine transcarbamylase (OTC), carbamoyl-phosphate synthetase 1 (CPS1), argininosuccinate synthetase (ASS1), argininosuccinate lyase (ASL) or arginase 1 (ARG1), cystic fibrosis transmembrane conductance regulator (CFTR), acid alpha glucosidase, arylsulfatase A, α-galactosidase A, erythropoietin (e.g., SED ID NO: 4), α1-antitrypsin, carboxypeptidase N, alpha-L-iduronidase, iduronate-2-sulfatase, iduronate sulfatase, N-acetylglucosamine-1-phosphate transferase, N-acetylglucosaminidase, alpha-glucosaminide acetyltransferase, N-acetylglucosamine 6-sulfatase, N-acetylgalactosamine-4-sulfatase, beta-glucosidase, galactose-6-sulfate sulfatase, beta-galactosidase, beta-glucuronidase, glucocerebrosidase, heparan sulfamidase, heparin-N-sulfatase, lysosomal acid lipase, hyaluronidase, galactocerebrosidase, human growth hormone, survival motor neuron, Factor VIII, Factor IX or low density lipoprotein receptors.

In one embodiment, the mRNA encodes a protein or an enzyme selected from the group consisting of human growth hormone, erythropoietin, al-antitrypsin, acid alpha glucosidase, arylsulfatase A, carboxypeptidase N, α-galactosidase A, alpha-L-iduronidase, iduronate-2-sulfatase, iduronate sulfatase, N-acetylglucosamine-1-phosphate transferase, N-acetylglucosaminidase, alpha-glucosaminide acetyltransferase, N-acetylglucosamine 6-sulfatase, N-acetylgalactosamine-4-sulfatase, beta-glucosidase, galactose-6-sulfate sulfatase, beta-galactosidase, beta-glucuronidase, glucocerebrosidase, heparan sulfamidase, heparin-N-sulfatase, lysosomal acid lipase, hyaluronidase, galactocerebrosidase, ornithine transcarbamylase (OTC), carbamoyl-phosphate synthetase 1 (CPS1), argininosuccinate synthetase (ASS1), argininosuccinate lyase (ASL), arginase 1 (ARG1), cystic fibrosis transmembrane conductance regulator (CFTR), survival motor neuron (SMN), Factor VIII, Factor IX and low density lipoprotein receptors (LDLR).

The compounds and pharmaceutical compositions described herein may be administered to a subject. In some embodiments, the compositions are formulated in combination with one or more additional polynucleotides, carriers, targeting ligands or stabilizing reagents or other suitable excipients. Techniques for formulation and administration of drugs may be found in "Remington's Pharmaceutical Sciences," Mack Publishing Co., Easton, Pa., latest edition.

The compounds and the pharmaceutical and liposomal compositions (e.g., lipid nanoparticles) of the present invention may be administered and dosed in accordance with current medical practice, taking into account the clinical condition of the subject, the nature of the encapsulated materials, the site and method of administration, the scheduling of administration, the subject's age, sex, body weight and other factors relevant to clinicians of ordinary skill in the art. The "effective amount" for the purposes herein may be determined by such relevant considerations as are known to those of ordinary skill in experimental clinical research, pharmacological, clinical and medical arts. In some embodiments, the amount administered is effective to achieve at least some stabilization, improvement or elimination of symptoms and other indicators as are selected as appropriate measures of disease progress, regression or improvement by those of skill in the art. For example, a suitable amount and dosing regimen is one that causes at least transient expression of the one or more polynucleotides in the target cells.

Suitable routes of administration of the compounds and pharmaceutical compositions disclosed herein include, for example, oral, rectal, vaginal, transmucosal, or intestinal administration; parenteral delivery, including intramuscular, subcutaneous, intramedullary injections, as well as intrathecal, intracerebroventricular, direct intraventricular, intravenous, intraperitoneal, intranasal, or intraocular injections or infusions. In certain embodiments, the administration of the compounds or compositions (e.g., lipid nanoparticle) described herein to a subject facilitates the contacting of such compounds or compositions to one or more target cells, tissues or organs.

Alternately, the compounds and compositions of the present invention may be administered in a local rather than systemic manner, for example, via injection or infusion of the pharmaceutical compositions directly into a targeted tissue, preferably in a depot or sustained release formulation, such that the contacting of the targeted cells with the constituent lipid nanoparticles may be further facilitated. Local delivery can be affected in various ways, depending on the tissue to be targeted. For example, aerosols containing compositions of the present invention can be inhaled (for nasal, tracheal, or bronchial delivery); compositions of the present invention can be injected into the site of injury, disease manifestation, or pain, for example; compositions can be provided in lozenges for oral, tracheal, or esophageal application; can be supplied in liquid, tablet or capsule form for administration to the stomach or intestines, can be supplied in suppository form for rectal or vaginal application; or can even be delivered to the eye by use of creams, drops, or even injection. Formulations containing the compounds of the present invention complexed with therapeutic molecules or ligands can even be surgically administered, for example in association with a polymer or other structure or substance that can allow the compositions to diffuse from the site of implantation to surrounding cells. Alternatively, such compositions can be applied surgically without the use of polymers or supports.

Also contemplated herein are lyophilized pharmaceutical compositions comprising one or more of the compounds disclosed herein and related methods for the use of such lyophilized compositions as disclosed for example, in U.S. Provisional Application No. 61/494,882, filed Jun. 8, 2011, the teachings of which are incorporated herein by reference in their entirety.

In certain embodiments, the compositions of the present invention are formulated such that they are suitable for extended-release of the, for example, polynucleotides or nucleic acids encapsulated therein. Such extended-release compositions may be conveniently administered to a subject at extended dosing intervals. For example, in certain embodiments, the compositions of the present invention are administered to a subject twice day, daily or every other day. In a certain embodiments, the compositions of the present invention are administered to a subject twice a week, once a week, every ten days, every two weeks, every three weeks, or more preferably every four weeks, once a month, every six weeks, every eight weeks, every other month, every three months, every four months, every six months, every eight months, every nine months or annually. Also contemplated are compositions and lipid nanoparticles which are formulated for depot administration (e.g., intramuscularly, subcutaneously, intravitreally) to either deliver or release a polynucleotide (e.g., mRNA) over extended periods of time. Preferably, the extended-release means employed are combined with modifications (e.g., chemical modifications) introduced into the polynucleotides to enhance stability.

While certain compounds, compositions and methods of the present invention have been described with specificity in accordance with certain embodiments, the following examples serve only to illustrate the compounds of the invention and are not intended to limit the same. Each of the publications, reference materials and the like referenced herein to describe the background of the invention and to provide additional detail regarding its practice are hereby incorporated by reference in their entirety.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. The publications and other reference materials referenced herein to describe the background of the invention and to provide additional detail regarding its practice are hereby incorporated by reference.

EXAMPLES

Example 1

The compound (15Z,18Z)—N,N-dimethyl-6-(9Z,12Z)-octadeca-9,12-dien-1-yl)tetracosa-15,18-dien-1-amine (referred to herein as "HGT5000") was prepared in accordance with the general synthetic scheme shown below in Reaction 1.

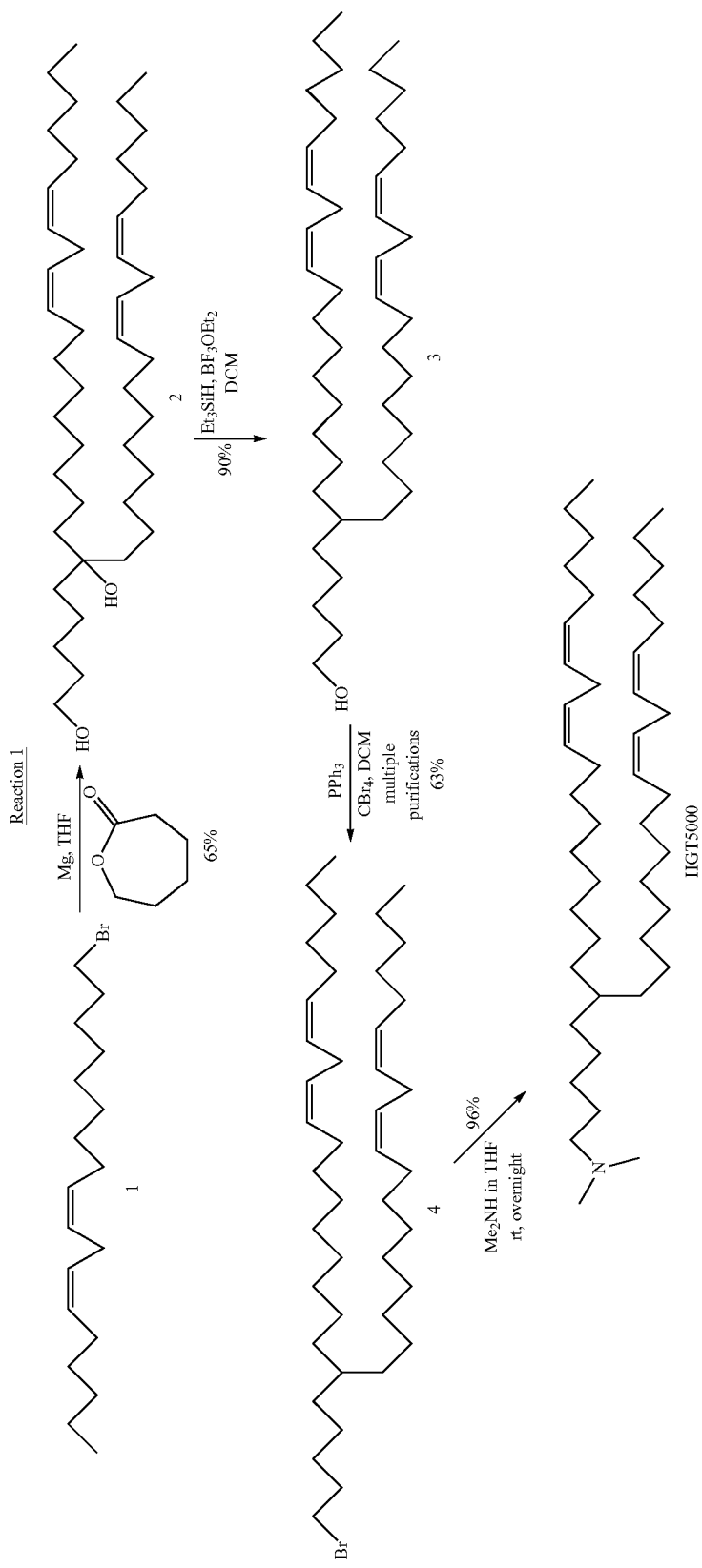

The intermediate compound (15Z,18Z)-6-[(9Z,12Z)-octadeca-9,12-dien-1-yl]tetracosa-15,18-diene-1,6-diol identified as compound (2) in Reaction 1 above was prepared as follows. To a 100 mL round bottom flask was added 10 g (30 mmol) of compound (1) (linoleyl bromide) and dry THF (20 mL) under nitrogen. Magnesium powder (1.11 g, 45 mmol) was added to the stirred reaction solution followed by 2 drops of dibromoethane at room temperature. The reaction mixture was stirred at 50° C. for 1 hour, and then diluted with dry THF (40 mL). The reaction mixture was stirred another 15 minutes at room temperature.

In a separate 250 mL 3-neck flask was taken ε-caprolactone (1.44 mL, 13.5 mmol) in dry THF (20 mL) under nitrogen. To the stirred solution was added the Grignard reagent through a cannula at 0° C. The resulting mixture was heated at 85° C. for 3 hours. After cooling to room temperature, the reaction mixture was then quenched with $NH_4Cl$ solution and extracted with dichloromethane (3×100 mL). The combined extracts were washed with brine (50 mL), dried ($Na_2SO_4$) and concentrated. The residue was purified twice by silica gel column chromatography (gradient elution from hexane to 3:2 hexane/EA) to afford compound (2) as an oil. Yield: 5.46 g (65%). $^1$H NMR (301 MHz, $CDCl_3$) δ: 5.25-5.45 (m, 8H), 3.65 (m, 2H), 2.77 (t, J=6.2 Hz, 4H), 1.95-2.1 (m, 8H), 1.2-1.70 (m, 50H), 0.88 (t, J=6.9 Hz, 6H).

The intermediate compound (15Z,18Z)-6-[(9Z,12Z)-octadeca-9,12-dien-1-yl]tetracosa-15,18-diene-1-ol identified as compound (3) in Reaction 1 above was prepared as follows. Compound (2) (4.4 g, 7.15 mmol) was dissolved in dichloromethane (70 ml). The solution was stirred under nitrogen at 0° C. and $Et_3SiH$ (8.07 mL, 50.08 mmol) was added. Boron trifluoride diethyl etherate (8.77 mL, 71.5 mmol) was added dropwise at 0° C. The reaction mixture was then stirred at the same temperature for 3 hours, then at room temperature for 30 minutes. The reaction was then quenched by 10% sodium carbonate solution (200 mL). The resulting mixture was extracted twice with dichloromethane (2×150 mL). The combined extract was washed with brine, dried over sodium sulfate, filtered and concentrated under reduced pressure. The crude product was purified twice by silica gel column chromatography (gradient elution from hexane to 2:1 hexane/EA) to afford the desired intermediate product compound (3) as an oil. Yield: 3.86 g (90%). $^1$H NMR (301 MHz, $CDCl_3$) δ: 5.2-5.5 (m, 8H), 3.62 (q, J=6.6 Hz, 2H), 2.77 (t, J=6 Hz, 4H), 1.9-2.1 (m, 8H), 1.5-1.65 (m, 2H), 1.1-1.45 (m, 48H), 0.88 (t, J=6.9 Hz, 6H).

The intermediate compound (6Z,9Z,28Z,31Z)-19-(5-bromopentyl)heptatriaconta-6,9,28,31-tetraene identified as compound (4) in Reaction 1 above was prepared as follows. A solution of compound (3) (3.86 g, 6.45 mmol) in dichloromethane (80 mL) was stirred under nitrogen at 0° C. Triphenylphosphine (1.86 g, 7.10 mmol) was added to the solution followed by tetrabromomethane (2.14 g, 6.45 mmol). The reaction mixture was stirred at 0° C. for 3 hours, then at room temperature for 30 minutes. TLC still showed a presence of starting material, accordingly another portion of triphenylphosphine (0.4 g) was added at 0° C. After 30 minutes, all the starting material had been consumed and the reaction mixture was then concentrated. To the residue was added a mixture of ether and hexane (2:1, 200 mL) and the slurry stirred for 15 minutes. Solids were filtered off and the filtrate was concentrated under reduced pressure. The residue was purified by multiple column chromatographies (gradient elution from hexane to 3:2 hexane/EA) to afford the desired intermediate product compound (4). Yield: 2.7 g (63%). $^1$H NMR (301 MHz, $CDCl_3$) δ: 5.2-5.5 (m, 8H), 3.40 (t, J=7 Hz, 2H), 2.77 (t, J=6 Hz, 4H), 1.8-2.1 (m, 8H), 1.15-1.5 (m, 46H), 0.88 (t, J=6.6 Hz, 6H).

To prepare the HGT5000 compound (15Z,18Z)—N,N-dimethyl-6-(9Z,12Z)-octadeca-9,12-dien-1-yl)tetracosa-15,18-dien-1-amine), compound (4) (2.70 g, 4.07 mmol) was dissolved in a 2M solution of dimethylamine in THF (204 mL, 100 eq.). The resulting solution was stirred under nitrogen at room temperature for 16 hours. The reaction mixture was then concentrated under reduced pressure. The residue was purified twice by silica gel column chromatography (gradient elution from 0%-10% methanol in dichloromethane) to give the HGT5000 compound as a light yellow oil. Yield: 2.52 g (96%). $^1$H NMR (301 MHz, $CDCl_3$) δ: 5.42-5.29 (m, 8H), 2.77 (t, J=6.0 Hz, 4H), 2.28-2.24 (m, 8H), 2.01-2.08 (m, 8H), 1.66-1.63 (m, 2H), 1.41-1.20 (m, 48H), 0.88 (t, J=6.9 Hz, 6H). $^{13}$C NMR ($CDCl_3$) δ: 130.3, 128.0, 59.9, 45.3, 37.5, 33.8, 31.6, 30.3, 29.8, 29.7, 29.4, 28.0, 27.5, 27.3, 26.8, 26.7, 25.7, 22.7. APCI [M+H] 626.6. $R_f$=0.48 (10% MeOH in DCM).

Example 2

The compound (15Z,18Z)—N,N-dimethyl-6-((9Z,12Z)-octadeca-9,12-dien-1-yl)tetracosa-4,15,18-trien-1-amine (referred to herein as "HGT5001") was prepared in accordance with the general synthetic scheme illustrated below in Reaction 2.

Reaction 2

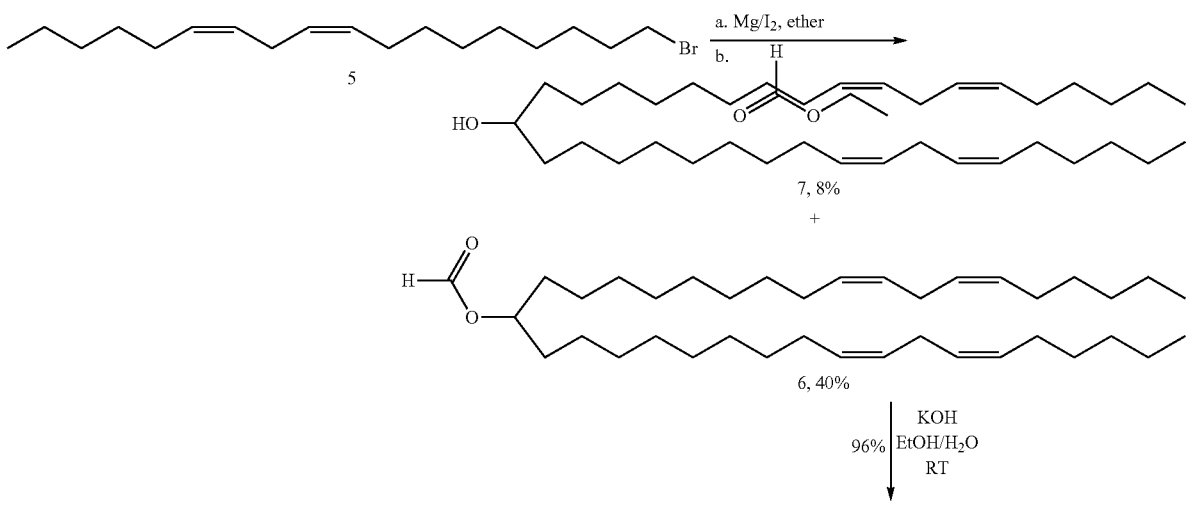

-continued

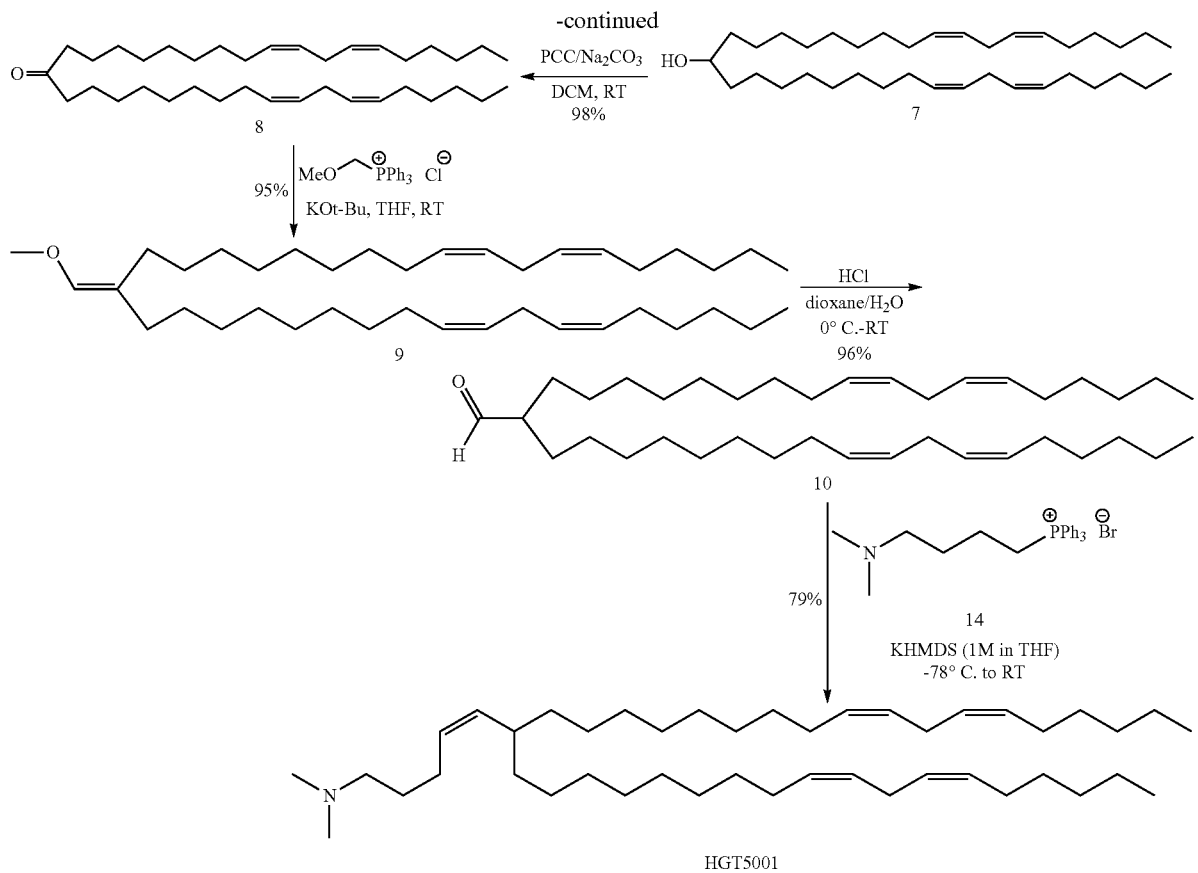

The intermediate compounds (6Z,9Z,28Z,31Z)-heptatriaconta-6,9,28,31-tetraen-19-yl formate (6) and (6Z,9Z,28Z,31Z)-heptatriaconta-6,9,28,31-tetraen-19-ol respectively identified as compounds (6) and (7) in Reaction 2 above were prepared in an oven dried 3-neck 500 mL flask that was charged with Mg (0.5 g, 20.83 mmol, 1.37 eq.) and $I_2$ (one crystal) under argon. The flask was degassed on a high-vacuum line, then flushed with argon (the process was repeated four times) and then stirred at room temperature for approximately 5 minutes. Anhydrous ether (22 mL) was added to this flask and the slurry stirred for approximately 10 minutes. Next, 5 g (15.2 mmol, 1 eq.) of compound (5) (linoleyl bromide) was added under argon (color change was observed after the addition of approximately 4.5 mL of compound (5)) and the reaction stirred at room temperature. An exothermic reaction was observed after stirring for approximately 5 minutes at room temperature. Thus, the mixture was cooled using an ice-water bath for approximately 2 minutes, then the ice-bath was removed and the reaction mixture stirred at room temperature for 2 hours, resulting in an ash colored reaction mixture and not all of the Mg was consumed. The mixture was cooled to 0° C. and the $HCO_2Et$ (0.58 mL, 7.17 mmol, 0.47 eq.) was added dropwise directly into the solution. After stirring at room temperature for 3 hours (product was observed after 1 hour by MS and TLC) the mixture was decanted and the Mg turnings washed with ether. The combined washings were diluted with ether (100 mL), washed with 10% $H_2SO_4$ (2×50 mL), water, brine and then dried ($Na_2SO_4$). The solution was filtered, concentrated and the residue purified by silica-gel column chromatography.

5-7% ether in hexanes eluted the alcohol (compound (7)) from the residue. Yield: 0.34 g (8%). Compound 7: $^1$H NMR (300 MHz, $CDCl_3$): δ 5.38-5.31 (m, 8H), 3.58 (br s, 1H), 2.76 (t, J=6 Hz, 4H), 2.04 (q, J=6.8 Hz, 8H), 1.39-1.26 (m, 40H), 0.88 (t, J=6.8 Hz, 6H). APCI[M+H] 527, 511 (—$H_2O$).

2% ether in hexanes eluted the formate (compound (6)) from the residue. Yield: 1.7 g (40%). Compound 6: $^1$H NMR (300 MHz, $CDCl_3$): δ 8.08 (s, 1H), 5.42-5.28 (m, 8H), 4.99-4.95 (m, 1H), 2.76 (t, J=6 Hz, 4H), 2.04 (q, J=6.6 Hz, 8H), 1.39-1.26 (m, 40H), 0.88 (t, J=6.6 Hz, 6H). APCI[M+H] 557. To obtain compound (7) from compound (6), KOH (powder, 0.76 g, 13.5 mmol, 1.4 eq.) was added to a cloudy solution of compound (6) (5.33 g, 9.59 mmol, 1 eq.) in $EtOH/H_2O$ (90 mL/16 mL). The reaction mixture was stirred at room temperature overnight under a $N_2$ atm. This mixture was then concentrated, diluted with ether, washed with 5% aq. HCl (2×100 mL), water and dried ($Na_2SO_4$). The solution was filtered, concentrated and then dried under high vacuum to obtain the compound (7) as a colorless oil. Yield: 4.9 g (96%). $^1$H NMR (300 MHz, $CDCl_3$): δ 5.38-5.31 (m, 8H), 3.58 (br s, 1H), 2.76 (t, J=6 Hz, 4H), 2.04 (q, J=6.8 Hz, 8H), 1.39-1.26 (m, 40H), 0.88 (t, J=6.8 Hz, 6H). APCI[M+H] 527, 511 (—$H_2O$).

The intermediate compound (6Z,9Z,28Z,31Z)-heptatriaconta-6,9,28,31-tetraen-19-one identified as compound (8) in Reaction 2 above was prepared as follows. To a solution of compound (7) (4.81 g, 9.09 mmol) in anhydrous $CH_2Cl_2$ (230 mL) was added portionwise $Na_2CO_3$ (0.49 g, 4.54 mmol) and then PCC (4.9 g, 22.7 mmol, 2.5 eq.) over a period of 15 minutes. The black mixture was stirred at room temperature for 1.5 hours. TLC showed completion of reaction. The reaction mixture was filtered through a silica-gel pad (200 g) and the pad washed with $CH_2Cl_2$ (3×400 mL). The filtrate was concentrated and dried on a high-vacuum line to obtain the ketone compound (8) as a colorless oil. Yield: 4.5 g (98%). $^1H$ NMR (300 MHz, $CDCl_3$): δ 5.36-5.33 (m, 8H), 2.76 (t, J=5.8 Hz, 4H), 2.37 (t, J=7.4 Hz, 4H), 2.04 (q, J=6 Hz, 8H), 1.32-1.27 (m, 36H), 0.88 (t, J=6.8 Hz, 6H). APCI[M+H] 527.

The intermediate compound (6Z,9Z,28Z,31Z)-19-(methoxymethylene) heptatriaconta-6,9,28,31-tetraene identified as compound (9) in Reaction 2 above was prepared as follows. A mixture of compound (8) (2.7 g, 5.12 mmol, 1 eq.) and (methoxymethyl)triphenyl phosphonium chloride (2.63 g, 7.67 mmol, 1.5 eq.) was degassed under high vacuum and flushed with argon (4 times). Anhydrous THF (68 mL) was added followed by 1M KOt-Bu in THF (7.67 mL, 7.67 mmol, 1.5 eq.) dropwise by syringe. The resulting red solution was stirred at room temperature overnight. The reaction mixture was diluted with ether, washed with water, brine and dried (Na2SO4). Removal of the solvent and chromatography (1-4% ether in hexanes) of the residue yielded the product compound (9) as a colorless oil. Yield: 2.7 g (95%). 1H NMR (300 MHz, CDCl3): δ 5.72 (s, 1H), 5.36-5.33 (m, 8H), 3.5 (s, 3H), 2.76 (t, J=6 Hz, 4H), 2.05-1.98 (m, 10H), 1.85-1.80 (m, 2H), 1.31-1.27 (m, 36H), 0.88 (t, J=6.6 Hz, 6H). APCI[M+H] 555.

The intermediate compound (11Z,14Z)-2-((9Z,12Z)-octadeca-9,12-dien-1-yl)icosa-11,14-dienal identified as compound (10) in Reaction 2 above was prepared as follows. To a cloudy solution of compound (9) (1.3 g, 2.34 mmol) in a dioxane/$H_2O$ (56 mL/29 mL) solution was added 4M HCl in dioxane (29 mL, 116 mmol, 49 eq.) at 0° C. dropwise over 10 minutes. The mixture was allowed to warm to room temperature and then stirred at room temperature for 40 hours (monitored by TLC). The mixture was then diluted with ether, cooled to 0° C. and then slowly quenched with aqueous $NaHCO_3$. The organic layer was separated, washed with brine, dried ($Na_2SO_4$), filtered, concentrated and the residue purified by silica-gel column chromatography. 1% ether in hexanes eluted the product compound (10) as a colorless oil. Yield: 1.21 g (96%). $^1H$ NMR (300 MHz, $CDCl_3$): δ 9.53 (d, J=3.3 Hz, 1H), 5.36-5.33 (m, 8H), 2.76 (t, J=5.8 Hz, 4H), 2.23-2.18 (m, 1H), 2.05-1.96 (m, 8H), 1.61-1.16 (m, 40H), 0.88 (t, J=7 Hz, 6H). APCI[M+H] 541.

The intermediate compound (4-Dimethylaminobutyl) triphenylphosphonium bromide (compound (14)) was prepared in accordance with the general synthetic scheme shown below is shown in Reaction 3.

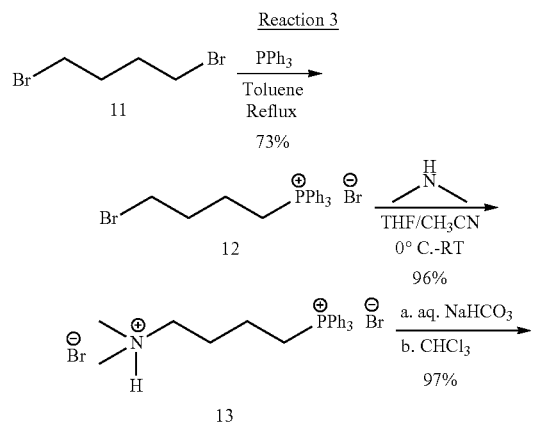

Reaction 3

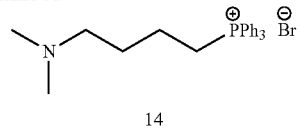

14

The intermediate compound (4-Bromobutyl)triphenylphosphonium bromide (compound (12)) depicted in Reaction 3 above was prepared by placing 10 g (46.3 mmol) of 1,4-dibromobutane (compound (11)) and 12.1 g $PPh_3$ (46.3 mmol) in dry toluene (74 mL), and the mixture heated to reflux and boiled overnight. The solid that formed was filtered, washed with toluene and dried under vacuum to provide the product compound (12) as a white solid. Yield: 16.1 g (73%). $^1H$ NMR (300 MHz, $CDCl_3$): δ 7.84-7.68 (m, 15H), 4.03-3.93 (m, 2H), 3.58 (t, J=6 Hz, 2H), 2.36-2.28 (m, 2H), 1.89-1.76 (m, 2H). APCI[M+H] 397 (M-Br), 399 (M+2-Br).

The intermediate compound (4-Dimethylaminobutyl) triphenylphosphonium bromide (compound (14)) was then prepared by adding 3 g (6.28 mmol, 1 eq.) of compound (12) portionwise to a solution of 2M dimethylamine in THF (31.4 mL, 62.8 mmol, 10 eq.) at 0° C. under $N_2$. The resulting suspension was allowed to stir at room temperature for 4 hours. $CH_3CN$ (35 mL) was then added to this suspension and it was further stirred at room temperature overnight. Nitrogen gas was then bubbled into the reaction mixture to remove excess dimethylamine and solvents. The resulting solid was dried under high vacuum and provided the dry product compound (13) as a light yellow solid. Yield: 3.16 g (96%). The product compound (13) was stirred with saturated aqueous $NaHCO_3$ (110 mL) for 15 minutes and lyophilized to produce a light yellow solid. This solid was stirred with chloroform and filtered. The filtrate was dried over $MgSO_4$, filtered, concentrated and the residue dried under high vacuum at 45° C. to produce the product compound (14) as a light pink solid. Yield: 2.7 g (97%). $^1H$ NMR (300 MHz, $CDCl_3$): δ 7.89-7.75 (m, 9H), 7.71-7.65 (m, 6H), 3.93-3.83 (m, 2H), 2.47 (t, J=6.8 Hz, 2H), 2.25 (s, 6H), 1.94-1.87 (m, 2H), 1.75-1.62 (m, 2H). APCI[M+H] 362 (M-Br).

HGT5001 ((15Z,18Z)—N,N-dimethyl-6-((9Z,12Z)-octadeca-9,12-dien-1-yl)tetracosa-4,15,18-trien-1-amine) was then prepared by adding charged intermediate compound (14) (0.58 g, 1.32 mmol, 1.5 eq.) to a flame dried RB flask (3-neck, 100 mL) and the flask was then equipped with a magnetic stir bar. This set-up was degassed (under high vacuum) and flushed with argon (3 times). Anhydrous THF (10 mL) was then added to the flask with a syringe. The resulting suspension was stirred under argon for 5 minutes and then cooled to −78° C. KHMDS (1M in THF, 1.32 mL, 1.32 mmol, 1.5 eq.) was then added dropwise to the reaction flask and resulted in a yellowish orange cloudy solution. This solution was stirred at −78° C. for 45 minutes. The cooling bath was removed and the reaction stirred at room temperature for 15 minutes to give a reddish orange solution. The mixture was cooled again to −78° C. and a solution of intermediate compound (10) (0.47 g, 0.88 mmol) in dry THF (13 mL) was added through a cannula. The reaction mixture color changed to light yellow. The reaction mixture was stirred at −78° C. for 45 minutes and then the cooling bath was removed, stirring was continued at room temperature for an additional 30 minutes. The mixture was cooled again to −20° C. and then quenched with water (7 mL). The reaction mixture was diluted with ether and stirred for 10 minutes. The organic layer was separated, washed with brine, dried over MgSO$_4$, filtered, concentrated and the residue purified by column chromatography on a silica-gel column. 1.5-2% methanol in chloroform eluted the HGT5001 product as a light yellow oil. Yield: 0.43 g (79%). $^1$H NMR (300 MHz, C$_6$D$_6$): δ 5.52-5.46 (m, 9H), 5.22-5.12 (m, 1H), 2.89 (t, J=5.8 Hz, 4H), 2.43 (br s, 1H), 2.24-2.03 (m, 18H), 1.55-1.37 (m, 2H), 1.35-1.22 (m, 40H), 0.88 (t, J=6.8 Hz, 6H). APCI[M+H] 624. Elemental analysis calculated for C$_{44}$H$_{81}$N (theory, found): C (84.67, 84.48); H (13.08, 13.12); N (2.24, 2.19).

Example 3

Lipid nanoparticles comprising HGT5000, DOPE, cholesterol and DMG-PEG2000 and encapsulating human erythropoietin (EPO) mRNA were formed via standard ethanol injection methods. (Ponsa, et al., *Int. J. Pharm.* (1993) 95: 51-56.) Ethanolic stock solutions of the lipids were prepared ahead of time at a concentration of 50 mg/mL and stored at −20° C.

Human erythropoietin (EPO) mRNA was synthesized by in vitro transcription from a plasmid DNA template encoding the gene, which was followed by the addition of a 5' cap structure (Cap1) (Fechter, P. et al., *J. Gen. Virology* (2005) 86: 1239-1249) and a 3' poly(A) tail of approximately 200 nucleotides in length as determined by gel electrophoresis. The 5' and 3' untranslated regions present in the EPO mRNA are represented as X and Y in SEQ ID NO: 1, as indicated below.

```
Human Erythropoietin mRNA:
                                            SEQ ID NO: 1
XAUGGGGGUGCACGAAUGUCCUGCCUGGCUGUGGCUUCUCCUGUCCCUGC

UGUCGCUCCCUCUGGGCCUCCCAGUCCUGGGCGCCCCACCACGCCUCAUC

UGUGACAGCCGAGUCCUGGAGAGGUACCUCUUGGAGGCCAAGGAGGCCGA

GAAUAUCACGACGGGCUGUGCUGAACACUGCAGCUUGAAUGAGAAUAUCA

CUGUCCCAGACACCAAAGUUAAUUUCUAUGCCUGGAAGAGGAUGGAGGUC

GGGCAGCAGGCCGUAGAAGUCUGGCAGGGCCUGGCCCUGCUGUCGGAAGC

UGUCCUGCGGGGCCAGGCCCUGUUGGUCAACUCUUCCCAGCCGUGGGAGC

CCCUGCAGCUGCAUGUGGAUAAAGCCGUCAGUGGCCUUCGCAGCCUCACC

ACUCUGCUUCGGGCUCUGGGAGCCCAGAAGGAAGCCAUCUCCCCUCCAGA

UGCGGCCUCAGCUGCUCCACUCCGAACAAUCACUGCUGACACUUUCCGCA

AACUCUUCCGAGUCUACUCCAAUUUCCUCCGGGGAAAGCUGAAGCUGUAC

ACAGGGGAGGCCUGCAGGACAGGGGACAGAUGAY

X = GGGAUCCUACC (SEQ ID NO: 2)
Y = UUUGAAUU   (SEQ ID NO: 3)
```

The EPO mRNA was stored in water at a final concentration of 1 mg/mL at −80° C. until the time of use. All mRNA concentrations were determined via the Ribogreen assay (Invitrogen). Encapsulation of mRNA was calculated by performing the Ribogreen assay with and without the presence of 0.1% Triton-X 100. Particle sizes (dynamic light scattering (DLS)) and zeta potentials were determined using a Malvern Zetasizer instrument in 1×PBS and 1 mM KCl solutions, respectively.

Aliquots of 50 mg/mL ethanolic solutions of the HGT5000, DOPE, cholesterol and DMG-PEG2K were mixed and diluted with ethanol to 3 mL final volume. Separately, an aqueous buffered solution (10 mM citrate/150 mM NaCl, pH 4.5) of EPO mRNA was prepared from a 1 mg/mL stock. The lipid solution was injected rapidly into the aqueous mRNA solution and shaken to yield a final suspension in 20% ethanol. The resulting nanoparticle suspension was filtered, diafiltrated with 1×PBS (pH 7.4), concentrated and stored at 2-8° C. Final concentration=1.82 mg/mL EPO mRNA (encapsulated). $Z_{ave}$=105.6 nm (Dv$_{(50)}$=53.7 nm; Dv$_{(90)}$=157 nm).

Example 4

Lipid nanoparticles comprising HGT5000, DOPE, cholesterol and DMG-PEG2000 and encapsulating human alpha-galactosidase (GLA) mRNA were formed via standard ethanol injection methods. (Ponsa, et al., *Int. J. Pharm.* (1993) 95: 51-56.) Ethanolic stock solutions of the lipids were prepared ahead of time at a concentration of 50 mg/mL and stored at −20° C.

Human GLA mRNA was synthesized by in vitro transcription from a plasmid DNA template encoding the gene, which was followed by the addition of a 5' cap structure (Cap1) (Fechter, P. et al., *J. Gen. Virology* (2005) 86: 1239-1249) and a 3' poly(A) tail of approximately 200 nucleotides in length as determined by gel electrophoresis. The 5' and 3' untranslated regions present in the GLA mRNA are represented as X and Y in SEQ ID NO: 4, as indicated below.

```
Alpha-galactosidase (GLA) mRNA:
                                            SEQ ID NO: 4
XAUGCAGCUGAGGAACCCAGAACUACAUCUGGGCUGCGCGCUUGCGCUUC

GCUUCCUGGCCCUCGUUUCCUGGGACAUCCCUGGGGCUAGAGCACUGGAC

AAUGGAUUGGCAAGGACGCCUACCAUGGGCUGGCUGCACUGGGAGCGCUU

CAUGUGCAACCUUGACUGCCAGGAAGAGCCAGAUUCCUGCAUCAGUGAGA

AGCUCUUCAUGGAGAUGGCAGAGCUCAUGGUCUCAGAAGGCUGGAAGGAU

GCAGGUUAUGAGUACCUCUGCAUUGAUGACUGUUGGAUGGCUCCCCAAAG

AGAUUCAGAAGGCAGACUUCAGGCAGACCCUCAGCGCUUUCCUCAUGGGA

UUCGCCAGCUAGCUAAUUAUGUUCACAGCAAAGGACUGAAGCUAGGGAUU

UAUGCAGAUGUUGGAAAUAAAACCUGCGCAGGCUUCCCUGGGAGUUUUGG

AUACUACGACAUUGAUGCCCAGACCUUUGCUGACUGGGGAGUAGAUCUGC

UAAAAUUUGAUGGUUGUUACUGUGACAGUUUGGAAAAUUUGGCAGAUGGU

UAUAAGCACAUGUCCUUGGCCCUGAAUAGGACUGGCAGAAGCAUUGUGUA

CUCCUGUGAGUGGCCUCUUUAUAUGUGGCCCUUUCAAAAGCCCAAUUAUA

CAGAAAUCCGACAGUACUGCAAUCACUGGCGAAAUUUUGCUGACAUUGAU

GAUUCCUGGAAAAGUAUAAAGAGUAUCUUGGACUGGACAUCUUUUAACCA

GGAGAGAAUUGUUGAUGUUGCUGGACCAGGGGGUUGGAAUGACCCAGAUA

UGUUAGUGAUUGGCAACUUUGGCCUCAGCUGGAAUCAGCAAGUAACUCAG

AUGGCCCUCUGGGCUAUCAUGGCUGCUCCUUUAUUCAUGUCUAAUGACCU

CCGACACAUCAGCCCUCAAGCCAAAGCUCUCCUUCAGGAUAAGGACGUAA

UUGCCAUCAAUCAGGACCCCUUGGGCAAGCAAGGGUACCAGCUUAGACAG

GGAGACAACUUUGAAGUGUGGGAACGACCUCUCUCAGGCUUAGCCUGGGC

UGUAGCUAUGAUAAACCGGCAGGAGAUUGGUGGACCUCGCUCUUAUACCA
```

-continued

```
UCGCAGUUGCUUCCCUGGGUAAAGGAGUGGCCUGUAAUCCUGCCUGCUUC

AUCACACAGCUCCUCCCUGUGAAAAGGAAGCUAGGGUUCUAUGAAUGGAC

UUCAAGGUUAAGAAGUCACAUAAAUCCCACAGGCACUGUUUUGCUUCAGC

UAGAAAAUACAAUGCAGAUGUCAUUAAAAGACUUACUUUAAY

X = GGGAUCCUACC (SEQ ID NO: 2)
Y = UUUGAAUU (SEQ ID NO: 3)
```

The GLA mRNA was stored in water at a final concentration of 1 mg/mL at −80° C. until the time of use. All mRNA concentrations were determined via the Ribogreen assay (Invitrogen). Encapsulation of mRNA was calculated by performing the Ribogreen assay with and without the presence of 0.1% Triton-X 100. Particle sizes (dynamic light scattering (DLS)) and zeta potentials were determined using a Malvern Zetasizer instrument in 1×PBS and 1 mM KCl solutions, respectively.

Aliquots of 50 mg/mL ethanolic solutions of the HGT5000, DOPE, cholesterol and DMG-PEG2K were mixed and diluted with ethanol to 3 mL final volume. Separately, an aqueous buffered solution (10 mM citrate/150 mM NaCl, pH 4.5) of GLA mRNA was prepared from the 1 mg/mL stock solution. The lipid solution was injected rapidly into the aqueous mRNA solution and shaken to yield a final suspension in 20% ethanol. The resulting nanoparticle suspension was filtered, diafiltrated with 1×PBS (pH 7.4), concentrated and stored at 2-8° C. Final concentration=1.38 mg/mL GLA mRNA (encapsulated). $Z_{ave}$=77.7 nm ($Dv_{(50)}$=62.3 nm; $Dv_{(90)}$=91.7 nm).

Example 5

Lipid nanoparticles comprising HGT5001, DOPE, cholesterol and DMG-PEG2000 and encapsulating human alpha-galactosidase (GLA) mRNA were formed via standard ethanol injection methods. (Ponsa, et al., *Int. J. Pharm.* (1993) 95: 51-56.) Ethanolic stock solutions of the lipids were prepared ahead of time at a concentration of 50 mg/mL and stored at −20° C.

Human alpha-galactosidase (GLA) mRNA was synthesized by in vitro transcription from a plasmid DNA template encoding the gene, which was followed by the addition of a 5' cap structure (Cap1) (Fechter, P. et al., *J. Gen. Virology* (2005) 86: 1239-1249) and a 3' poly(A) tail of approximately 200 nucleotides in length as determined by gel electrophoresis. The 5' and 3' untranslated regions present in the human alpha-galactosidase (GLA) mRNA are respectively represented as X and Y in SEQ ID NO: 4, as indicated below.

```
Human alpha-galactosidase (GLA) mRNA:
                                       SEQ ID NO: 4
XAUGCAGCUGAGGAACCCAGAACUACAUCUGGGCUGCGCGCUUGCGCUUC

GCUUCCUGGCCCUCGUUUCCUGGGACAUCCCUGGGGCUAGAGCACUGGAC

AAUGGAUUGGCAAGGACGCCUACCAUGGGCUGGCUGCACUGGGAGCGCUU

CAUGUGCAACCUUGACUGCCAGGAAGAGCCAGAUUCCUGCAUCAGUGAGA

AGCUCUUCAUGGAGAUGGCAGAGCUCAUGGUCUCAGAAGGCUGGAAGGAU

GCAGGUUAUGAGUACCUCUGCAUUGAUGACUGUUGGAUGGCUCCCCAAG

AGAUUCAGAAGGCAGACUUCAGGCAGACCCUCAGCGCUUUCCUCAUGGGA

UUCGCCAGCUAGCUAAUUAUGUUCACAGCAAAGGACUGAAGCUAGGGAUU

UAUGCAGAUGUUGGAAAUAAAACCUGCGCAGGCUUCCCUGGGAGUUUUGG

AUACUACGACAUUGAUGCCCAGACCUUUGCUGACUGGGGAGUAGAUCUGC

UAAAAUUUGAUGGUUGUUACUGUGACAGUUUGGAAAAUUUGGCAGAUGGU

UAUAAGCACAUGUCCUUGGCCCUGAAUAGGACUGGCAGAAGCAUUGUGUA

CUCCUGUGAGUGGCCUCUUUAUAUGUGGCCCUUUCAAAAGCCCAAUUAUA

CAGAAAUCCGACAGUACUGCAAUCACUGGCGAAAUUUUGCUGACAUUGAU

GAUUCCUGGAAAAGUAUAAAGAGUAUCUUGGACUGGACAUCUUUUAACCA

GGAGAGAAUUGUUGAUGUUGCUGGACCAGGGGGUUGGAAUGACCCAGAUA

UGUUAGUGAUUGGCAACUUUGGCCUCAGCUGGAAUCAGCAAGUAACUCAG

AUGGCCCUCUGGGCUAUCAUGGCUGCUCCUUUAUUCAUGUCUAAUGACCU

CCGACACAUCAGCCCUCAAGCCAAAGCUCUCCUUCAGGAUAAGGACGUAA

UUGCCAUCAAUCAGGACCCCUUGGGCAAGCAAGGGUACCAGCUUAGACAG

GGAGACAACUUUGAAGUGUGGGAACGACCUCUCUCAGGCUUAGCCUGGGC

UGUAGCUAUGAUAAACCGGCAGGAGAUUGGUGGACCUCGCUCUUAUACCA

UCGCAGUUGCUUCCCUGGGUAAAGGAGUGGCCUGUAAUCCUGCCUGCUUC

AUCACACAGCUCCUCCCUGUGAAAAGGAAGCUAGGGUUCUAUGAAUGGAC

UUCAAGGUUAAGAAGUCACAUAAAUCCCACAGGCACUGUUUUGCUUCAGC

UAGAAAAUACAAUGCAGAUGUCAUUAAAAGACUUACUUUAAY (SEQ ID NO: 2)

X = GGGAUCCUACC (SEQ ID NO: 2)
Y = UUUGAAUU (SEQ ID NO: 3)
```

Aliquots of 50 mg/mL ethanolic solutions of HGT5001, DOPE, cholesterol and DMG-PEG2K were mixed and diluted with ethanol to 3 mL final volume. Separately, an aqueous buffered solution (10 mM citrate/150 mM NaCl, pH 4.5) of GLA mRNA was prepared from a 1 mg/mL stock. The lipid solution was injected rapidly into the aqueous mRNA solution and shaken to yield a final suspension in 20% ethanol. The resulting nanoparticle suspension was filtered, diafiltrated with 1×PBS (pH 7.4), concentrated and stored at 2-8° C. Final concentration=0.68 mg/mL GLA mRNA (encapsulated). $Z_{ave}$=79.6 nm ($Dv_{(50)}$=57.26 nm; $Dv_{(90)}$=100 nm).

Example 6

Lipid nanoparticles comprising HGT5001, DOPE, cholesterol and DMG-PEG2000 and encapsulating human erythropoietin (EPO) mRNA were formed via standard ethanol injection methods. (Ponsa, et al., *Int. J. Pharm.* (1993) 95: 51-56.) Ethanolic stock solutions of the lipids were prepared ahead of time at a concentration of 50 mg/mL and stored at −20° C.

Human erythropoietin (EPO) mRNA was synthesized by in vitro transcription from a plasmid DNA template encoding the gene, which was followed by the addition of a 5' cap structure (Cap1) (Fechter, P. et al., *J. Gen. Virology* (2005) 86: 1239-1249) and a 3' poly(A) tail of approximately 200 nucleotides in length as determined by gel electrophoresis. The 5' and 3' untranslated regions present in the human erythropoietin (EPO) mRNA are respectively represented as X and Y in SEQ ID NO: 1, as indicated below.

```
Human Erythropoietin mRNA:
                                             SEQ ID NO: 1
XAUGGGGGUGCACGAAUGUCCUGCCUGGCUGUGGCUUCUCCUGUCCCUGC

UGUCGCUCCCUCUGGGCCUCCCAGUCCUGGGCGCCCCACCACGCCUCAUC

UGUGACAGCCGAGUCCUGGAGAGGUACCUCUUGGAGGCCAAGGAGGCCGA

GAAUAUCACGACGGGCUGUGCUGAACACUGCAGCUUGAAUGAGAAUAUCA

CUGUCCCAGACACCAAAGUUAAUUUCUAUGCCUGGAAGAGGAUGGAGGUC

GGGCAGCAGGCCGUAGAAGUCUGGCAGGGCCUGGCCCUGCUGUCGGAAGC

UGUCCUGCGGGGCCAGGCCCUGUUGGUCAACUCUUCCCAGCCGUGGGAGC

CCCUGCAGCUGCAUGUGGAUAAAGCCGUCAGUGGCCUUCGCAGCCUCACC

ACUCUGCUUCGGGCUCUGGGGAGCCCAGAAGGAAGCCAUCUCCCCUCCAGA

UGCGGCCUCAGCUGCUCCACUCCGAACAAUCACUGCUGACACUUUCCGCA

AACUCUUCCGAGUCUACUCCAAUUUCCUCCGGGGAAAGCUGAAGCUGUAC

ACAGGGGAGGCCUGCAGGACAGGGGACAGAUGAY

X = GGGAUCCUACC (SEQ ID NO: 2)
Y = UUUGAAUU (SEQ ID NO: 3)
```

Aliquots of 50 mg/mL ethanolic solutions of the HGT5001, DOPE, cholesterol and DMG-PEG2K were mixed and diluted with ethanol to 3 mL final volume. Separately, an aqueous buffered solution (10 mM citrate/150 mM NaCl, pH 4.5) of EPO mRNA was prepared from the 1 mg/mL stock. The lipid solution was injected rapidly into the aqueous mRNA solution and shaken to yield a final suspension in 20% ethanol. The resulting nanoparticle suspension was filtered, diafiltrated with 1×PBS (pH 7.4), concentrated and stored at 2-8° C. Final concentration=1.09 mg/mL EPO mRNA (encapsulated). $Z_{ave}$=62.1 nm ($Dv_{(50)}$=45.2 nm; $Dv_{(90)}$=74.6 nm).

Example 7

To determine whether the HGT5000-based lipid nanoparticles encapsulating human GLA mRNA and prepared in accordance with Example 4 above were capable of delivering encapsulated polynucleotide constructs to one or more target cells, a dose response study was conducted in wild type (CD-1) mice that were subsequently monitored for human GLA protein production.

The foregoing studies were performed using male or female CD-1 mice of approximately 6-8 weeks of age at the beginning of each experiment. Samples were introduced over a one week period at day 1 and again at day 5 by a single bolus tail-vein injection. The serum concentrations of GLA protein were determined at six hours, twenty-four hours, forty-eight hours and seventy-two hours following the administration of the second intravenous dose. Mice were sacrificed seventy-two hours following the administration of the second intravenous dose on day eight and organs were perfused with saline. The liver, spleen and when applicable, the brain, of each mouse was harvested, apportioned into two parts and stored in either 10% neutral buffered formalin or snap-frozen and stored at 80° C.

Figure 2:
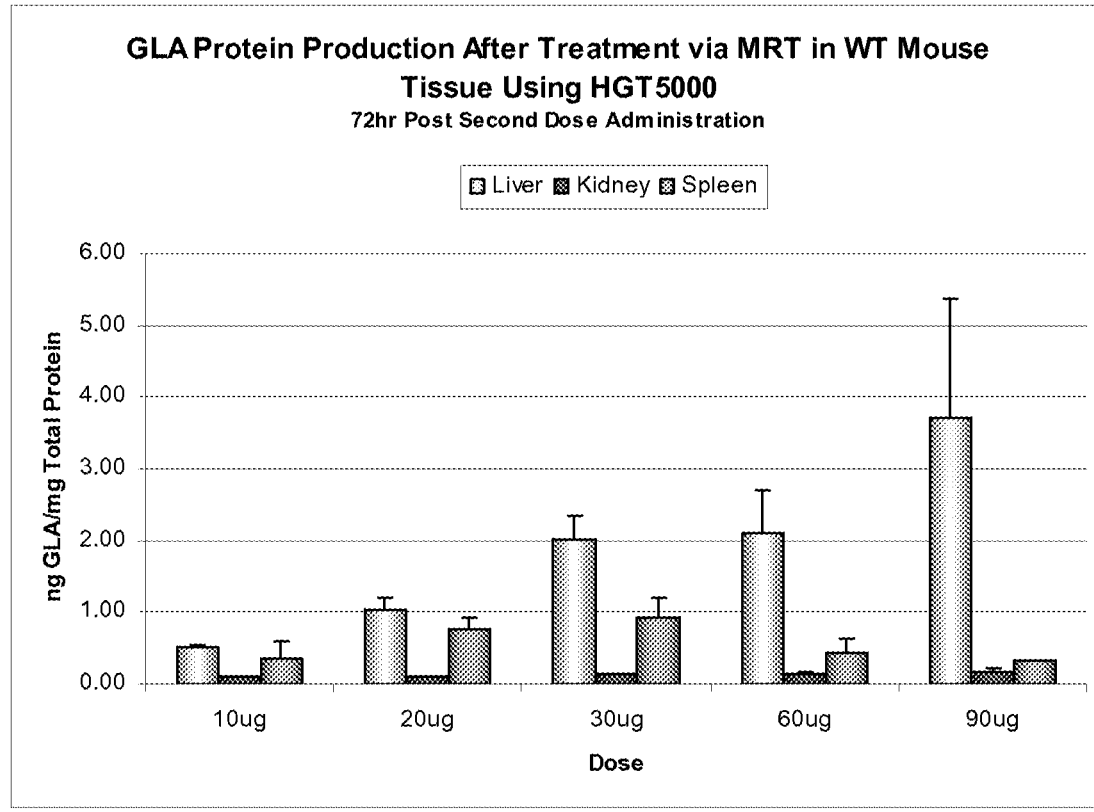
FIG. 2. depicts the concentration of human alpha-galactosidase (GLA) protein detected in the liver, kidney and spleen of wild type (WT) mice administered two single 90 µg, 60 µg, 30 µg, 20 µg or 10 µg doses of GLA mRNA encapsulated in an HGT5000-based lipid nanoparticle over a one week period, at day one and again at day five. The mice were sacrificed seventy-two hours following the administration of the second intravenous dose on day eight and the concentration of GLA protein in the liver, kidneys and spleen of the wild type (WT) mice was determined.

As illustrated in FIG. 1, following the intravenous injection of two 10 μg, 20 μg, 30 μg, 60 μg or 90 μg doses of GLA mRNA loaded in the HGT5000-based lipid nanoparticles, a substantial level of human GLA protein could be detected in mouse serum within 6 hours. Furthermore, detectable levels of GLA protein could be observed in the serum 48 hours following intravenous administration of the second single dose. As illustrated in FIG. 2, nanogram levels of human GLA protein were also detectable in select organs of the mice, such as the liver, kidney and spleen 72 hours following the administration of the second bolus tail-vein injection of GLA mRNA.

Figure 3:
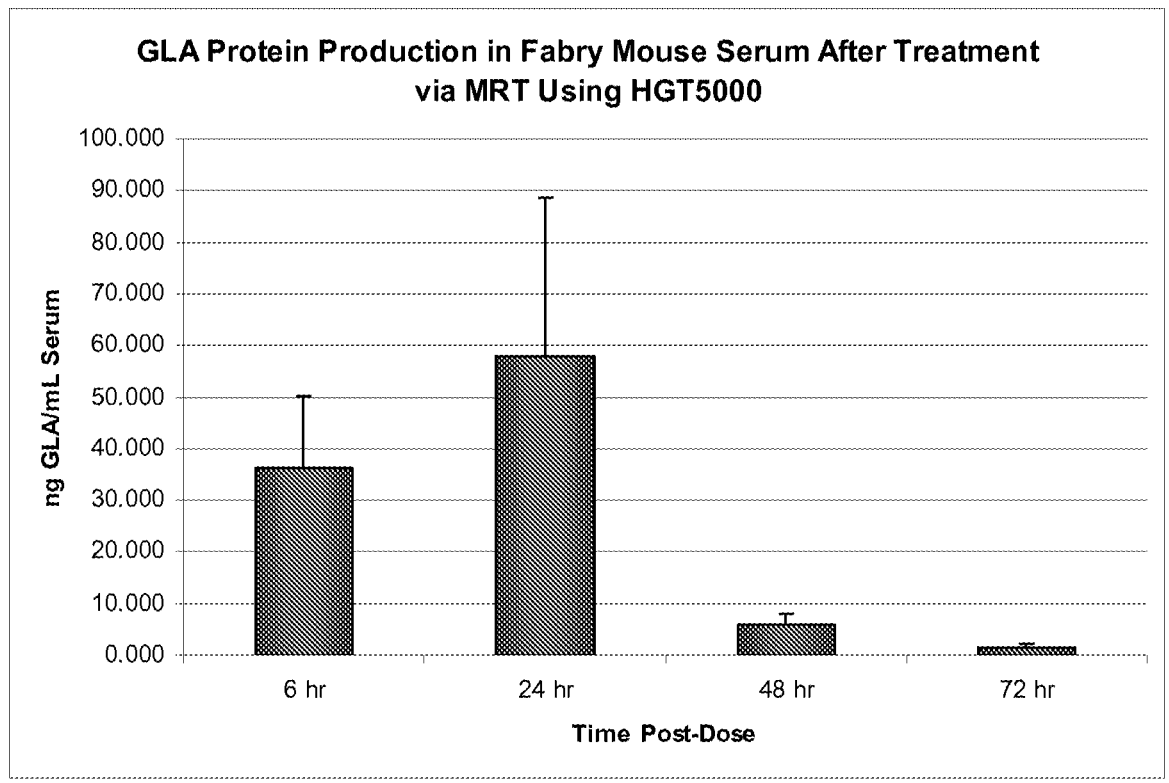
FIG. 3. illustrates the concentration of human alpha-galactosidase (GLA) protein detected in the serum of a murine model of Fabry disease over a seventy-two hour period following the intravenous administration of a single 90 µg intravenous dose of GLA mRNA encapsulated in an HGT5000-based lipid nanoparticle. Supraphysiological concentrations of GLA protein were detected in the serum of the Fabry mice twenty-four hours following the administration of a single 90 µg dose of the GLA mRNA encapsulated in an HGT5000-based lipid nanoparticle.
Figure 4:
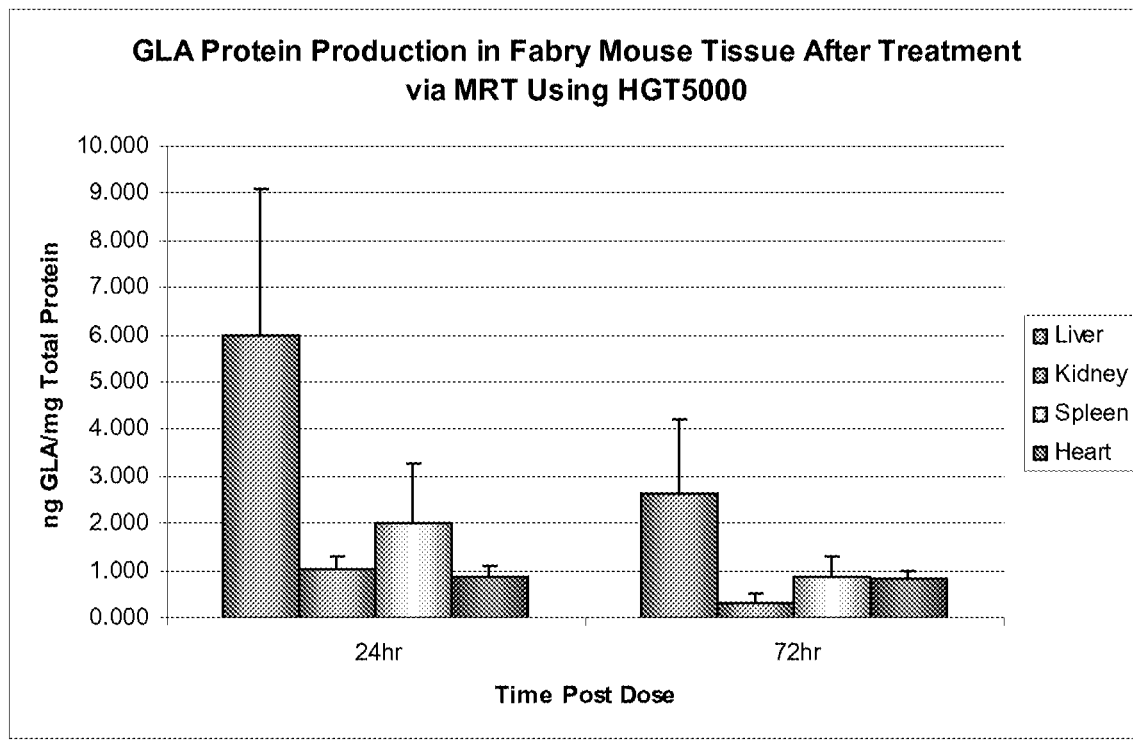
FIG. 4. depicts the concentration of human alpha-galactosidase (GLA) protein detected in the liver, kidney, spleen and heart of a murine model of Fabry disease at twenty-four and seventy-two hours following the intravenous administration of a single dose of GLA encapsulated in an HGT5000-based lipid nanoparticle. GLA protein was detectable in the evaluated organs of the Fabry mouse at twenty-four and seventy-two hours post-administration of the GLA mRNA, as shown in FIG. 4.

Additional studies evaluating the HGT5000-based lipid nanoparticles encapsulating human GLA mRNA and prepared in accordance with Example 4 above were also performed using a murine model of Fabry disease. Samples were introduced by a single bolus 90 μg dose (based on encapsulated GLA) of the GLA-loaded lipid nanoparticle via a tail-vein injection. Supraphysiological levels of GLA protein (approximately 50 times higher) were detected in the serum 24 hours post-administration of the single 90 ug dose of GLA. As illustrated in FIG. 3 and FIG. 4, human GLA protein was detectable in the serum and in select organs of the Fabry mice following the administration of a bolus tail-vein injection of the HGT5000-based lipid nanoparticle encapsulating GLA mRNA. In particular, human GLA protein was detected in the serum of the Fabry mice following administration of the GLA mRNA-loaded HGT5000-based lipid nanoparticles over a 72 hour time period. Human GLA protein levels were also detectable in select Fabry mouse organs following the administration of the GLA mRNA-loaded HGT5000-based lipid nanoparticles both at 24 hours and 72 hours post-administration.

Example 8

To determine whether the HGT5001-based lipid nanoparticles encapsulating human GLA mRNA and prepared in accordance with Example 5 above were capable of delivering encapsulated polynucleotide constructs to one or more target cells, a dose response study was conducted in wild type (CD-1) mice that were subsequently monitored for human GLA protein production.

The foregoing studies were performed using male or female CD-1 mice of approximately 6-8 weeks of age at the beginning of each experiment. Samples were introduced by a single bolus tail-vein injection. Mice were sacrificed at designated time points and organs were perfused with saline. The liver, spleen and when applicable, the brain, of each mouse was harvested, apportioned into two parts and stored in either 10% neutral buffered formalin or snap-frozen and stored at –80° C.

Figure 5:
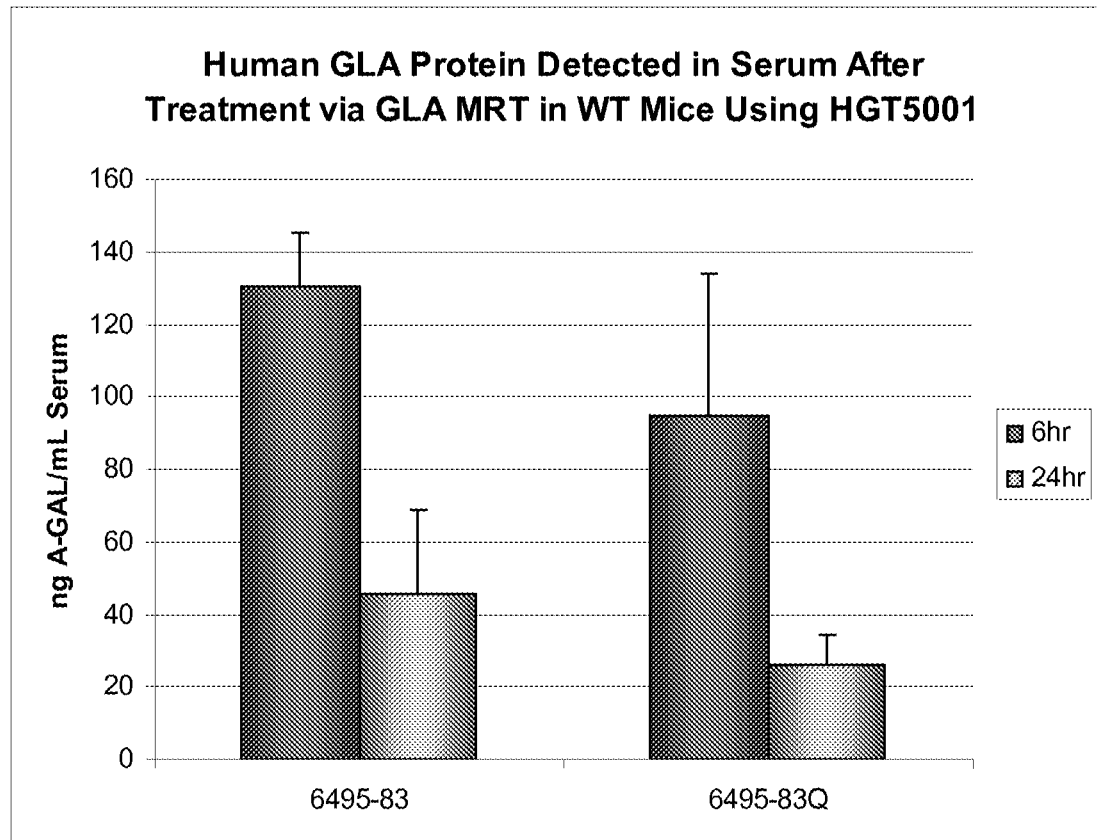
FIG. 5. illustrates the concentrations of human alpha-galactosidase (GLA) protein detected in wild type (WT) mouse serum over a twenty-four hour period following the intravenous injection of a 30 µg dose of GLA mRNA encapsulated in an HGT5001-based lipid nanoparticle. As depicted in FIG. 5, within six hours of administration of the GLA mRNA, human GLA protein was detected in serum at concentrations exceeding normal physiological levels by 100-fold. Similarly, within twenty-four hours following administration of the GLA mRNA, human GLA protein was detected in serum at concentrations exceeding normal physiological levels by 30-fold.
Figure 6:
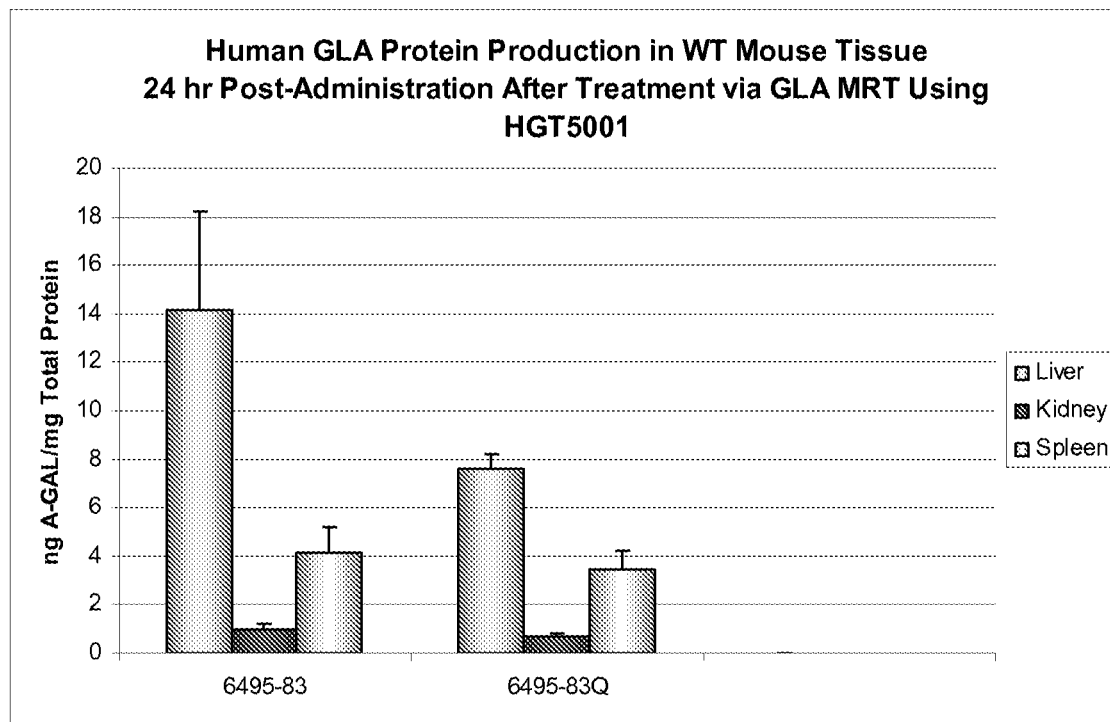
FIG. 6. illustrates the concentrations of human alpha-galactosidase (GLA) protein detected in the liver, kidney and spleen of wild type (WT) mice over a twenty-four hour period following the intravenous injection of GLA mRNA encapsulated in an HGT5001-based lipid nanoparticle. As depicted in FIG. 6, substantial levels of human GLA protein could be detected in the liver, kidney and spleen of the WT mice twenty-four hours following the intravenous administration of GLA mRNA encapsulated in an HGT5001-based lipid nanoparticle.

The a single 30 μg dose of the HGT50001-based GLA mRNA-loaded lipid nanoparticles were administered to the wild type mice, and as illustrated in FIG. 5 at 6 hours post-administration, human GLA protein was detected in serum at concentrations that exceeded normal physiological levels by 100-fold. As also depicted in FIG. 5, twenty-four hours following administration of the HGT5001-based GLA mRNA-loaded lipid nanoparticles to the wild type mice, human GLA protein remained detectable at concentrations that exceeded normal physiological concentrations by 30-fold higher. Further, as depicted in FIG. 6, substantial concentrations of human GLA protein could be detected in the liver, kidney and spleen of the wild-type mice after treatment twenty-four hours post administration of the HGT5001-based GLA mRNA-loaded lipid nanoparticles.

Example 9

The instant study was conducted to further demonstrate the ability of both the HGT5000-based and the HGT5001-based lipid nanoparticles to deliver encapsulated human erythropoietin (EPO) mRNA to one or more target cells in wild-type Sprague Dawley rats. HGT5000 and HGT50001-based EPO mRNA-loaded lipid nanoparticles were prepared in accordance with the protocols set forth in the foregoing examples. Samples were administered by a single bolus tail-vein injection. The concentration of EPO protein secreted into the bloodstream was monitored over a twenty-four hour time period, with serum samples obtained at six, twelve, eighteen and twenty-four hours following administration.

Figure 7:
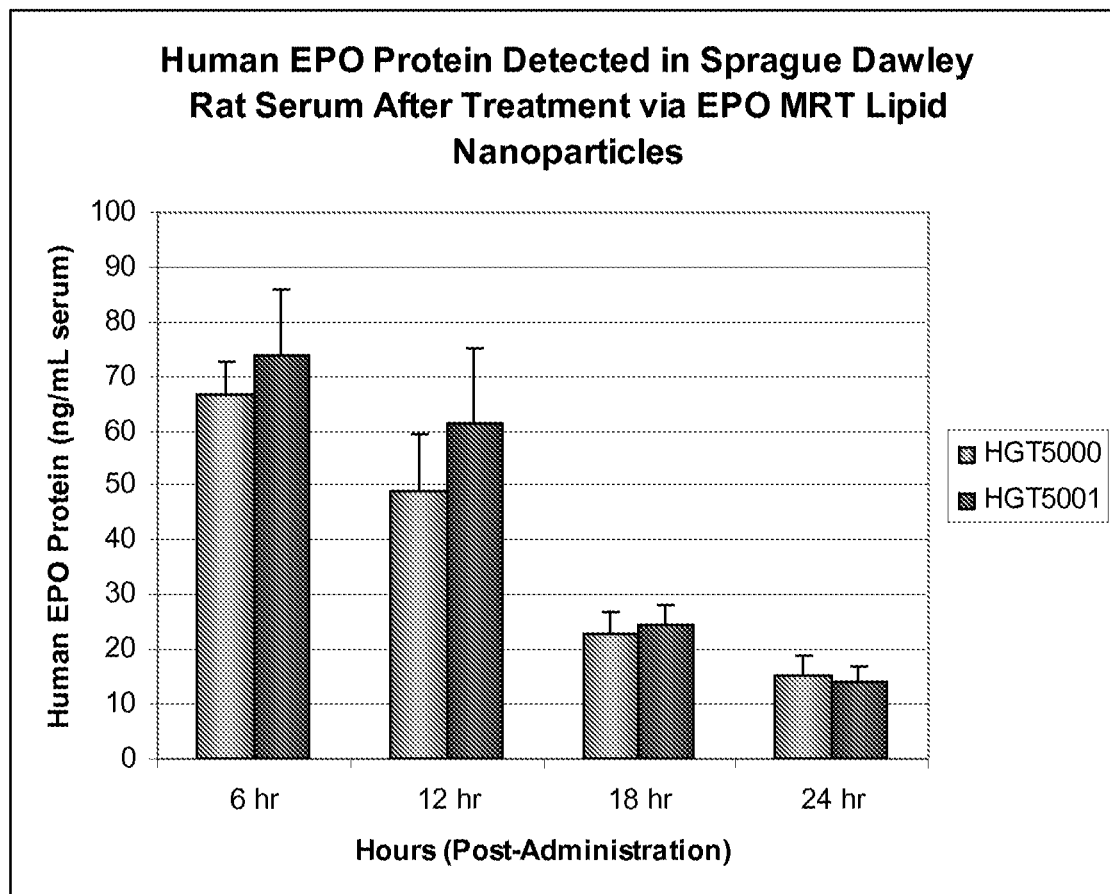
FIG. 7. compares the serum concentrations of human erythropoietin (EPO) protein detected in Sprague-Dawley rats following the intravenous administration of a single dose of EPO mRNA encapsulated in either an HGT5000- or an HGT5001-based lipid nanoparticle over a twenty-four hour period.

Human EPO protein was detected in the Sprague-Dawley rat serum following administration of the EPO mRNA-loaded HGT5000- and HGT5001-based lipid nanoparticles over a twenty-four hour time period. As shown in FIG. 7, both HGT5000-based and HGT5001-based lipid nanoparticles resulted in efficacious protein production in the wild-type Sprague Dawley rats. Significant levels of human EPO protein were detected over the course of this study for both HGT5000 and HGT5001-based nanoparticle systems. Accordingly, the present example illustrates that both HGT5000- and HGT5001-based lipid nanoparticles provide highly efficacious means of delivering polynucleotide constructs to one or more target cells and that following expression of such lipid nanoparticles to such target cells, the expressed protein encoded by the encapsulated mRNA was detectable in serum.

DISCUSSION

The foregoing studies illustrate that the lipid compounds disclosed herein are useful as liposomal delivery vehicles or as components of liposomal delivery vehicles. In particular, such compounds and compositions facilitate the delivery encapsulated polynucleotides (e.g., mRNA polynucleotides encoding functional proteins or enzymes) to one or more target cells, tissues and organs, thereby causing such cells to express the encapsulated polynucleotide. For example, following a single intravenous injection of a given dose of an mRNA polynucleotide encapsulated in an HGT5000-based lipid nanoparticle, a substantial concentration of the encoded protein was detected in both serum and in one or more target organs of the subject mice. Furthermore, as evident by Example 8, in many instances the concentration of expressed protein well exceeded those concentrations necessary for therapeutic efficacy, therefore suggesting that only a fraction of the administered dose of the compositions are necessary to achieve therapeutically effective concentrations within the plasma, target organ, tissue or cells. As a result, the total administered amount of cationic lipid that is necessary to deliver a therapeutically effective amount of the encapsulated agent may be reduced, resulting in a corresponding reduction in the toxicity of the compositions.

We claim:
1. A lipid nanoparticle comprising:
mRNA; and
a cationic lipid having the following structure

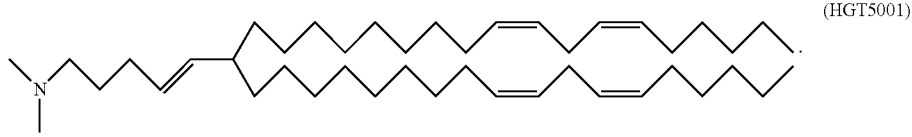

(HGT5001)

2. The lipid nanoparticle of claim 1, further comprising one or more lipids selected from the group consisting of a cationic lipid, a neutral lipid, a PEG-modified lipid, a non-cationic lipid and a helper lipid.

3. The lipid nanoparticle of claim 1, further comprising C14-DMG-PEG2000, DOPE and cholesterol.

4. A method of treating disease in a subject, wherein the method comprises administering an effective amount of the lipid nanoparticle of claim 1 to the subject.

5. A method of transfecting one or more target cells with a polynucleotide, wherein the method comprises contacting the one or more target cells with the lipid nanoparticle of claim 1 such that the one or more target cells are transfected with the polynucleotide.

6. The lipid nanoparticle of claim 1, wherein the mRNA encodes an enzyme or a protein.

7. The lipid nanoparticle of claim 6, wherein the mRNA encodes the protein or enzyme selected from the group consisting of human growth hormone, erythropoietin, al-antitrypsin, acid alpha glucosidase, arylsulfatase A, carboxypeptidase N, α-galactosidase A, alpha-L-iduronidase, iduronate-2-sulfatase, iduronate sulfatase, N-acetylglucosamine-1-phosphate transferase, N-acetylglucosaminidase, alpha-glucosaminide acetyltransferase, N-acetylglucosamine 6-sulfatase, N-acetylgalactosamine-4-sulfatase, beta-glucosidase, galactose-6-sulfate sulfatase, beta-galactosidase, beta-glucuronidase, glucocerebrosidase, heparan sulfamidase, heparin-N-sulfatase, lysosomal acid lipase, hyaluronidase, galactocerebrosidase, ornithine transcarbamylase (OTC), carbamoyl-phosphate synthetase 1 (CPS1), argininosuccinate synthetase (ASS1), argininosuccinate lyase (ASL), arginase 1 (ARG1), cystic fibrosis transmembrane conductance regulator (CFTR), survival motor neuron (SMN), Factor VIII, Factor IX and low density lipoprotein receptors (LDLR).

8. The lipid nanoparticle of claim 1, further comprising one or more helper lipids, non-cationic lipids, and PEG-modified lipid components.

9. The lipid nanoparticle of claim 1, further comprising DOPE, cholesterol, and/or DMG-PEG2000.

10. A lipid nanoparticle comprising:
mRNA; and
a cationic lipid having the structure,

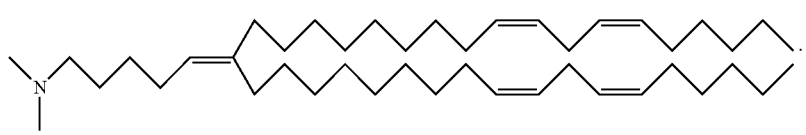

(HGT5002)

11. The lipid nanoparticle of claim 10, further comprising one or more lipids selected from the group consisting of a cationic lipid, a neutral lipid, a PEG-modified lipid, a non-cationic lipid and a helper lipid.

12. The lipid nanoparticle of claim 10, further comprising C14-DMG-PEG2000, DOPE and cholesterol.

13. A method of treating disease in a subject, wherein the method comprises administering an effective amount of the lipid nanoparticle of claim 10 to the subject.

14. A method of transfecting one or more target cells with a polynucleotide, wherein the method comprises contacting the one or more target cells with the lipid nanoparticle of claim 10 such that the one or more target cells are transfected with the polynucleotide.

15. The lipid nanoparticle of claim 10, wherein the mRNA encodes an enzyme or a protein.

16. The lipid nanoparticle of claim 15, wherein the mRNA encodes the protein or enzyme selected from the group consisting of human growth hormone, erythropoietin, al-antitrypsin, acid alpha glucosidase, arylsulfatase A, carboxypeptidase N, α-galactosidase A, alpha-L-iduronidase, iduronate-2-sulfatase, iduronate sulfatase, N-acetylglucosamine-1-phosphate transferase, N-acetylglucosaminidase, alpha-glucosaminide acetyltransferase, N-acetylglucosamine 6-sulfatase, N-acetylgalactosamine-4-sulfatase, beta-glucosidase, galactose-6-sulfate sulfatase, beta-galactosidase, beta-glucuronidase, glucocerebrosidase, heparan sulfamidase, heparin-N-sulfatase, lysosomal acid lipase, hyaluronidase, galactocerebrosidase, ornithine transcarbamylase (OTC), carbamoyl-phosphate synthetase 1 (CPS1), argininosuccinate synthetase (ASS1), argininosuccinate lyase (ASL), arginase 1 (ARG1), cystic fibrosis transmembrane conductance regulator (CFTR), survival motor neuron (SMN), Factor VIII, Factor IX and low density lipoprotein receptors (LDLR).

17. The lipid nanoparticle of claim 10, further comprising one or more helper lipids, non-cationic lipids, and PEG-modified lipid components.

18. The lipid nanoparticle of claim 10, further comprising DOPE, cholesterol, and/or DMG-PEG2000.

* * * * *

UNITED STATES PATENT AND TRADEMARK OFFICE
CERTIFICATE OF CORRECTION

PATENT NO. : 10,766,852 B2
APPLICATION NO. : 16/100853
DATED : September 8, 2020
INVENTOR(S) : DeRosa et al.

It is certified that error appears in the above-identified patent and that said Letters Patent is hereby corrected as shown below:

In the Specification

• Column 40, Line 5:
Delete "hormone, erythropoietin, al-antitrypsin, acid alpha glucosi-"
Replace with --hormone, erythropoietin, α1-antitrypsin, acid alpha glucosi- --

In the Claims

• Claim 7, Column 61, Line 31:
Delete "consisting of human growth hormone, erythropoietin, al- --
Replace with --consisting of human growth hormone, erythropoietin, α1- --

• Claim 16, Column 62, Line 32:
Delete "consisting of human growth hormone, erythropoietin, al-"
Replace with --consisting of human growth hormone, erythropoietin, α1- --

Signed and Sealed this
Eighteenth Day of July, 2023

Katherine Kelly Vidal
*Director of the United States Patent and Trademark Office*